(12) United States Patent
Schnermann et al.

(10) Patent No.: US 11,465,993 B2
(45) Date of Patent: Oct. 11, 2022

(54) WATER SOLUBLE NOVEL CYANINE FLUOROPHORE WITH TUNABLE PROPERTIES BETWEEN NEAR IR AND SWIR REGION FOR IN VIVO IMAGING

(71) Applicant: The USA, as represented by the Secretary, Department of Health and Human Services, Bethesda, MD (US)

(72) Inventors: Martin J. Schnermann, Rockville, MD (US); Venu G. Bandi, Frederick, MD (US)

(73) Assignee: The United States of America, as Represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 17/269,517

(22) PCT Filed: Aug. 23, 2019

(86) PCT No.: PCT/US2019/047972
§ 371 (c)(1),
(2) Date: Feb. 18, 2021

(87) PCT Pub. No.: WO2020/041743
PCT Pub. Date: Feb. 27, 2020

(65) Prior Publication Data
US 2021/0179597 A1    Jun. 17, 2021

Related U.S. Application Data

(60) Provisional application No. 62/721,986, filed on Aug. 23, 2018.

(51) Int. Cl.
| | |
|---|---|
| *C07D 409/14* | (2006.01) |
| *C07D 209/18* | (2006.01) |
| *C07D 403/14* | (2006.01) |
| *C07D 405/14* | (2006.01) |
| *C09B 23/01* | (2006.01) |

(52) U.S. Cl.
CPC ......... *C07D 409/14* (2013.01); *C07D 209/18* (2013.01); *C07D 403/14* (2013.01); *C07D 405/14* (2013.01); *C09B 23/0066* (2013.01)

(58) Field of Classification Search
CPC .. C07D 409/14; C07D 209/18; C07D 403/14; C07D 405/14
See application file for complete search history.

(56) References Cited

U.S. PATENT DOCUMENTS

| | | | |
|---|---|---|---|
| 10,280,307 | B2 | 5/2019 | Schnermann et al. |
| 10,561,729 | B2 | 2/2020 | Schnermann et al. |
| 2020/0179536 | A1 | 6/2020 | Schnermann et al. |
| 2021/0017132 | A1 | 1/2021 | Schnermann et al. |

FOREIGN PATENT DOCUMENTS

| | | |
|---|---|---|
| EP | 2 719 540 A1 | 4/2014 |
| JP | 2000 169741 A1 | 6/2000 |
| WO | WO 2017/027721 A1 | 2/2017 |
| WO | WO 2019/161091 A1 | 8/2019 |

OTHER PUBLICATIONS

Gorka et al., "A Near-IR Uncaging Strategy Based on Cyanine Photochemistry," *Journal of American Chemical Society*, 7 pages (Sep. 11, 2014).
Gorka et al., "Harnessing cyanine photooxidation: from slowing photobleaching to near-IR uncaging," *Current Opinion in Chemical Biology*, 33:117-125 (2016).
International Search Report and Written Opinion, dated Nov. 22, 2019, issued in corresponding International Application No. PCT/US2019/047972, 16 pages.
Luciano, "Bright, Stable Heptamethine Cyanine Fluorophores for In Vivo Imaging," NIH Research Festival: Chemical Biology Symposium, 14 pages, (Sep. 13, 2018).
Nani et al., "Electrophile-Integrating Smiles Rearrangement Provides Previously Inaccessible C4'-O-Alkyl Heptamethine Cyanine Fluorophores," *Org. Lett.*, 17:302-305 (Jan. 6, 2015).
Nani et al., "In Vivo Activation of Duocarmycin-Antibody Conjugates by Near-Infrared Light," *ACS Cent. Sci.*, 3:329-337 (2017).
Nani et al., "Near-IR Light-Mediated Cleavage of Antibody-Drug Conjugates Using Cyanine Photocages," *Angew. Chem. Int. Ed.*, 54:13635-13638 (2015).
Naud-Martin et al., "Acri-2,7-Py, a bright red-emitting DNA probe identified through screening of a distyryl dye library," *Biochemical. J.*, 2014, 9, 301-310.
Sato et al., "Effect of charge localization on the in vivo optical imaging properties of near-infrared cyanine dye/monoclonal antibody conjugates," *Mol. BioSyst.*, 12:3046-3056 (2016).
Sato et al., "Role of Fluorophore Charge on the In Vivo Optical Imaging Properties of Near-Infrared Cyanine Dye/Monoclonal Antibody Conjugates," *Bioconjugate Chem.*, 27:404-413 (Oct. 7, 2015).
SciFinder Results, *American Chemical Society*, Jul. 2018, 1 page.

*Primary Examiner* — Shawquia Jackson
(74) *Attorney, Agent, or Firm* — Klarquist Sparkman, LLP

(57) ABSTRACT

Cyanine fluorophores including a nine-carbon polymethine bridge are disclosed. The cyanine fluorophores have absorbance and/or emission maxima in the near-infrared (NIR) and short-wave infrared (SWIR) wavelength ranges. Methods of making and using the cyanine fluorophores are also disclosed. The compounds are useful in fluorescence imaging, more particularly in cancer treatment. The compounds have generic formula (I):

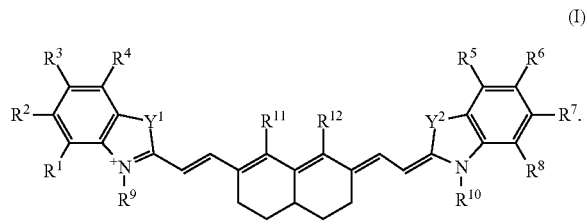

19 Claims, 49 Drawing Sheets

FIG. 1A

| Compound | Solvent | λmax,abs (nm) | λmax,emiss (nm) | ε (M⁻¹cm⁻¹) |
|---|---|---|---|---|
| NIR-970, yield 28% | PBS<br>FBS<br>Methanol | 920<br>940<br>938 | 970<br>990<br>990 | 55,000<br>53,000<br>102,000 |
| NIR-900-Et, yield 45% | PBS<br>FBS<br>Methanol | 856<br>864<br>860 | 900<br>900<br>890 | 172,000<br>148,000<br>253,000 |
| SWIR-1080, yield 27% | PBS<br>FBS<br>Methanol | 1058<br>1062<br>1072 | 1084<br>1086<br>1103 | 70,000<br>99,000<br>117,000 |
| NIR-900, yield 46% | PBS<br>FBS<br>Methanol | 862<br>871<br>869 | 896<br>900<br>896 | 145,000<br>137,000<br>187,000 |
| HexaSO₃-NIR-900, yield 28% | PBS<br>Methanol | 856<br>~860 | ~900<br>~900 | ND<br>ND |
| NIR-900-Peg₄₄-COOH, yield 33% | PBS | 856 | ~900 | ND |

FIG. 1B

| Compound | Solvent | $\lambda_{max,abs}$ (nm) | $\lambda_{max,emiss}$ (nm) | $\epsilon$ (M$^{-1}$cm$^{-1}$) |
|---|---|---|---|---|
| NIR-890-Peg4-COOH, yield 58% | PBS | 856 | 900 | ND |
| NIR-950, yield 37% | PBS<br>FBS<br>Methanol | 880<br>902<br>890 | 950<br>955<br>960 | 79,000<br>128,000<br>193,000 |
| SWIR-1080-no COOH, yield 27% | PBS<br>FBS<br>Methanol | 1046<br>1056<br>1056 | 1080<br>1090<br>1100 | 76,000<br>131,000<br>154,000 |
| N-methyl-NIR-990, yield 17% | DCM<br>Methanol | 940<br>922 | 990<br>960 | 134,000<br>46,000 |
| NIR-830, yield 76% | PBS<br>Methanol | 790<br>810 | 830<br>830 | ND<br>ND |
| Bis(SO3Peg3)-NIR-DiCl, yield 24% | ND | ND | ND | ND |

FIG. 1C

| Compound | Solvent | $\lambda_{max,abs}$ (nm) | $\lambda_{max,emiss}$ (nm) | $\varepsilon$ (M$^{-1}$cm$^{-1}$) |
|---|---|---|---|---|
| Bis(SO₃Peg₃)-NIR-900, yield 51% | PBS | 860 | ~900 | ND |
| Bis(SO₃Peg₃)-SWIR-1080, yield 28% | ND | ND | ND | ND |
| NIR-900-Umb | ND | ND | ND | ND |
| BisSO₃-NIR-890, yield 65% | PBS<br>FBS<br>Methanol | 689<br>877<br>850 | 890<br>900<br>890 | ND<br>187,000<br>275,000 |

FIG. 1D

| Compound | Solvent | λ$_{max,abs}$ (nm) | λ$_{max,emiss}$ (nm) | ε (M$^{-1}$cm$^{-1}$) |
|---|---|---|---|---|
| SWIR-1090, yield 20% | PBS<br>FBS<br>Methanol | 1065<br>1074<br>1074 | 1090<br>1090<br>1096 | 38,000<br>37,000<br>72,000 |
| SWIR-1080-Biotin, yield 29% | ND | ND | ND | ND |
| N-methyl-SWIR-1080, yield 22% | ND | ND | ND | ND |
| NIR-890, yield 38% | PBS<br>FBS<br>Methanol | 860<br>868<br>866 | 896<br>896<br>896 | 191,000<br>192,000<br>208,000 |
| NIR-900-Dextran | ND | ND | ND | ND |

FIG. 1E

| Compound | Solvent | $\lambda_{max,abs}$ (nm) | $\lambda_{max,emiss}$ (nm) | $\varepsilon$ (M$^{-1}$cm$^{-1}$) |
|---|---|---|---|---|
| C$_{36}$-NIR-910, yield 11% | ND | ND | ND | ND |
| NIR-820, yield 20% | PBS | 600 | 820 | ND |
| NIR-900-Panitumumab | PBS | 860 | 900 | ND |
| NIR-900-Et-Panitumumab | PBS | 860 | ND | ND |
| NIR-890-Peg$_4$-Panitumumab | PBS | 860 | ND | ND |

| Compound | Solvent | λmax,abs (nm) | λmax,emiss (nm) | ε (M⁻¹cm⁻¹) |
|---|---|---|---|---|
|  NIR-890-Panitumumab | PBS | 890 | 900 | ND |
|  SWIR-1080-Panitumumab | PBS | 1058 | 1086 | ND |
|  SWIR-1090-Panitumumab | PBS | 1065 | 1090 | ND |

| Compound | Solvent | λ$_{max,abs}$ (nm) | λ$_{max,emiss}$ (nm) | ε (M$^{-1}$cm$^{-1}$) |
|---|---|---|---|---|
|  NIR-900-Et-Dextran 10kDa | ND | 860 | ND | ND |
|  NIR-900-Dextran 10kDa | PBS | 860 | ND | ND |
|  SWIR-1080-Dextran 10kDa | PBS | 1058 | ND | ND |
|  SWIR-1080-Dextran 70kDa | PBS | 1058 | ND | ND |
|  pH-SWIR-1080, yield 16% | pH 7.5 PBS<br>pH 4.4 PBS | 650<br>1056 | No emis<br>1080 | 29,00<br>21,000 |
|  pH-SWIR-1080-COOH, yield 15% | pH 7.5 PBS<br>pH 4.4 PBS | 650<br>1056 | No emis<br>1080 | ND<br>ND |
|  pH-NIR-970, yield 4.5% | ND | ND | ND | ND |

| Compound | Solvent | $\lambda_{max,abs}$ (nm) | $\lambda_{max,emiss}$ (nm) | $\varepsilon$ (M$^{-1}$cm$^{-1}$) |
|---|---|---|---|---|
|  pH-SWIR-1080-cRGDfK, yield 36% | ND | ND | ND | ND |
|  N-methyl-SWIR-1080, yield 22% | ND | ND | ND | ND |
|  N-methyl-NIR-970 | ND | ND | ND | ND |
|  N-propyl-NIR-970 | ND | ND | ND | ND |
|  N-methyl-Mero-NIR-780, Yield 49% | Acetonitrile | 600 | 780 | ND |
|  N-methyl-NIR-900 | Acetonitrile 0.1%Formic acid in acetonitrile | 540 872 | 720 906 | ND ND |
|  N-methyl-SWIR-1080, Yield 33% | DCM Methanol | 1066 1047 | 1110 1085 | ND ND |

FIG. 1I

| Compound | Solvent | λ$_{max,abs}$ (nm) | λ$_{max,emiss}$ (nm) | ε (M$^{-1}$cm$^{-1}$) |
|---|---|---|---|---|
| Benzo-NIR-Dichloro | ND | ND | ND | ND |
| Benzo-NIR-930, Yield 21% | PBS | 884 | 919 | ND |
| | FBS | 911 | 937 | ND |
| | Methanol | 900 | 936 | ND |

PBS = phosphate-buffered saline, pH 7.4, FBS = 10% fetal bovine serum, DCM = dichloromethane, pH 7.5 PBS = 20% DMSO in phosphate-buffered saline, pH 4.4 PBS = 20% DMSO in phosphate-buffered saline ND= not determined.

WATER SOLUBLE NOVEL CYANINE FLUOROPHORE WITH TUNABLE PROPERTIES BETWEEN NEAR IR AND SWIR REGION FOR IN VIVO IMAGING

ACKNOWLEDGMENT OF GOVERNMENT SUPPORT

This invention was made with Government support under project number Z01BC011506 by the National Institutes of Health, National Cancer Institute. The Government has certain rights in the invention.

CROSS-REFERENCE TO RELATED APPLICATIONS

This is the U.S. National Stage of International Application No. PCT/US2019/047972, filed Aug. 23, 2019, which was published in English under PCT Article 21(2), which in turn claims the benefit of the earlier filing date of U.S. Provisional Application No. 62/721,986, filed Aug. 23, 2018, which is incorporated by reference herein in its entirety.

FIELD

Cyanine fluorophores with absorbance and emission maxima in the near-infrared and short wave infrared regions are disclosed, as well as methods of making and using the cyanine fluorophores.

BACKGROUND

The rapid proliferation of real time fluorescence guided surgery has underscored the necessity for novel fluorophore creation. Though used in many medical fields, fluorescence imaging is particularly useful in cancer treatment. Unlike conventional imaging tools like computed tomography (CT), positron emission tomography and magnetic resonance imaging (MRI), fluorescence imaging allows doctors to distinguish malignant from normal tissues with remarkable accuracy. While biological systems possess molecules that absorb in the visible region, molecules that absorb in the near infrared (NIR) region (650-900 nm) are far less abundant, allowing photons to penetrate up to several centimeters through tissue. While current surgical techniques rely on NIR light, where, due to light scattering effect, the image resolution and tissue penetration is limited, longer wavelengths such as SWIR (~900 to 1700 nm) can dramatically improve (>100x) spatial resolution by enhancing tissue penetration. However, studies in this area have typically used carbon nanotubes, Ag/In quantum dots, or nano-particles, which, due to safety concerns, will be difficult to translate into in vivo settings. Commercially available NIR dyes only possess emission maxima up to 800 nm. As such, there is a considerable need for bathochromic shifted NIR dyes that advance the scope of NIR fluorescence technology.

SUMMARY

Cyanine fluorophores including a nine-carbon polymethine bridge are disclosed. The cyanine fluorophores have absorbance and/or emission maxima in the near-infrared (NIR) and short-wave infrared (SWIR) wavelength ranges. Methods of making and using the cyanine fluorophores are also disclosed.

In some embodiments, a cyanine fluorophore compound has a chemical structure according to Formula I, or a stereoisomer or pharmaceutically acceptable salt thereof:

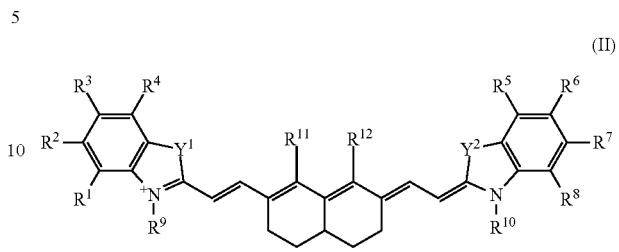

(II)

wherein $R^1$-$R^8$ independently are H, sulfonate, —$N(R^a)_2$, aliphatic, heteroaliphatic, aliphatic sulfonate, aminoaliphatic, —$C(O)OR^a$, trityl, deuterium, or a group comprising a conjugatable moiety, a targeting agent, or a drug, where each $R^a$ independently is H, aliphatic, heteroaliphatic, or deuterium; $R^9$ and $R^{10}$ independently are aliphatic sulfonate, —$(CH_2CH_2O)_nR^b$, aliphatic, aminoaliphatic, or alkoxy, where n is an integer ≥1 and $R^b$ is aliphatic, H, or deuterium; $R^{11}$ and $R^{12}$ together with the rings to which they are attached form a fused ring system, or $R^{11}$ and $R^{12}$ independently are halo, H, deuterium, or a group comprising a conjugatable moiety, a targeting agent, or a drug; and $Y^1$ and $Y^2$ independently are $C(R^c)_2$, O, $N(R^d)$, S, or Se, wherein each $R^c$ independently is aliphatic, H, —$(OCH_2CH_2)_xOH$ where x is an integer ≥2, trityl, deuterium, or a group comprising a conjugatable moiety, a targeting agent, or a drug, and each $R^d$ independently is H, aliphatic, heteroaliphatic, or deuterium.

In certain embodiments, the cyanine fluorophore compound has a chemical structure according to Formula II, Formula III, Formula IV, Formula V, or a stereoisomer or pharmaceutically acceptable salt thereof:

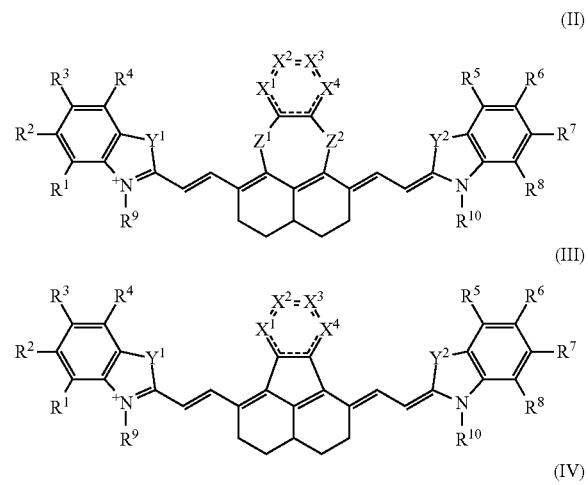

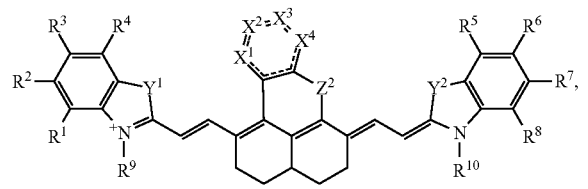

-continued

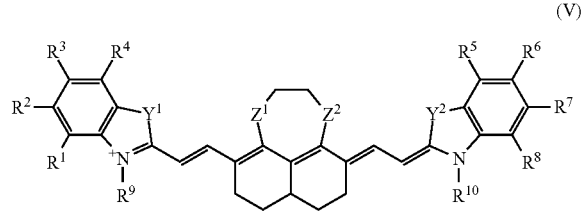

(V)

wherein each bond depicted as "-----" is a single or double bond as needed to satisfy valence requirements; $Z^1$ and $Z^2$ independently are O, S, or $N(R^d)$ where $R^d$ is H, aliphatic, heteroaliphatic, or deuterium; $X^1$-$X^4$ independently are $CR^{13}$, or one of $X^1$-$X^4$ is O and the others of $X^1$-$X^4$ are $CR^{13}$; and each $R^{13}$ independently is H, sulfonate, —$(CH_2)_m$C(O)$R^e$, —$(CH_2)_m$OC(O)$R^e$, —$N(R^a)_2$, aliphatic, heteroaliphatic, aliphatic sulfonate, aminoaliphatic, trityl, deuterium, or a group comprising a conjugatable moiety, a targeting agent, or a drug, where m is an integer ≥0, and $R^e$ is —$OR^a$ or —$N(R^f)_2$, where each $R^f$ independently is H, aliphatic, aliphatic sulfonate, —$(CH_2)_nC(O)OR^a$, —$(CH_2CH_2O)_nCH_2C(O)OR^a$, aryl, heteroaliphatic, or deuterium, where n is an integer ≥1.

In any or all of the above embodiments, the cyanine fluorophore, when dissolved in phosphate buffered solution (PBS) pH 7.4, 10% (v/v) fetal bovine serum in PBS pH 7.4, dichloromethane, or methanol, may have (i) an absorbance maximum wavelength ≥650 nm, (ii) an emission maximum wavelength ≥700 nm, or (iii) an absorbance maximum wavelength ≥650 nm and an emission maximum wavelength ≥700 nm.

Embodiments of a method for using the disclosed cyanine fluorophore compounds include combining the compound with a sample; and visualizing the compound in the sample by irradiating the sample with targeted application of a quantity of light having a wavelength in the near-infrared or short wave infrared range and a selected intensity, wherein the quantity of light is sufficient to produce fluorescence of the compound, and detecting any fluorescence emitted by the compound. In some embodiments, at least one of $R^1$-$R^{13}$ comprises a targeting agent, the sample comprises a target capable of binding with the targeting agent, and the method further includes combining the compound with the sample under conditions effective to provide binding of the targeting agent and the target; and imaging the target by visualizing the compound bound to the target.

In any or all of the foregoing embodiments, the sample may be a target area within a subject, and the method may further include administering the compound, or a pharmaceutical composition comprising the compound, to the subject; subsequently visualizing the compound by irradiating the compound by targeted application of the quantity of light to a targeted portion of the subject; and detecting any fluorescence emitted by the compound in the targeted portion of the subject.

The foregoing and other objects, features, and advantages of the invention will become more apparent from the following detailed description, which proceeds with reference to the accompanying figures.

BRIEF DESCRIPTION OF THE DRAWINGS

FIGS. 1A-1I are a table of exemplary cyanine fluorophores and their associated properties.

DETAILED DESCRIPTION

Figure 1F:
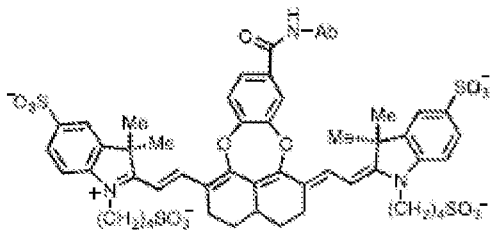
Figure 1F:
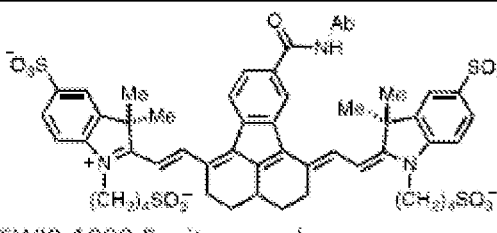
Figure 1F:
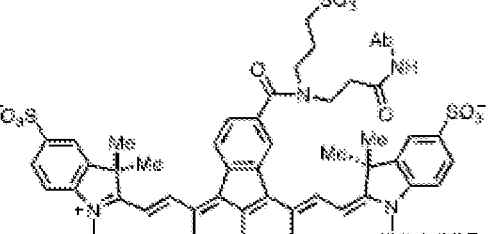
Figure 1G:
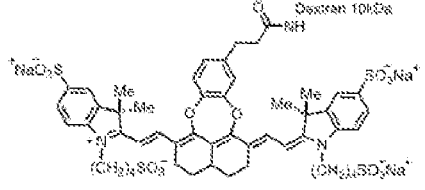
Figure 1G:
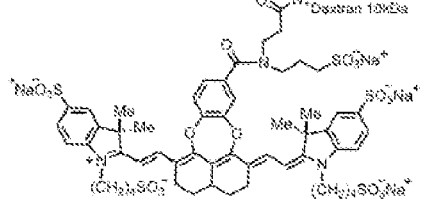
Figure 1G:
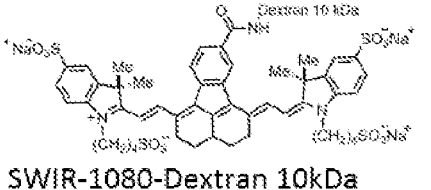
Figure 1G:
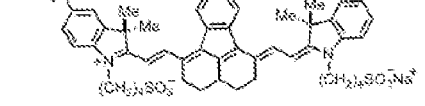
Figure 1G:
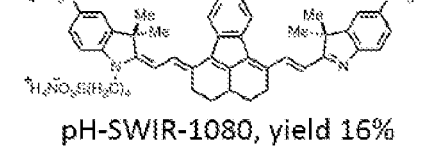
Figure 1G:
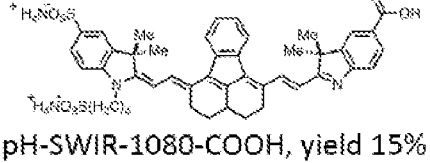
Figure 1G:
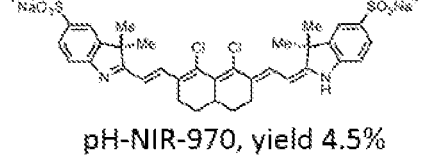
Figure 1H:
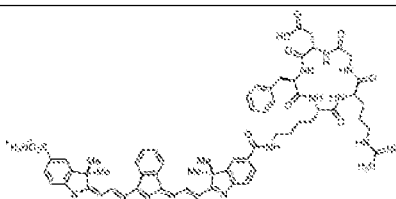
Figure 1H:
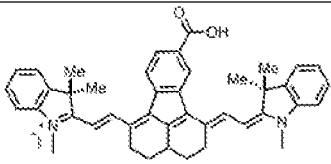
Figure 1H:
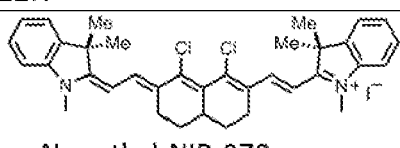
Figure 1H:
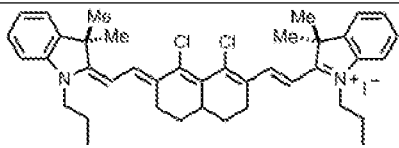
Figure 1H:
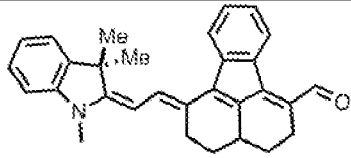
Figure 1H:
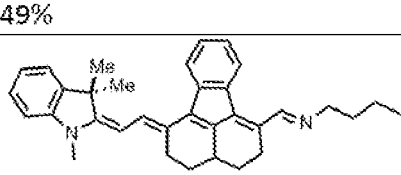
Figure 1H:
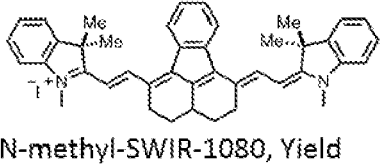

This disclosure concerns cyanine fluorophores with absorbance and/or emission maxima in the near-infrared (NIR) and short-wave infrared (SWIR) wavelength ranges. Compared to fluorophores that absorb and emit light at shorter wavelengths, some embodiments of the disclosed cyanine fluorophores provide improved (e.g., up to 100× or more) spatial resolution by enhancing tissue penetration. Advantageously, some embodiments of the disclosed cyanine fluorophores are nontoxic, aqueous-soluble, and/or non-aggregating. This disclosure also encompasses conjugatable cyanine fluorophores as well as cyanine fluorophores conjugated to targeting agents and/or drugs.

I. DEFINITIONS AND ABBREVIATIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Definitions of common terms in chemistry may be found in Richard J. Lewis, Sr. (ed.), *Hawley's Condensed Chemical Dictionary*, published by John Wiley & Sons, Inc., 1997 (ISBN 0-471-29205-2). Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

In order to facilitate review of the various embodiments of the disclosure, the following explanations of specific terms are provided:

Aliphatic: A substantially hydrocarbon-based compound, or a radical thereof (e.g., $C_6H_{13}$, for a hexane radical), including alkanes, alkenes, alkynes, including cyclic versions thereof, and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms. The term "lower aliphatic" refers to an aliphatic group containing from one to ten carbon atoms. An aliphatic chain may be substituted or unsubstituted. Unless expressly referred to as an "unsubstituted aliphatic," an aliphatic group can either be unsubstituted or substituted. An aliphatic group can be substituted with one or more substituents (up to two substituents for each methylene carbon in an aliphatic chain, or up to one substituent for each carbon of a —C═C— double bond in an aliphatic chain, or up to one substituent for a carbon of a terminal methine group). Exemplary substituents include, but are not limited to, alkyl, alkenyl, alkynyl, alkoxy, alkylamino, alkylthio, acyl, aldehyde, amide, amino, aminoalkyl, aryl, arylalkyl, carboxyl, cyano, cycloalkyl, dialkylamino, halo, haloaliphatic, heteroaliphatic, heteroaryl, heterocycloaliphatic, hydroxyl, oxo, sulfonamide, sulfhydryl, thioalkoxy, or other functionality.

Aliphatic sulfonate: A group having the structure —R—$SO_3^-$, where R is a substituted or unsubstituted aliphatic Alkoxy: A group having the structure —OR, where R is a substituted or unsubstituted alkyl. Methoxy (—$OCH_3$) is an exemplary alkoxy group. In a substituted alkoxy, R is alkyl substituted with a non-interfering substituent.

Alkyl: A hydrocarbon group having a saturated carbon chain. The chain may be branched, unbranched, or cyclic (cycloalkyl). The term lower alkyl means the chain includes 1-10 carbon atoms. Unless otherwise specified, the term alkyl encompasses substituted and unsubstituted alkyl.

Alkyl sulfonate: A group having the structure —R—SO$_3^-$, where R is a substituted or unsubstituted alkyl.

Amino: A group having the structure —N(R)R' where R and R' are independently hydrogen, haloalkyl, aliphatic, heteroaliphatic, aryl (such as optionally substituted phenyl or benzyl), heteroaryl, alkylsulfano, or other functionality. A "primary amino" group is —NH$_2$. "Mono-substituted amino" means a radical —N(H)R substituted as above and includes, e.g., methylamino, (1-methylethyl)amino, phenylamino, and the like. "Di-substituted amino" means a radical —N(R)R' substituted as above and includes, e.g., dimethylamino, methylethylamino, di(1-methylethyl)amino, and the like. The term amino also encompasses charged tri-substituted amino groups, e.g., —N(R)(R')R''$^+$ where R, R', and R'' are independently hydrogen, haloalkyl, aliphatic, heteroaliphatic, aryl (such as optionally substituted phenyl or benzyl), heteroaryl, alkylsulfano, or other functionality.

Aminoaliphatic: A chemical functional group —RNH$_2$ or —RNH$_3^+$ where R is an aliphatic group. "Substituted amino aliphatic" means that the amino group is substituted, e.g., —RN(R')R'' or —RN(R')(R'')R'''$^+$ where R', R'', and R''' are independently hydrogen, haloaliphatic, aliphatic, heteroaliphatic, aryl (such as optionally substituted phenyl or benzyl), heteroaryl, alkylsulfano, or other functionality.

Aminoalkyl: A chemical functional group —RNH$_2$ or —RNH$_3^+$ where R is an alkyl group. "Substituted aminoalkyl" means that the amino group is substituted, e.g., —RN(R')R'' or —RN(R')(R'')R'''$^+$ where R', R'', and R''' are independently hydrogen, haloaliphatic, aliphatic, heteroaliphatic, aryl (such as optionally substituted phenyl or benzyl), heteroaryl, alkylsulfano, or other functionality.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. In avian and reptilian species, IgY antibodies are equivalent to mammalian IgG.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" (V$_L$) and "variable heavy chain" (V$_H$) refer, respectively, to these light and heavy chains.

The structure of IgY antibodies is similar to the structure of mammalian IgG, with two heavy ("nu" chains; approximately 67-70 kDa) and two light chains (22-30 kDa). The molecular weight of an IgY molecule is about 180 kDa, but it often runs as a smear on gels due to the presence of about 3% carbohydrate. Heavy chains (H) of IgY antibodies are composed of four constant domains and one variable domain, which contains the antigen-binding site.

As used herein, the term "antibodies" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999). As used herein, the term "antibodies" includes antibodies comprising one or more unnatural (i.e., non-naturally occurring) amino acids (e.g., p-acetyl-phenyl-alanine) to facilitate site-specific conjugation.

Antibodies for use in the methods of this disclosure can be monoclonal or polyclonal, and for example specifically bind a target such as the target antigen. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. As used herein, a "target antigen" is an antigen (including an epitope of the antigen) that is recognized and bound by a targeting agent. "Specific binding" does not require exclusive binding. In some embodiments, the antigen is obtained from a cell or tissue extract. In some embodiments, the target antigen is an antigen on a tumor cell. An antigen need not be a full-length protein. Antigens contemplated for use include any immunogenic fragments of a protein, such as any antigens having at least one epitope that can be specifically bound by an antibody.

Aryl: A monovalent aromatic carbocyclic group of, unless specified otherwise, from 6 to 15 carbon atoms having a single ring (e.g., phenyl) or multiple condensed rings in which at least one ring is aromatic (e.g., quinoline, indole, benzodioxole, and the like), provided that the point of attachment is through an atom of an aromatic portion of the aryl group and the aromatic portion at the point of attachment contains only carbons in the aromatic ring. If any aromatic ring portion contains a heteroatom, the group is a heteroaryl and not an aryl. Aryl groups are monocyclic, bicyclic, tricyclic or tetracyclic. Unless otherwise specified, the term aryl encompasses substituted and unsubstituted aryl.

Biological sample: As used herein, a "biological sample" refers to a sample obtained from a subject (such as a human or veterinary subject) or other type of organism, such as a plant, bacteria or insect. Biological samples from a subject include, but are not limited to, cells, tissue, serum, blood, plasma, urine, saliva, cerebral spinal fluid (CSF) or other bodily fluid. In particular examples of the method disclosed herein, the biological sample is a tissue sample.

Conjugatable moiety: A portion of a molecule that allows the molecule to be conjugated (i.e., coupled or bound) to another molecule, e.g., to a drug or targeting agent such as an antibody.

dSTORM: Direct stochastic optical reconstruction microscopy.

Drug: As used herein, the term "drug" refers to a substance which has a physiological effect when administered to a subject, and is intended for use in the treatment, mitigation, cure, prevention, or diagnosis of disease or used to otherwise enhance physical or mental well-being. The term "small molecule drug" refers to a drug having a molecular weight <1,000 Daltons.

An anti-cancer drug is a drug that is used to treat malignancies. Exemplary anti-cancer drugs include, but are not limited to, abiraterone, actinomycin D, altretamine, amifostine, anastrozole, asparaginase, bexarotene, bicalutamide, bleomycin, buserelin, busulfan, carboplatin, carmustine, chlorambucil cisplatin, cladribine, clodronate, combretastatin A4, cyclophosphamide, cyproterone, cytarabine, dacarbazine, daunorubicin, degarelix, diethylstilbestrol, docetaxel, doxorubicin, duocarmycin DM, epirubicin, ethinyl estradiol, etoposide, exemestane, 5-fluorouracil, fludarabine, flutamide, folinic acid, fulvestrant, gemcitabine, goserelin, ibandronic acid, idarubicin, ifosfamide, irinotecan, lanreotide, lenalidomide, letrozole, leuprorelin, medroxyprogesterone, megestrol, melphalan, mesna, methotrexate, octreotide, pamidronate, pemetrexed, mitocmycin, mitotane, mitoxantrone, oxaliplatin, paclitaxel, pentastatin, pipbroman, plicamycin, procarbazine, raltitrexed, stilbestrol, streptozocin, tamoxifen, temozolomide, teniposide, topotecan, triptorelin, vinblastine, vincristine, vinorelbine, and zolendronic acid.

Effective amount or therapeutically effective amount: An amount sufficient to provide a beneficial, or therapeutic, effect to a subject or a given percentage of subjects.

Far-red: Far red light is generally considered to be light is a wavelength within a range of 700-850 nm.

Heteroaliphatic: An aliphatic compound or group having at least one heteroatom, i.e., one or more carbon atoms has been replaced with an atom having at least one lone pair of electrons, typically nitrogen, oxygen, phosphorus, silicon, or sulfur. Heteroaliphatic compounds or groups may be substituted or unsubstituted, branched or unbranched, cyclic or acyclic, and include "heterocycle", "heterocyclyl", "heterocycloaliphatic", or "heterocyclic" groups.

Heteroalkyl: An alkyl group as defined above containing at least one heteroatom, such as N, O, S, or $S(O)_n$. (where n is 1 or 2). Unless otherwise specified, the term heteroalkyl encompasses substituted and unsubstituted heteroalkyl.

Heteroaryl: An aromatic compound or group having at least one heteroatom, i.e., one or more carbon atoms in the ring has been replaced with an atom having at least one lone pair of electrons, typically nitrogen, oxygen, phosphorus, silicon, or sulfur. Unless otherwise specified, the term heteroaryl encompasses substituted and unsubstituted heteroaryl.

Ligand: A molecule that binds to a receptor, having a biological effect.

Linker: A molecule or group of atoms positioned between two moieties. As used herein, the term "linker" refers to a group of atoms positioned between the cyanine fluorophore and a targeting agent or reactive group, or to a group of atoms positioned between the cyanine fluorophore and a drug.

Molar absorptivity ($\varepsilon$): A measure of how strongly a chemical species absorbs light at a particular wavelength, typically expressed in units of $M^{-1}cm^{-1}$. The values reported herein were obtained at the wavelength of maximum absorbance.

Near-infrared (near-IR, NIR): Wavelengths within the range of 650-2500 nm. Unless otherwise specified, the terms "near-infrared" and "NIR" as used herein refer to wavelengths within the range of 650-900 nm.

PALM: Photo-activated localization microscopy.

PBS: Phosphate-buffered solution. Most commonly PBS refers to an aqueous solution including 0.01 M $Na_2HPO_4$, 0.0018 M $KH_2PO_4$, 0.137 M NaCl, and 0.0027 M KCl.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., $21^{st}$ Edition (2005), describes compositions and formulations suitable for pharmaceutical delivery of one or more cyanine fluorophores as disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutically acceptable salt: A biologically compatible salt of a disclosed cyanine fluorophores, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. Pharmaceutically acceptable acid addition salts are those salts that retain the biological effectiveness of the free bases while formed by acid partners that are not biologically or otherwise undesirable, e.g., inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Pharmaceutically acceptable base addition salts include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19, which is incorporated herein by reference.)

Phosphoramidite: A group having the general formula $(RO)_2PNR_2$. As a substituent, a phosphoramidite has a general formula —RO—P(OR)NR$_2$ where each R independently is aliphatic, such as substituted or unsubstituted alkyl.

Short wave infrared (SWIR): Unless otherwise specified, as used herein the term "short wave infrared" or SWIR refers to wavelengths within the range of 900-1700 nm.

SMLM: Single-molecule localization microscopy.

Soluble: Capable of becoming molecularly or ionically dispersed in a solvent to form a homogeneous solution. As defined, by the U.S. Pharmacopeia, a soluble compound has a solubility of at least 30 mg/mL.

Specific binding partner: A member of a pair of molecules that interact by means of specific, non-covalent interactions that depend on the three-dimensional structures of the molecules involved. Exemplary pairs of specific binding partners include antigen/antibody, hapten/antibody, receptor/ligand, nucleic acid strand/complementary nucleic acid strand, substrate/enzyme, inhibitor/enzyme, carbohydrate/lectin, biotin/avidin (such as biotin/streptavidin), and virus/cellular receptor.

STORM: Stochastic optical reconstruction microscopy.

Substituent: An atom or group of atoms that replaces another atom in a molecule as the result of a reaction. The term "substituent" typically refers to an atom or group of atoms that replaces a hydrogen atom, or two hydrogen atoms if the substituent is attached via a double bond, on a parent hydrocarbon chain or ring. The term "substituent" may also cover groups of atoms having multiple points of attachment to the molecule, e.g., the substituent replaces two or more hydrogen atoms on a parent hydrocarbon chain or ring. In such instances, the substituent, unless otherwise specified, may be attached in any spatial orientation to the parent hydrocarbon chain or ring. Exemplary substituents include, for instance, alkyl, alkenyl, alkynyl, alkoxy, alkylamino, alkylthio, acyl, aldehyde, amido, amino, aminoalkyl, aryl, arylalkyl, arylamino, carbonate, carboxyl, cyano, cycloalkyl, dialkylamino, halo, haloaliphatic (e.g., haloalkyl), haloalkoxy, heteroaliphatic, heteroaryl, heterocycloaliphatic, hydroxyl, isocyano, isothiocyano, oxo, sulfonamide, sulfhydryl, thio, and thioalkoxy groups.

Substituted: A fundamental compound, such as an aryl or aliphatic compound, or a radical thereof, having coupled thereto one or more substituents, each substituent typically replacing a hydrogen atom on the fundamental compound. Solely by way of example and without limitation, a substituted aryl compound may have an aliphatic group coupled to the closed ring of the aryl base, such as with toluene. Again solely by way of example and without limitation, a long-chain hydrocarbon may have a hydroxyl group bonded thereto.

Sulfonate-containing group: A group including $SO_3^-$. The term sulfonate-containing group includes —$SO_3^-$ and —$RSO_3^-$ groups, where R is substituted or unsubstituted alkyl, substituted or unsubstituted heteroalkyl, substituted or unsubstituted aryl, or substituted or unsubstituted heteroaryl.

Target: An intended molecule to which a disclosed cyanine fluorophore comprising a targeting agent is capable of specifically binding. Examples of targets include proteins and nucleic acid sequences present in tissue samples. A target area is an area in which a target molecule is located or potentially located.

Targeting agent: An agent that promotes preferential or targeted delivery to a target site, for example, a targeted location in a subject's body, such as a specific organ, organelle, physiologic system, tissue, or site of pathology such as a tumor, area of infection, or area of tissue injury. Targeting agents function by a variety of mechanisms, such as selective concentration in a target site or by binding to a specific binding partner. Suitable targeting agents include, but are not limited to, proteins, polypeptides, peptides, glycoproteins and other glycoslyated molecules, oligonucleotides, phospholipids, lipoproteins, alkaloids, and steroids. Exemplary targeting agents include antibodies, antibody fragments, affibodies, aptamers, albumin, cytokines, lymphokines, growth factors, hormones, enzymes, immune modulators, receptor proteins, antisense oligonucleotides, avidin, nano particles, and the like. Particularly useful of targeting agents are antibodies, nucleic acid sequences, and receptor ligands, although any pair of specific binding partners can be readily employed for this purpose.

TRABI: Temporal, radial-aperture-based intensity estimation.

Treat/treatment: As used herein, the terms "treat" and "treatment" mean to inhibit or reduce at least one sign or symptom associated with a condition, i.e., a disorder or disease. With respect to a tumor, treating may mean inhibiting tumor growth and/or reducing a tumor volume. Treatment may, for example, produce a reduction in severity of some or all clinical symptoms of the tumor, a slower progression of the tumor (for example by prolonging the life of a subject having the tumor), a reduction in the number of tumor reoccurrence, an improvement in the overall health or well-being of the subject, or by other parameters well known in the art that are specific to the particular disorder or disease.

Trityl: A substituted or unsubstituted triphenyl methyl group, e.g., Ph$_3$C—OR— or Ph$_3$CR— where R is aliphatic. Each phenyl group and R independently may be substituted or unsubstituted.

II. CYANINE FLUOROPHORES

Embodiments of the disclosed cyanine fluorophores include a nine-carbon polymethine bridge. In some embodiments, a cyanine fluorophore has a chemical structure according to Formula I, or a stereoisomer or pharmaceutically acceptable salt thereof:

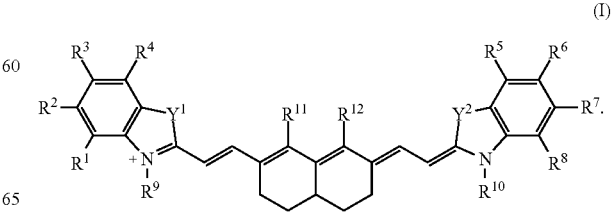

(I)

With respect to Formula I, $R^1$-$R^8$ independently are H, sulfonate, —$N(R^a)_2$, aliphatic, heteroaliphatic, aliphatic sulfonate, aminoaliphatic, —$C(O)OR^a$, trityl, deuterium, or a group comprising a conjugatable moiety, a targeting agent, or a drug, where each $R^a$ independently is H, aliphatic, heteroaliphatic, or deuterium. $R^9$ and $R^{10}$ independently are aliphatic sulfonate, —$(CH_2CH_2O)_nR^b$, aliphatic, aminoaliphatic, or alkoxy, where n is an integer ≥1 and $R^b$ is aliphatic, H, or deuterium. $R^{11}$ and $R^{12}$ together with the rings to which they are attached form a fused ring system, or $R^{11}$ and $R^{12}$ independently are halo, H, deuterium, or a group comprising a conjugatable moiety, a targeting agent, or a drug. $Y^1$ and $Y^2$ independently are $C(R^c)_2$, O, $N(R^d)$, S, or Se, wherein each $R^c$ independently is aliphatic, H, —$(OCH_2CH_2)_xOH$ where x is an integer ≥2, trityl, deuterium, or a group comprising a conjugatable moiety, a targeting agent, or a drug, and each $R^d$ independently is H, aliphatic, heteroaliphatic, or deuterium. In some examples, the trityl group has a formula —$(CH_2)_3OC(Ph_2)$(p-methoxyphenyl).

In some embodiments, $R^1$-$R^8$ independently are H, sulfonate, —$N(R^a)_2$, alkyl, heteroalkyl, alkyl sulfonate, aminoalkyl, —$C(O)OR^a$, trityl, or a group comprising a conjugatable moiety, a targeting agent, or a drug, where each $R^a$ independently is H, alkyl, or heteroalkyl. $R^9$ and $R^{10}$ independently are alkyl sulfonate, —$(CH_2CH_2O)_nR^b$, alkyl, aminoalkyl, or alkoxy, where n is an integer ≥1 and $R^b$ is alkyl or H. $R^{11}$ and $R^{12}$ together with the rings to which they are attached form a fused ring system, or $R^{11}$ and $R^{12}$ are halo, H, or a group comprising a conjugatable moiety, a targeting agent, or a drug. $Y^1$ and $Y^2$ independently are $C(R^c)_2$, O, $N(R^d)$, S, or Se, wherein each $R^c$ independently is alkyl, H, —$(OCH_2CH_2)_xOH$ where x is an integer ≥2, trityl, or a group comprising a conjugatable moiety, a targeting agent, or a drug, and each $R^d$ independently is H, alkyl, or heteroalkyl.

In any of the disclosed embodiments, an alkyl group or alkyl moiety of an alkyl sulfonate or aminoalkyl group may be lower alkyl ($C_1$-$C_{10}$ alkyl), $C_1$-$C_5$ alkyl, $C_1$-$C_3$ alkyl, methyl, ethyl, $C_3$ alkyl, $C_4$ alkyl, $C_5$ alkyl, $C_6$ alkyl, $C_7$ alkyl, $C_8$ alkyl, $C_9$ alkyl, or $C_{10}$ alkyl. A heteroalkyl group may have a chain length, including carbon atoms and heteroatoms, of from 2-10, 2-5, or 2-3, such as a chain length of 2, 3, 4, 5, 6, 7, 8, 9, or 10.

In any or all of the above embodiments, (i) $R^3$ and $R^6$ may be sulfonate, (ii) $R^1$, $R^2$, $R^4$, $R^5$, $R^7$, and $R^8$ may be H, or (iii) both (i) and (ii). In any or all of the above embodiments, (i) $R^9$ and $R^{10}$ independently may be $C_1$-$C_{10}$ alkyl sulfonate; (ii) $R^9$ and $R^{10}$ may be —$(CH_2CH_2O)_nR^b$ where each n independently is 1, 2, 3, 4, 5, 6, 7, 8, 9, or 10, and each $R^b$ independently is $C_1$-$C_3$ alkyl or H; or (iii) $R^9$ and $R^{10}$ independently may be $C_1$-$C_{20}$ alkyl. In one embodiment, $R^9$ and $R^{10}$ are $C_3$-$C_5$ sulfonate. In some non-limiting examples, $R^9$ and $R^{10}$ are —$(CH_2)_4SO_3^-$. In an independent embodiment, $R^9$ and $R^{10}$ are —$(CH_2CH_2O)_nR^b$ where n is 2, 3, or 4, and each $R^b$ independently is $C_1$-$C_3$ alkyl or H. In some non-limiting examples, $R^9$ and $R^{10}$ are —$(CH_2CH_2O)_3CH_3$. In another independent embodiment, $R^9$ and $R^{10}$ are $C_1$-$C_5$ alkyl. In yet another independent embodiment, $R^9$ and $R^{10}$ are $C_{15}$-$C_{20}$ alkyl.

In any or all of the above embodiments, $Y^1$ and $Y^2$ independently are $C(R^c)_2$, O, $N(R^d)$, S, or Se. In some embodiments, (i) $Y^1$ and $Y^2$ are $C(R^c)_2$ where each $R^c$ is $C_1$-$C_3$ alkyl, (ii) $Y^1$ and $Y^2$ are $C(R^c)_2$ where at least one $R^c$ is a group comprising a conjugatable moiety, a targeting agent, or a drug, or (iii) $Y^1$ and $Y^2$ are O. In one embodiment, $Y^1$ and $Y^2$ are $C(CH_3)_2$. In an independent embodiment, $Y^1$ is $C(CH_3)(R^c)$ where $R^c$ is a group comprising a conjugatable moiety, a targeting agent, or a drug, and $Y^2$ is $C(CH_3)_2$ or $C(CH_3)$trityl. In another independent embodiment, $Y^2$ is $C(CH_3)(R^c)$ where $R^c$ is a group comprising a conjugatable moiety, a targeting agent, or a drug, and $Y^1$ is $C(CH_3)_2$ or $C(CH_3)$trityl. In still another independent embodiment, $Y^1$ and $Y^2$ are O.

In any or all of the above embodiments, $R^{11}$ and $R^{12}$ together with the rings to which they are attached may form a fused ring system. In some embodiments, the resulting compound has a chemical structure according to Formula II, Formula III, Formula IV, Formula V, or a stereoisomer or pharmaceutically acceptable salt thereof:

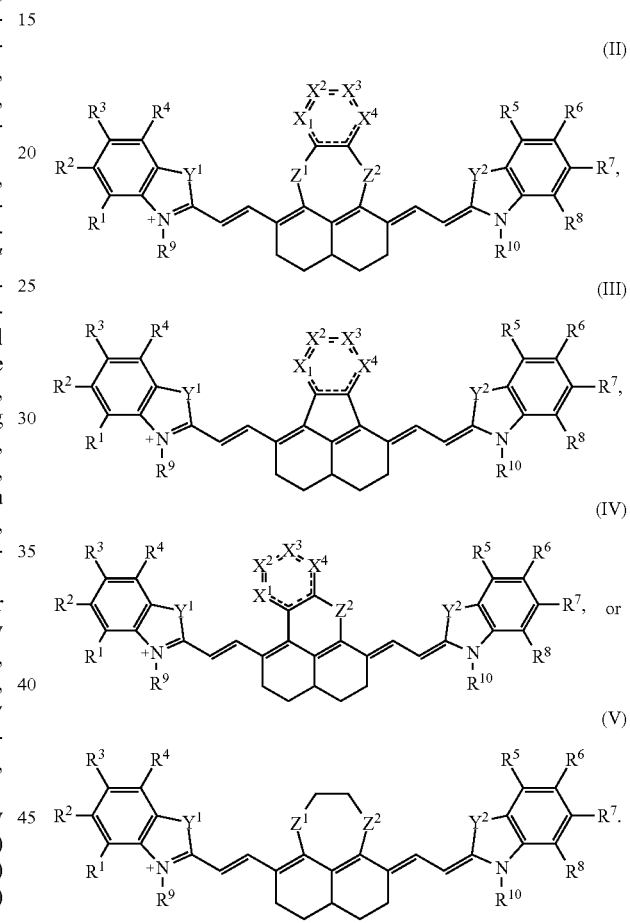

With respect to Formulas II-V, each bond depicted as "===" is a single or double bond as needed to satisfy valence requirements. $Z^1$ and $Z^2$, when present, independently are O, S, or $N(R^d)$ where $R^d$ is H, aliphatic, heteroaliphatic, or deuterium. $X^1$-$X^4$ independently are $CR^{13}$, or one of $X^1$-$X^4$ is O and the others of $X^1$-$X^4$ are $CR^{13}$. Each $R^{13}$ independently is H, sulfonate, —$(CH_2)_mC(O)R^e$, —$(CH_2)_mOC(O)R^e$, —$N(R^a)_2$, aliphatic, heteroaliphatic, aliphatic sulfonate, aminoaliphatic, trityl, deuterium, or a group comprising a conjugatable moiety, a targeting agent, or a drug, where m is an integer ≥0, and $R^e$ is —$OR^a$ or —$N(R^f)_2$, where $R^a$ is as previously defined and each $R^f$ independently is H, aliphatic, aliphatic sulfonate, —$(CH_2)_nC(O)OR^a$, —$(CH_2CH_2O)_nCH_2C(O)OR^a$, aryl, heteroaliphatic, or deuterium, where n is an integer ≥1.

In some embodiments, $Z^1$ and $Z^2$, when present, independently are O, S, or $N(R^d)$ where $R^d$ is H, alkyl, or heteroalkyl. $X^1$-$X^4$ independently are $CR^{13}$, or one of $X^1$-$X^4$ is O and the others of $X^1$-$X^4$ are $CR^{13}$. Each $R^{13}$ independently is H, sulfonate, —$(CH_2)_mC(O)R^e$, —$(CH_2)_mOC(O)R^e$, —$N(R^a)_2$, alkyl, heteroalkyl, alkyl sulfonate, aminoalkyl, trityl, or a group comprising a conjugatable moiety, a targeting agent, or a drug, where m is an integer ≥0, and $R^e$ is —$OR^a$ or —$N(R^f)_2$, and each $R^f$ independently is H, alkyl, alkyl sulfonate, —$(CH_2)_nC(O)OR^a$, —$(CH_2CH_2O)_nCH_2C(O)OR^a$, aryl, or heteroalkyl, where n is an integer ≥1.

In any or all of the above embodiments, the compound may have a structure according to Formula II where $Z^1$ and $Z^2$ are O. In an independent embodiment, the compound has a structure according to Formula II and $Z^1$ and $Z^2$ are S.

In any or all of the above embodiments, the compound may have a structure according to Formula IV, where $Z^2$ is O. In still another independent embodiment, the compound has a structure according to Formula IV, and $Z^2$ is S.

In any or all of the above embodiments, the compound may have a structure according to Formula V, where $Z^1$ is $N(R^d)$ and $Z^2$ is O. In one embodiment, $Z^1$ is $N(CH_3)$ and $Z^2$ is O.

In any or all of the above embodiments, $X^1$-$X^4$ independently are $CR^{13}$, or one of $X^1$-$X^4$ is O and the others of $X^1$-$X^4$ are $CR^{13}$. Each $R^{13}$ independently is H, sulfonate, —$(CH_2)_mC(O)R^e$, —$(CH_2)_mOC(O)R^e$, —$N(R^a)_2$, aliphatic, heteroaliphatic, aliphatic sulfonate, aminoaliphatic, trityl, deuterium, or a group comprising a conjugatable moiety, a targeting agent, or a drug. In some embodiments, each $R^{13}$ independently is H, sulfonate, —$(CH_2)_mC(O)R^e$, —$N(R^a)_2$, alkyl, heteroalkyl, alkyl sulfonate, aminoalkyl, trityl, deuterium, or a group comprising a conjugatable moiety, a targeting agent, or a drug. In one embodiment, one of $X^1$-$X^4$ is $CR^{13}$ where $R^{13}$ is a group comprising a conjugatable moiety, a targeting agent, or a drug, and the others of $X^1$-$X^4$ are CH. In an independent embodiment, one of $X^2$ and $X^3$ is C—$(CH_2)_mC(O)R^e$, the other of $X^2$ and $X^3$ is CH, and $X^1$ and $X^4$ are CH. In another independent embodiment, either $X^2$ and $X^4$ are C-sulfonate and $X^1$ and $X^3$ are CH, or $X^1$ and $X^3$ are C-sulfonate and $X^2$ and $X^4$ are CH. Instill another independent embodiment, $X^1$-$X^4$ are CH. In another independent embodiment, one of $X^1$-$X^4$ is O and the others of $X^1$-$X^4$ are CH. In yet another independent embodiment, one of $X^1$-$X^4$ is O, another of $X^1$-$X^4$ is $CR^{13}$ where $R^{13}$ is a group comprising a conjugatable moiety, a targeting agent, or a drug, and the others of $X^1$-$X^4$ are CH.

In any or all of the above embodiments, at least one of $R^1$-$R^8$ or $R^{13}$ may be a group comprising a conjugatable moiety, a targeting agent, or a drug, or at least one of $Y^1$ and $Y^2$ may $C(R^c)_2$ where one $R^c$ is a group comprising a conjugatable moiety, a targeting agent, or a drug.

Groups comprising conjugatable moieties or targeting agents have a formula -$L_1$-$R^g$ where $R^g$ is a conjugatable moiety or targeting agent. $L_1$ is absent or a linker. Exemplary -$L_1$-$R^g$ groups include, but are not limited to, —$(CR'_2)_nR^g$, —$(CR'_2)_nC(O)N(R')R^g$, —$C(O)N(R')(CH_2)_nR^g$, —$(CR'2)_n$ $C(O)N(H)(CR'_2)_nR^g$, —$C(O)N(R')(CR'_2)_pN(R')C(O)(CR'_2)_n$ $R^g$, —$C(O)N(R')(CR'_2)_pN(R')C(O)(CR'_2)_nOR^g$, —$C(O)N(R')(CH_2CH_2O)_n(CR'_2)_nC(O)R^g$, —$C(O)N(R')(CH_2CH_2O)_n(CR'_2)_nC(O)N(R')R^g$, —$(CR'_2)_nC(O)R^g$, —$(CR'_2)_nN(R')R^g$, —$(CR'_2)_nN(R')C(O)R^g$, —$(CR'_2)_nC(O)SR^g$, —$C(O)R^g$, —$C(O)OR^g$, —$C(O)N(R')R^g$, —$N(R')C(O)R^g$, —$N(R')(CR'_2)_pC(O)R^g$, —$N(R')R^g$, —$OR^g$, or —$SR^g$ where each n independently is an integer ≥1, p is an integer ≥1, and each R' independently is H, halo, optionally substituted aliphatic, optionally substituted heteroaliphatic, optionally substituted aryl, optionally substituted heteroaryl, or deuterium, or $(CR'_2)_p$ collectively is aryl. In some embodiments, each R' independently is H, halo, or $C_1$-$C_5$ alkyl, and each n and each p independently is 1, 2, 3, 4, 5, 6, 7, 8, 9, or 10. In certain embodiments, each R' is H, and each n and each p independently is 1, 2, 3, 4, 5, 6, 7, 8, 9, or 10.

Conjugatable moieties are portions of a molecule that allow the molecule to be conjugated (i.e., coupled or bound) to another molecule, such as a targeting agent or drug. Conjugatable moieties include well-known amine- and thiol-reactive groups, as well as more recently developed moieties useful for "click chemistry" (pairs of functional groups that rapidly and selectively react ("click") with each other under mild conditions) such as copper-catalyzed azide-alkyne cycloaddition (CUAAC) or copper-free addition—a strain-promoted alkyne-azide cycloaddition (SPAAC). Suitable conjugatable moieties include, but are not limited to, N-hydroxysuccinimidyl groups, maleimidyl groups, alkenyl groups, alkynyl groups, azides, tetrazines, phosphoramidites, and combinations thereof. Exemplary alkynes include, but are not limited to, terminal alkynes, dibenzocyclooctyne (DBCO, DIBO), and bicyclo[6.1.0]nonyne (BCN). Exemplary alkenes include terminal alkenes, trans-cyclooctene (TCO), and methylcyclopropene. In some examples, the phosphoramidite has a formula —$(CH_2)_3OP$ $(O(CH_2)CN)(N(i\text{-}Pr)_2)$ where i-Pr is isopropyl. In certain embodiments, when the compound includes a phosphoramidite group on one half of the molecule, the compound may also include a trityl group on the other half of the molecule. For example, if $Y^1$ is substituted with a phosphoramidite group, then $Y^2$ may be substituted with a trityl group.

Exemplary targeting agents include, but are not limited to, antibodies, ligands, peptides, nucleic acid strands, polysaccharides, and the like. In one embodiment, the targeting agent is phalloidin, a bicyclic heptapeptide that binds to F-actin. In an independent embodiment, the targeting agent is an antibody. Exemplary antibodies include antibodies capable of recognizing and binding to a target molecule, such as a biomarker associated with a disease, infection, or environmental exposure. Biomarkers include, but are not limited to, proteins, peptides, lipids, metabolites, and nucleic acids. In some embodiments, the antibody is capable of recognizing and binding to a tumor biomarker, such as a protein only found in or on tumor cells or to a cell-surface receptor associated with one or more cancers. For example, panitumumab is a human monoclonal antibody that recognizes and binds to human epidermal growth factor receptor 1 (HER1); HER1 is overexpressed in numerous tumor types and is also associated with some inflammatory diseases. Trastuzumab and pertuzumab are monoclonal antibodies that bind to the HER2/neu receptor, which is over-expressed in some breast cancers. Brentuximab is a monoclonal antibody that targets a cell-membrane protein CD30, which is expressed in classical Hodgkin lymphoma and systemic anaplastic large cell lymphoma. In another independent embodiment, the targeting agent is an oligomer or polymer capable of binding to a target such as an antigen, a nucleic acid sequence, or the like. Exemplary oligomers and polymers include, but are not limited to, polysaccharides, peptides, and oligonucleotides. In one example, the polymer is dextran having a molecular weight within a range of 3-2000 kDa. Dextran is useful for bioimaging. For instance, cyanine fluorophore-labeled dextran may be used to monitor biological events of the cytoplasmic matrix.

Exemplary groups comprising a drug include, but are not limited to, groups having a formula -$L_2$-$C(O)$—$X^1$-drug, where $L_2$ is a linker moiety or is absent and $X^1$ is O, N(H), or N(CH$_3$). In one embodiment, L$_2$ is absent. In another embodiment, L$_2$ is O. In an independent embodiment, L$_2$ is aryl or heteroaryl substituted with at least one substituent comprising a substituted or unsubstituted aliphatic or heteroaliphatic moiety, wherein the aryl or heteroaryl ring is the site of attachment to the remainder of the conformationally restricted cyanine fluorophore and the substituent is bonded to the —C(O)—X$^1$-drug moiety. In some embodiments, the group comprising a drug is:

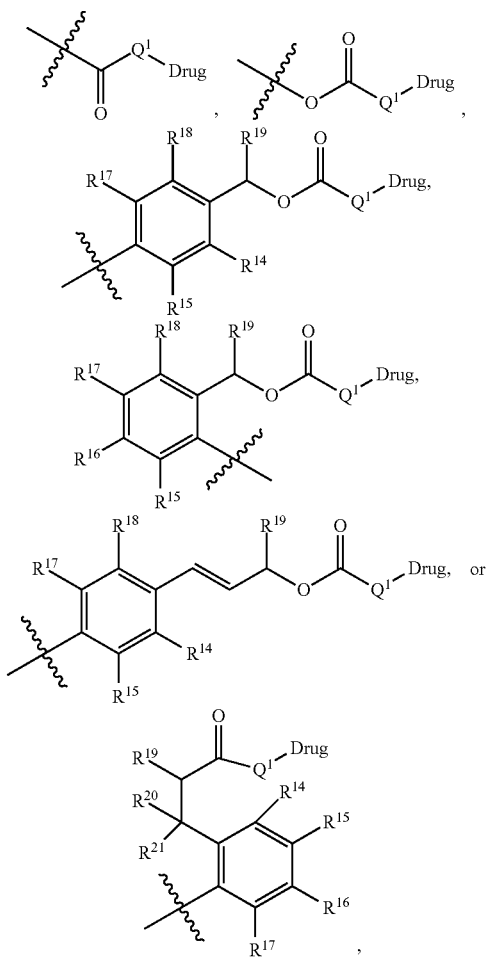

where Q$^1$ is O, N(H), or N(CH$_3$), and R$^{14}$-R$^{21}$ independently are H, alkyl, —NO$_2$, —NR$^h{}_2$, —NR$^h{}_3{}^+$, alkoxy, sulfonate, or deuterium, wherein each R$^h$ independently is H, halo, aliphatic, or deuterium. In some embodiments, each R$^h$ independently is H, halo, or alkyl. In certain embodiments, R$^{14}$-R$^{21}$ are H. In some examples, the group comprising a drug is —C(O)-Q$^1$-Drug. The drug can be any drug capable of conjugation to the remainder of the group. In some embodiments, the drug is a small-molecule drug, e.g., a drug having a molecular weight <1,000 Daltons. In certain embodiments, the drug moiety is an anti-cancer drug.

Some embodiments of the disclosed cyanine fluorophores exhibit an absorbance maximum, an emission maximum, or both within the near-infrared or short-wave infrared wavelength range. When dissolved in phosphate-buffered solution (PBS) pH 7.4, 10% (v/v) fetal bovine serum (FBS) in PBS pH 7.4, methanol, or dichloromethane, a cyanine fluorophore as disclosed herein may have an absorbance and/or emission maximum wavelength ≥650 nm, ≥700 nm, ≥750 nm, ≥800 nm, ≥850 nm, ≥875 nm, or ≥900 nm, such as an absorbance and/or emission maximum wavelength within a range of 650-1700 nm, 750-1700 nm, or 850-1700 nm. In one embodiment, the cyanine fluorophore has (i) an absorbance maximum wavelength ≥650 nm, (ii) an emission maximum wavelength ≥700 nm, or (iii) an absorbance maximum wavelength ≥650 nm and an emission maximum wavelength ≥700 nm. In an independent embodiment, the cyanine fluorophore has (i) an absorbance maximum wavelength ≥750 nm, (ii) an emission maximum wavelength ≥800 nm, or (iii) an absorbance maximum wavelength ≥750 nm and an emission maximum wavelength ≥800 nm. In another independent embodiment, the cyanine fluorophore has (i) an absorbance maximum wavelength ≥850 nm, (ii) an emission maximum wavelength ≥900 nm, or (iii) an absorbance maximum wavelength ≥850 nm and an emission maximum wavelength ≥900 nm. In still another independent embodiment, the cyanine fluorophore may have (i) an absorbance maximum wavelength ≥875 nm, (ii) an emission maximum wavelength ≥950 nm, or (iii) an absorbance maximum wavelength ≥875 nm and an emission maximum wavelength ≥950 nm. In yet another independent embodiment, the cyanine fluorophore may have (i) an absorbance maximum wavelength ≥900 nm, (ii) an emission maximum wavelength ≥1000 nm, or (iii) an absorbance maximum wavelength ≥900 nm and an emission maximum wavelength ≥1000 nm.

Embodiments of the disclosed cyanine fluorophores strongly absorb light having a wavelength within the NIR or SWIR range. In any or all of the above embodiments, a cyanine fluorophore as disclosed herein may have a molar absorptivity (ε) of at least 50,000 M$^{-1}$cm$^{-1}$. In some embodiments, the molar absorptivity is at least 75,000, at least 100,000, at least 125,000, or even at least 150,000 M$^{-1}$cm$^{-1}$, such as a molar absorptivity within a range of 50,000-300,000, 75,000-300,000, 100,000-300,000, 125,000-300,000, or 150,000-300,000 M$^{-1}$cm$^{-1}$.

In any or all of the above embodiments, a cyanine fluorophore as disclosed herein may be soluble in aqueous solutions, e.g., PBS, 10% (v/v) FBS in PBS, and the like. Solubility is a tunable property and can be increased by increasing the number of polar substituents on the molecule. In some embodiments, solubility is tuned by varying the number of sulfonate groups present on the molecule. For example, certain cyanine fluorophores include from two to six sulfonate groups. The cyanine fluorophore may be symmetrically substituted with sulfonate groups. For example, R$^3$ and R$^6$ may both be sulfonate, R$^9$ and R$^{10}$ may both be alkyl sulfonate, and/or when the cyanine fluorophore has a structure according to one of Formulas II-IV, two of X$^1$-X$^4$ (e.g., X$^1$ and X$^3$, or X$^2$ and X$^4$) may comprise a sulfonate group. Other polar substituents such as substituents comprising pegylated groups, carbonyl, amide, amino, carboxylic acid, or carboxylate groups also may increase aqueous solubility. Some embodiments of the disclosed cyanine fluorophores are non-aggregating in aqueous solutions and/ or in vivo. In some instances, as relative solubility is increased, aggregation decreases. In any or all of the above embodiments, the disclosed cyanine fluorophores may be non-toxic (i.e., without significant adverse toxicological effects) when administered to a subject, e.g., a human, as described further below.

Several non-limiting examples of the disclosed cyanine fluorophores and their associated properties are shown in FIGS. 1A-1I.

III. PHARMACEUTICAL COMPOSITIONS

This disclosure also includes pharmaceutical compositions comprising at least one cyanine fluorophore as disclosed herein. Some embodiments of the pharmaceutical compositions include a pharmaceutically acceptable carrier and at least one cyanine fluorophore. Useful pharmaceutically acceptable carriers and excipients are known in the art.

The pharmaceutical compositions comprising one or more cyanine fluorophores may be formulated in a variety of ways depending, for example, on the mode of administration and/or on the location to be imaged. Parenteral formulations may comprise injectable fluids that are pharmaceutically and physiologically acceptable fluid vehicles such as water, physiological saline, other balanced salt solutions, aqueous dextrose, glycerol or the like. Excipients may include, for example, nonionic solubilizers, such as Cremophor®, or proteins, such as human serum albumin or plasma preparations. If desired, the pharmaceutical composition to be administered may also contain non-toxic auxiliary substances, such as wetting or emulsifying agents, preservatives, and pH buffering agents and the like, for example, sodium acetate or sorbitan monolaurate.

The form of the pharmaceutical composition will be determined by the mode of administration chosen. Embodiments of the disclosed pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation. Generally, embodiments of the disclosed pharmaceutical compositions will be administered by injection, systemically, or orally.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. The composition may take such forms as suspension, solutions or emulsions in oily or aqueous vehicles, and may contain formulatory agents such as suspending, stabilizing and/or dispersing agents. For example, parenteral administration may be done by bolus injection or continuous infusion. Alternatively, the cyanine fluorophore may be in powder form for reconstitution with a suitable vehicle, e.g. sterile water, before use.

Systemic formulations include those designed for administration by injection, e.g., subcutaneous, intravenous, intramuscular, intrathecal or intraperitoneal injection, as well as those designed for transdermal, transmucosal, oral or pulmonary administration.

Oral formulations may be liquid (e.g., syrups, solutions or suspensions), or solid (e.g., powder, tablets, or capsules). Oral formulations may be coupled with targeting ligands for crossing the endothelial barrier. Some cyanine fluorophore formulations may be dried, e.g., by spray-drying with a disaccharide, to form cyanine fluorophore powders. Solid compositions prepared by conventional means with pharmaceutically acceptable excipients such as binding agents (e.g., pregelatinised maize starch, polyvinylpyrrolidone or hydroxypropyl methylcellulose); fillers (e.g., lactose, mannitol, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings. Actual methods of preparing such dosage forms are known, or will be apparent, to those skilled in the art.

Liquid preparations for oral administration may take the form of, for example, elixirs, solutions, syrups or suspensions. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophor® or fractionated vegetable oils); and preservatives (e.g., methyl or propyl-p-hydroxybenzoates or sorbic acid). The preparations may also contain buffer salts, preservatives, flavoring, coloring and sweetening agents as appropriate. Preparations for oral administration may be suitably formulated to give controlled release of the fluorophore, as is well known.

For rectal and vaginal routes of administration, the cyanine fluorophore(s) may be formulated as solutions (for retention enemas) suppositories or ointments containing conventional suppository bases such as cocoa butter or other glycerides.

For nasal administration or administration by inhalation or insufflation, the cyanine fluorophore(s) can be conveniently delivered in the form of an aerosol spray or mist from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount.

Certain embodiments of the pharmaceutical compositions comprising cyanine fluorophores as described herein may be formulated in unit dosage form suitable for individual administration of precise dosages. The pharmaceutical compositions may, if desired, be presented in a pack or dispenser device which may contain one or more unit dosage forms containing the cyanine fluorophore. The pack may, for example, comprise metal or plastic foil, such as a blister pack. The pack or dispenser device may be accompanied by instructions for administration.

The amount of cyanine fluorophore administered will depend at least in part on the subject being treated, the target (e.g., the size, location, and characteristics of a tumor), and the manner of administration, and may be determined as is known to those skilled in the art of pharmaceutical composition and/or contrast agent administration. Within these bounds, the formulation to be administered will contain a quantity of the cyanine fluorophore disclosed herein in an amount effective to enable visualization of the cyanine fluorophore by suitable means after administration to the subject. In certain embodiments, the cyanine fluorophore comprises a drug bound to the molecule, and the formulation to be administered will contain a quantity of the drug bound to the cyanine fluorophore effective to provide a therapeutically effective dose of the drug to the subject being treated.

In some embodiments, the pharmaceutical composition includes a second agent other than the cyanine fluorophore. The second agent may be, for example, an anti-tumor agent or an angiogenesis inhibitor.

IV. SYNTHESIS

Figure 2:
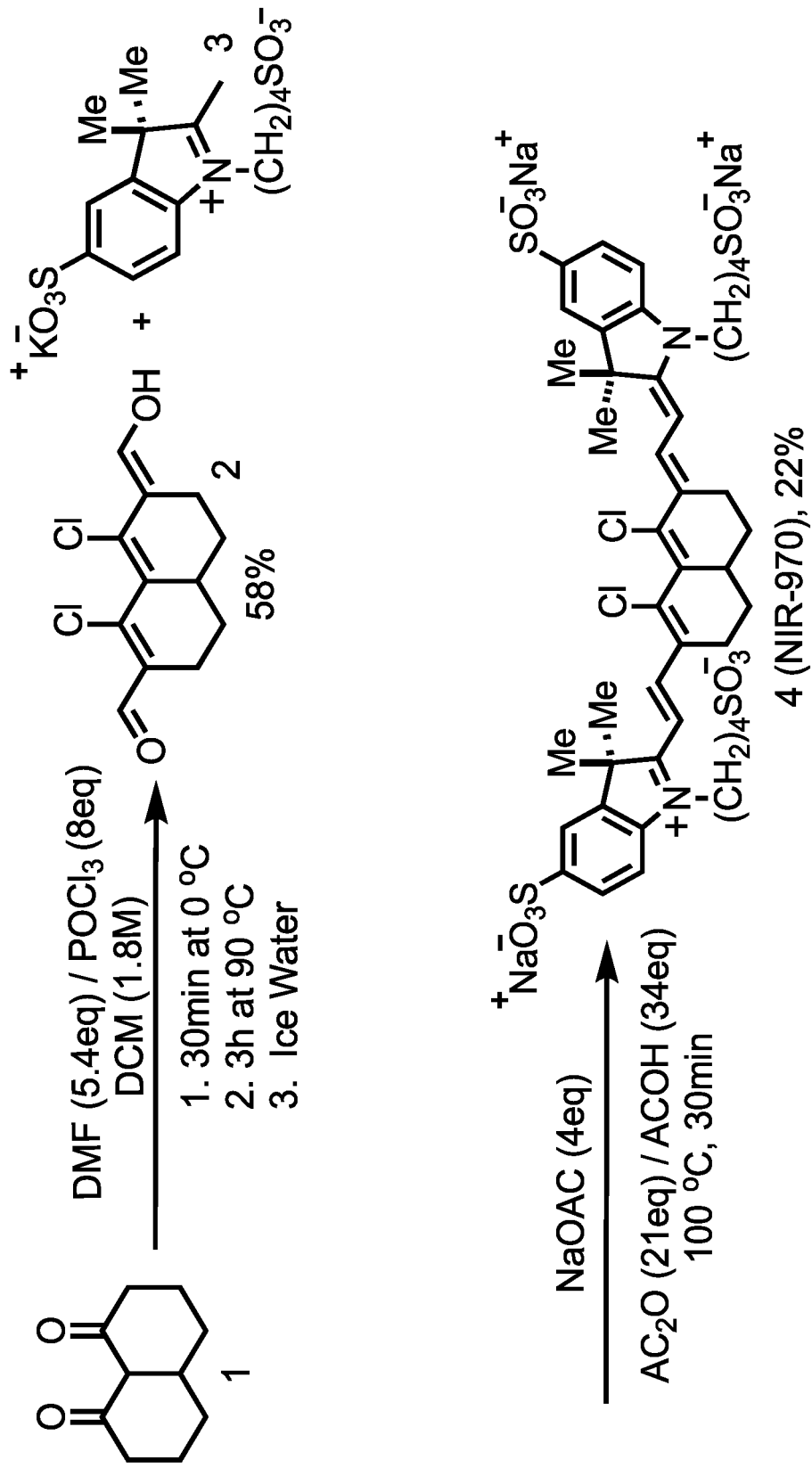
FIGS. 2-18 are exemplary synthesis schemes for several cyanine fluorophores as disclosed herein.
Figure 3:
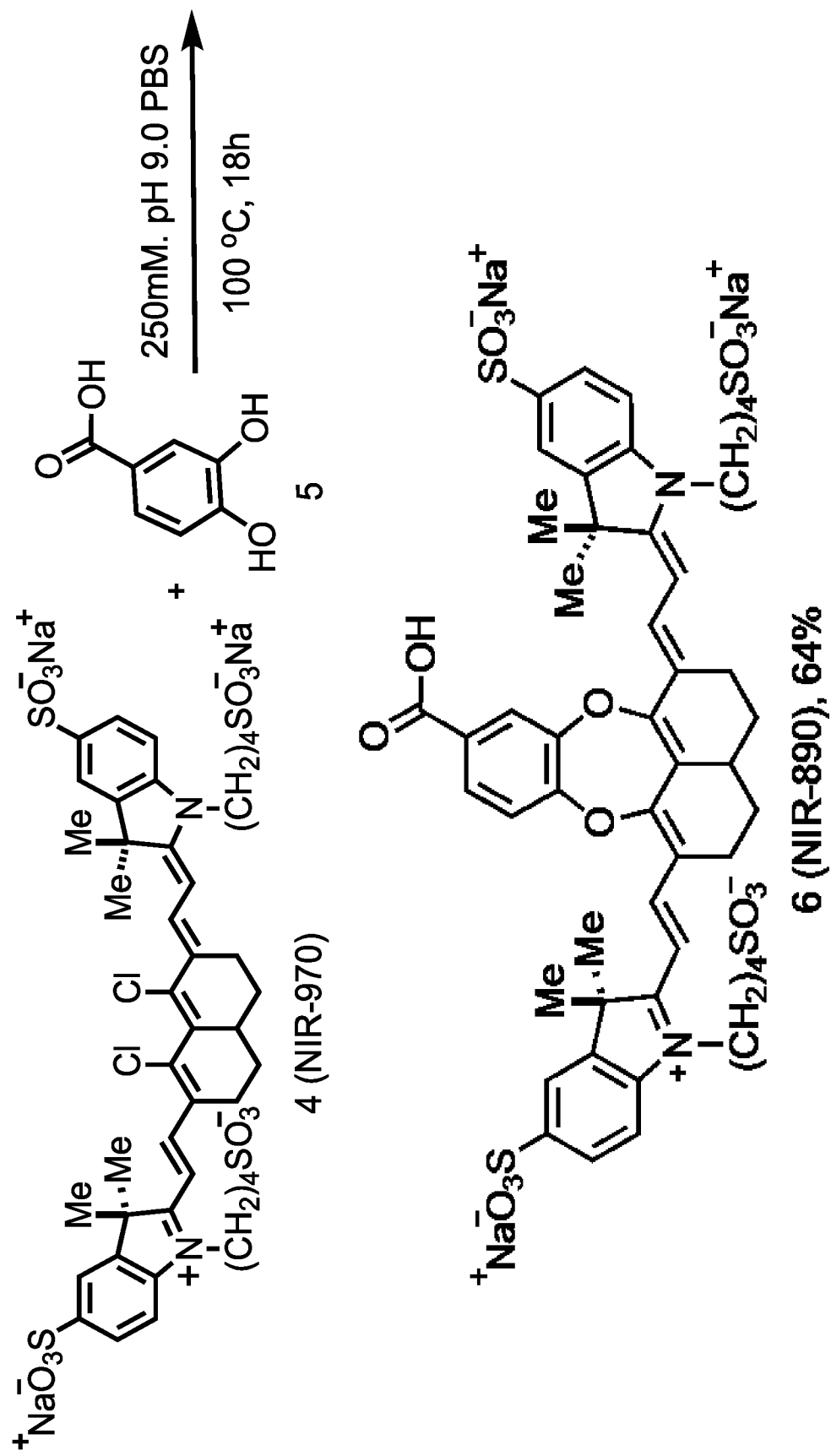
Figure 4:
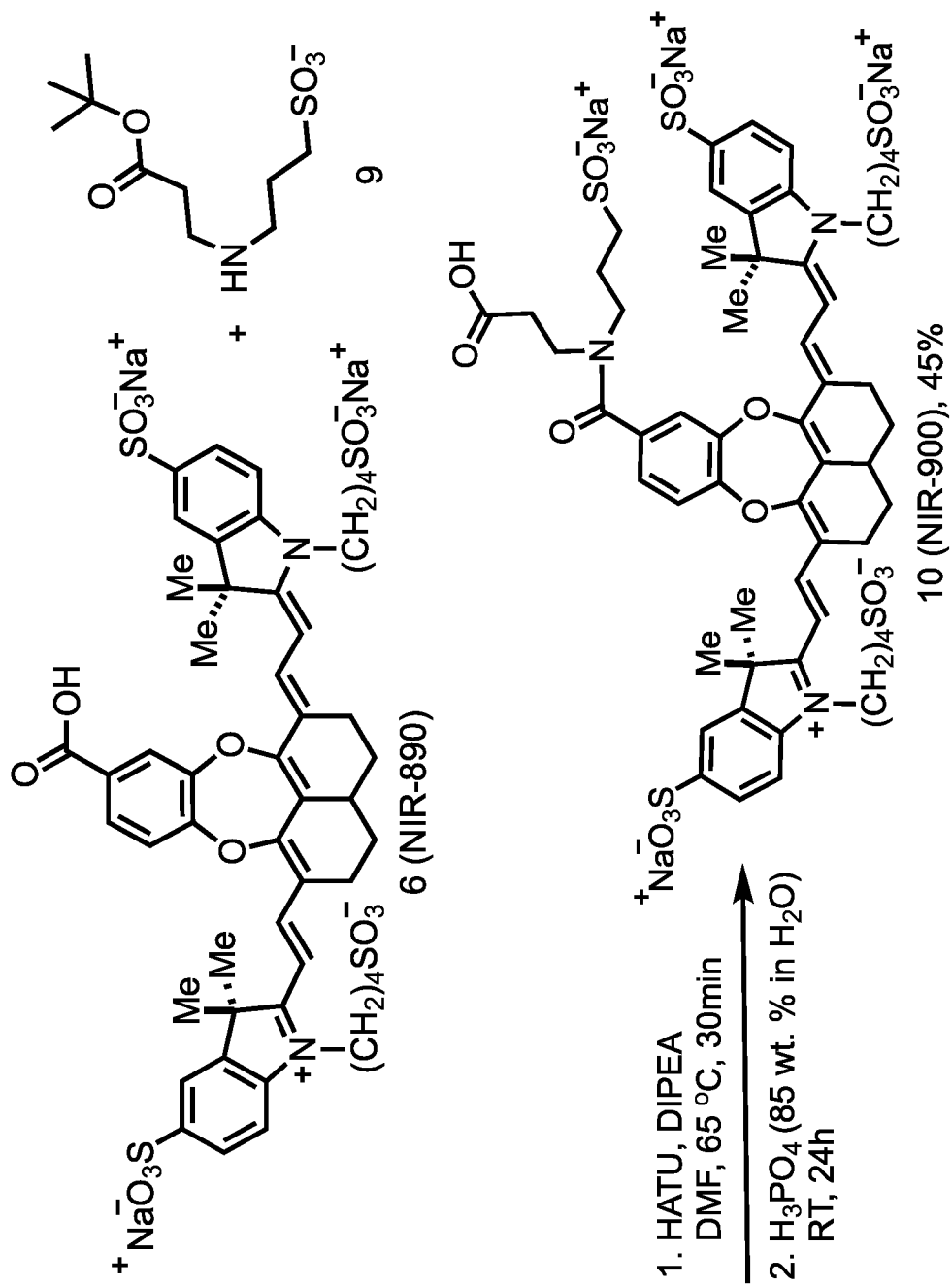
Figure 22:
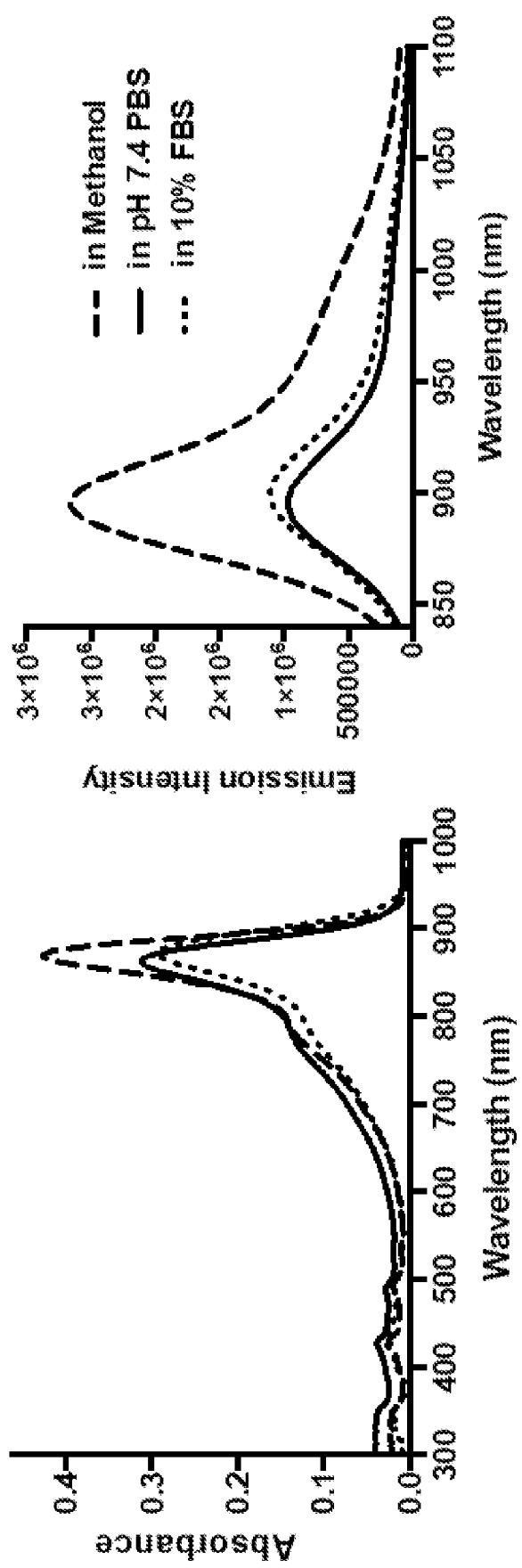
FIG. 22 shows absorbance (left) and emission (right, excitation at 820 nm) spectra of a 2 μM solution of cyanine fluorophore (compound 10, NIR-900) in different solvents as indicated.
Figure 34:
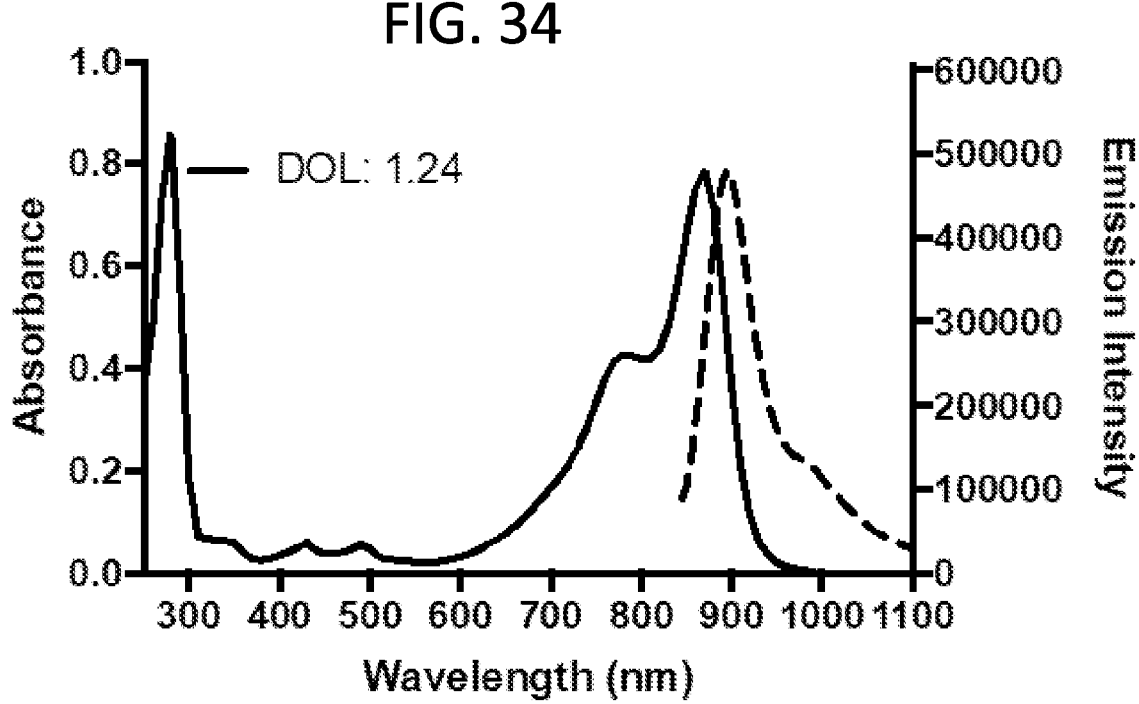
FIG. 34 is an absorbance (solid line) and emission (dashed line) spectrum of an antibody conjugate of a cyanine fluorophore (NIR-900-Panitumumab) in pH 7.4 PBS.

Exemplary synthesis schemes for some embodiments of the disclosed cyanine fluorophores are shown in FIGS. 2-18. A first intermediate, compound 4 (NIR-970) may be synthesized as set forth in FIG. 2. The two chloro groups on compound 4 allow further modification. Tetrasulfonated compound 6 (NIR-890) (FIG. 3) is synthesized by reaction of compound 4 with 3,4-dihydroxybenzoic acid. Compound 6 is soluble in both pH 7.4 PBS and serum (FIG. 20) with only moderate aggregation. Compound 6 can be further modified by reaction with compound 9 to create pentasulfonated compound 10 (NIR-900) (FIG. 4), which eliminated aggregation in both PBS and serum (FIG. 22). The carboxylic acid group of compound 10 can be converted to an N-hydroxysuccinimide ester, followed by conjugation to an antibody (e.g., panitumumab) to form an antibody conjugate, e.g., NIR-900-Panitumumab (FIG. 34).

Figure 5:
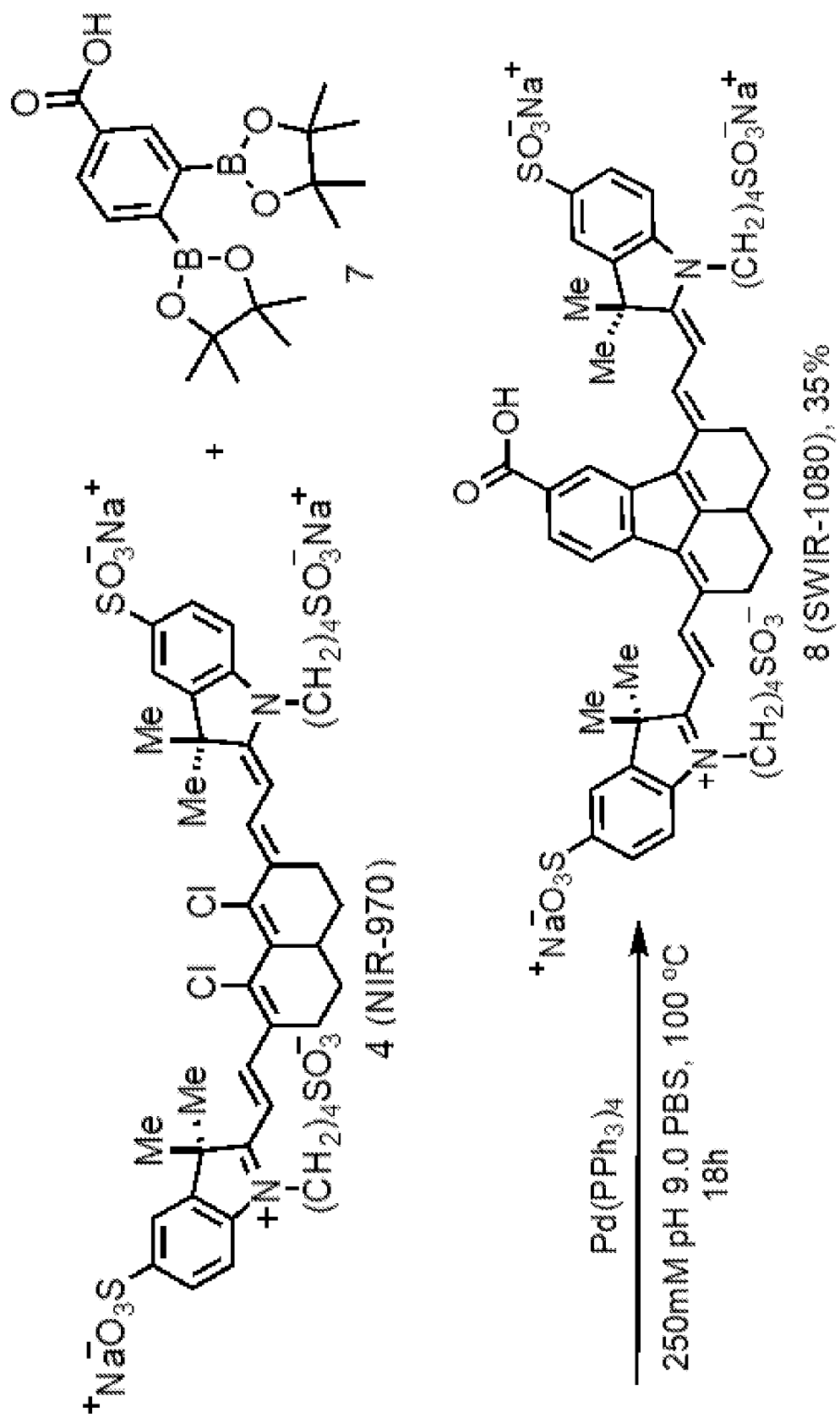
Figure 6:
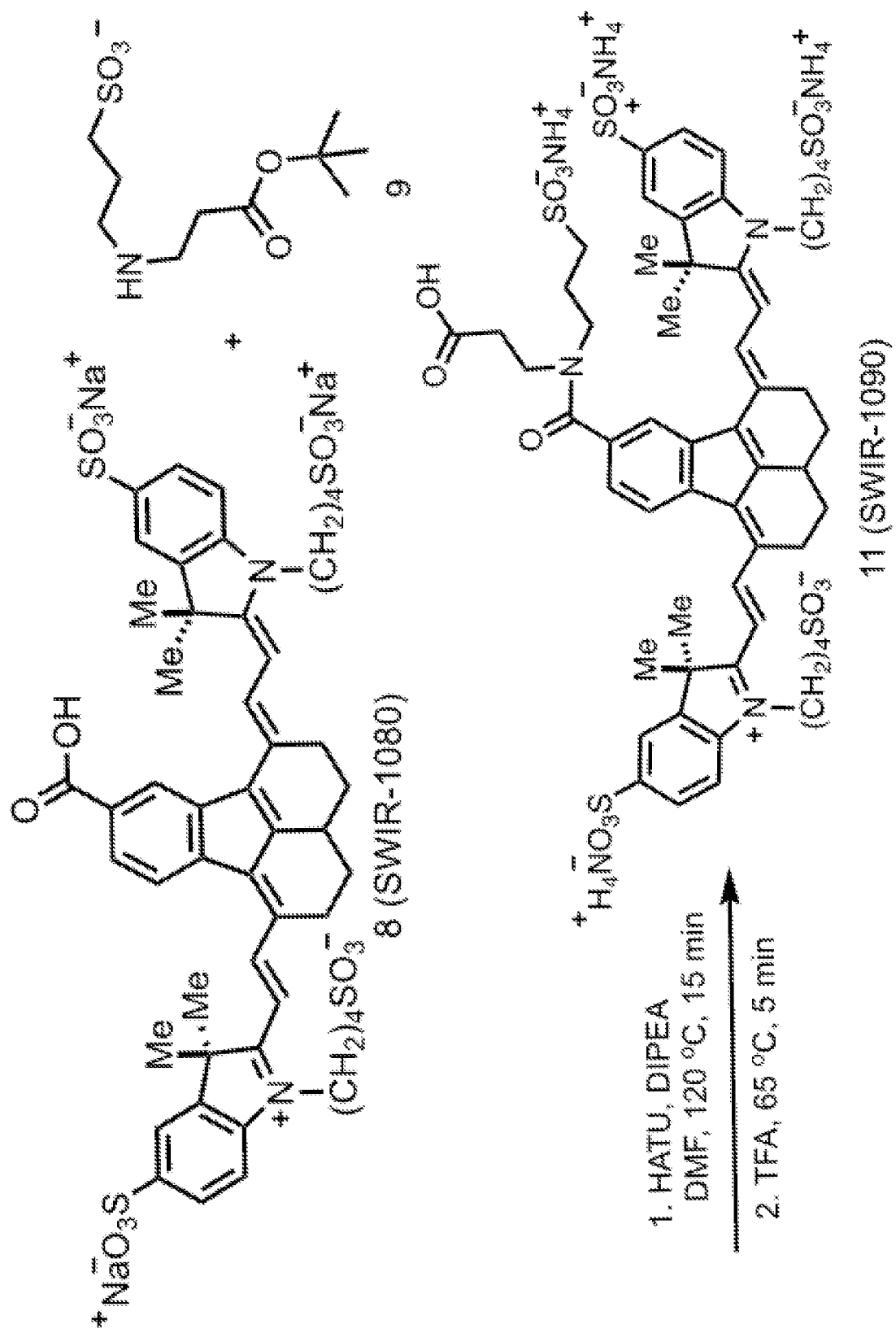
Figure 7:
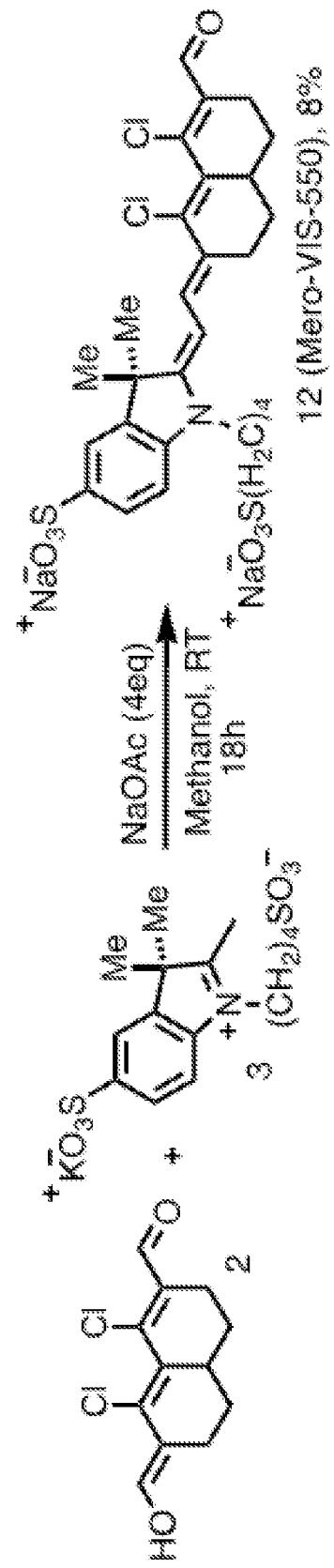
Figure 8:
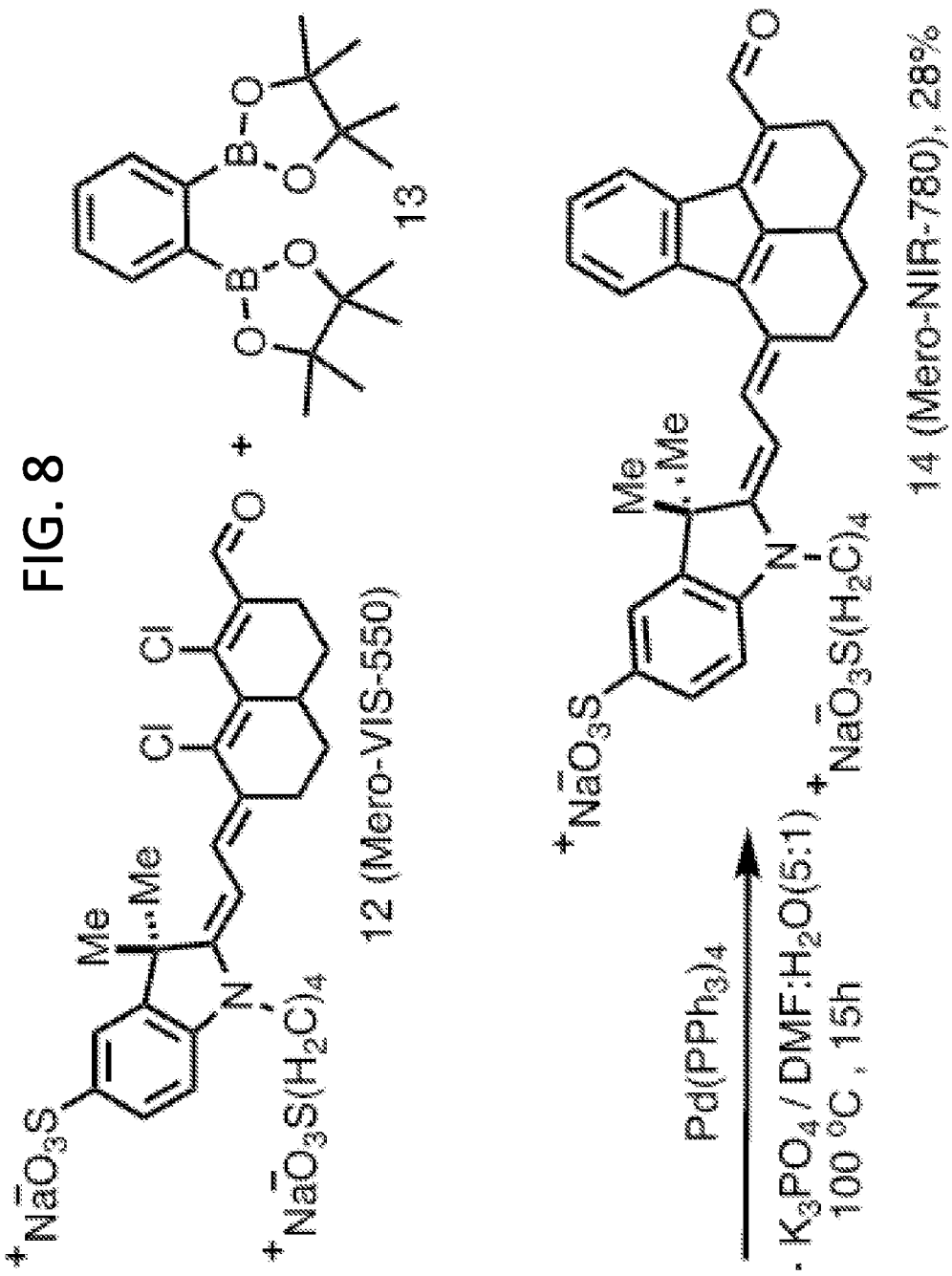
Figure 9:
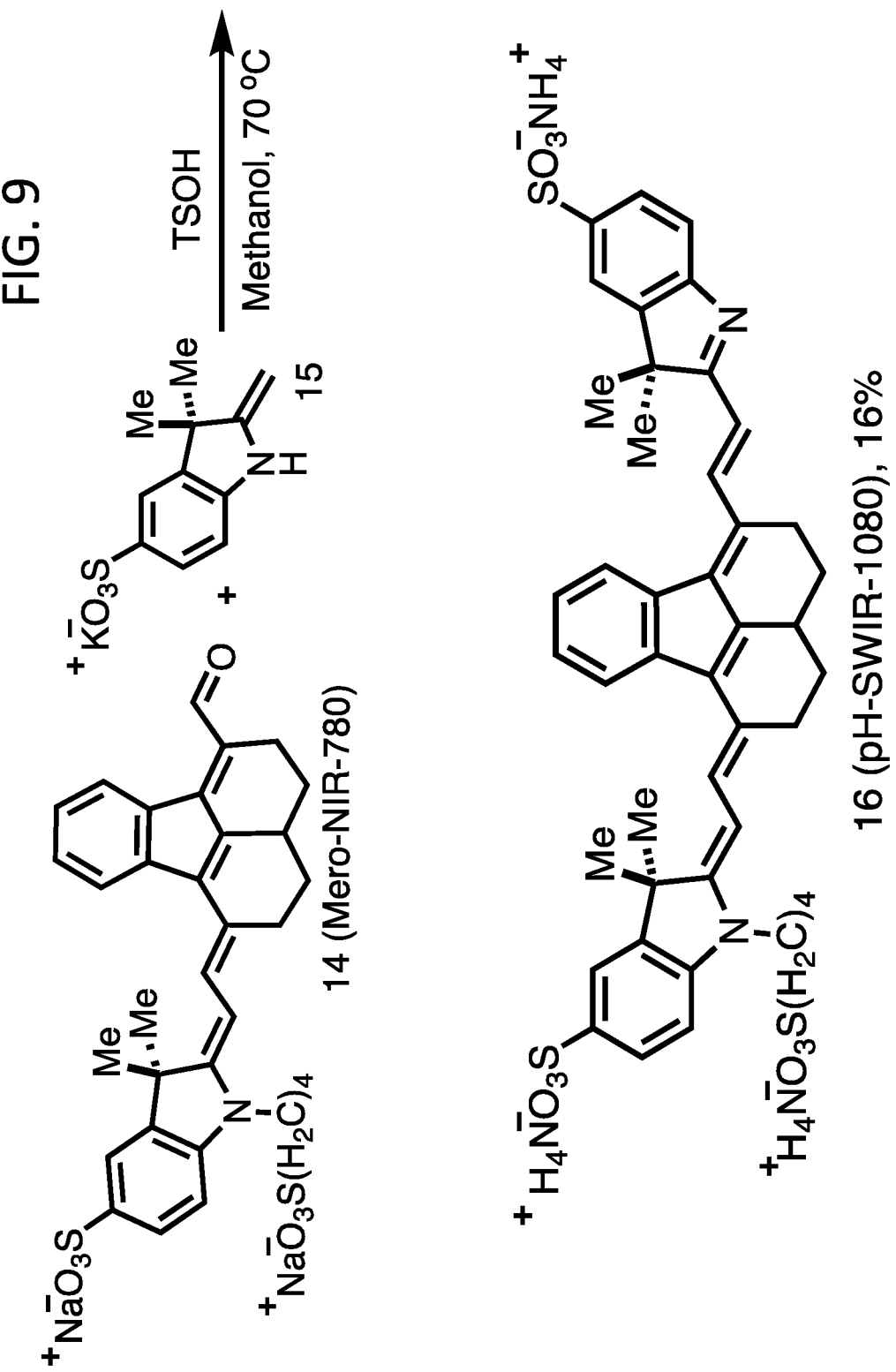
Figure 10:
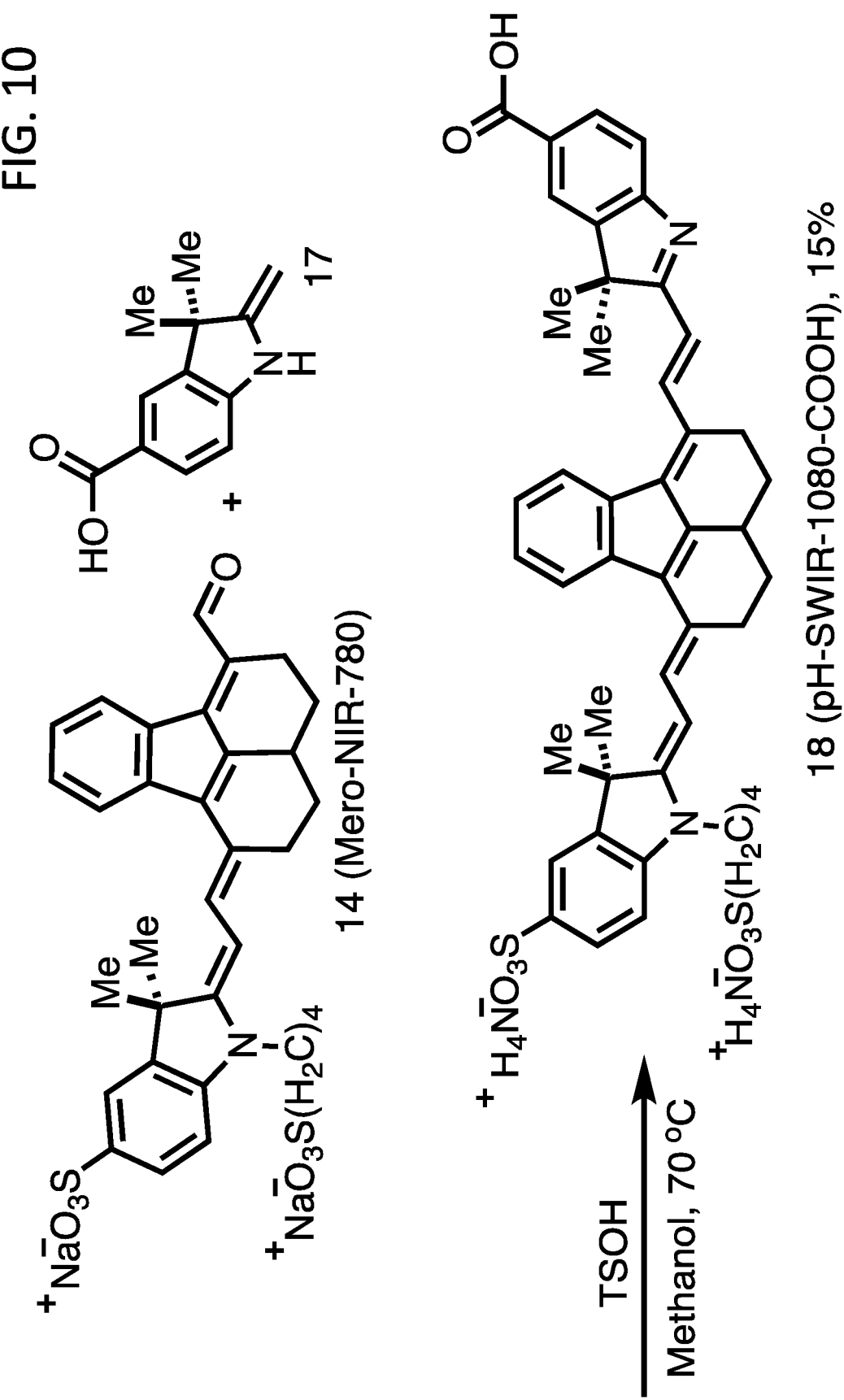
Figure 11:
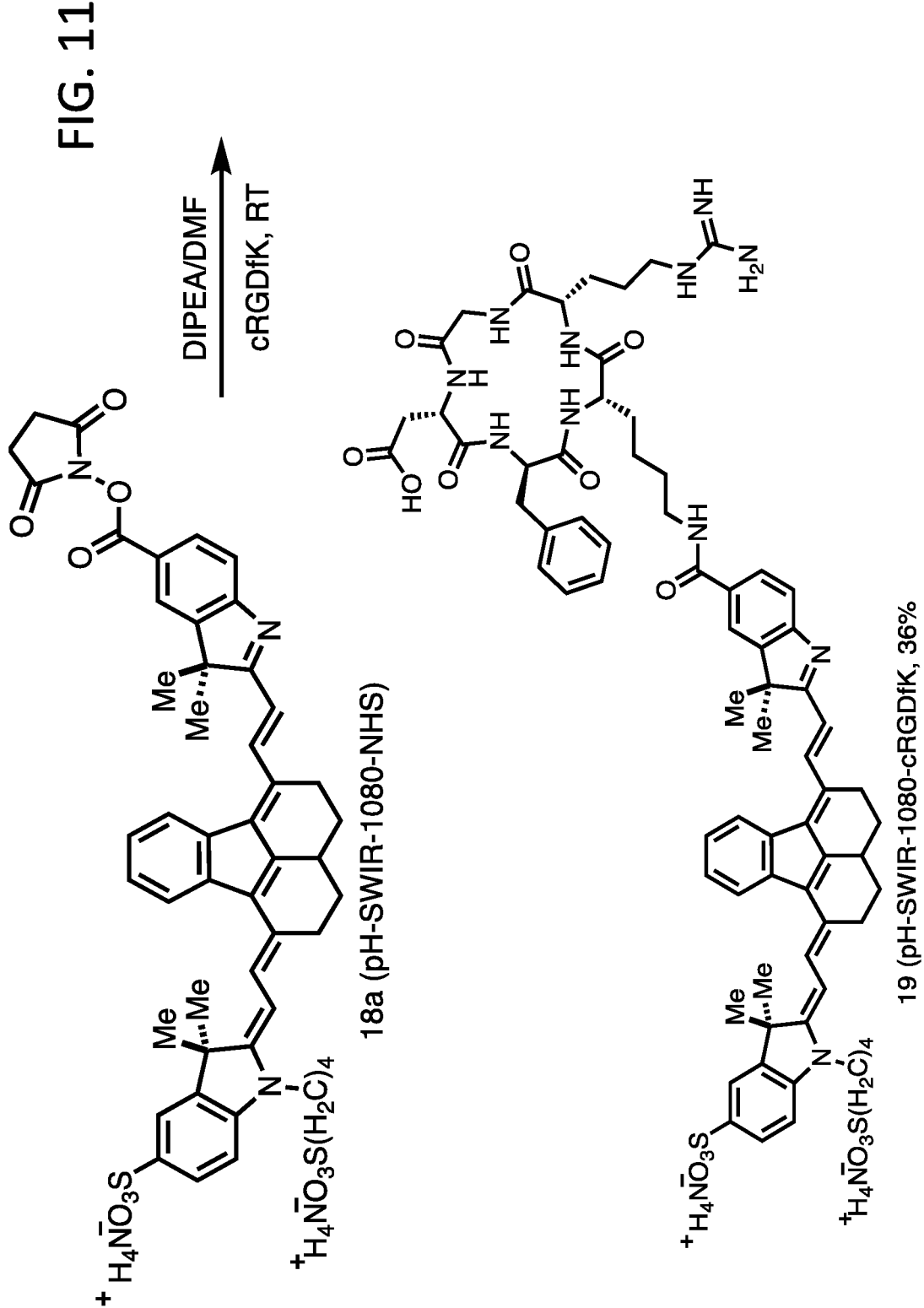
Figure 12:
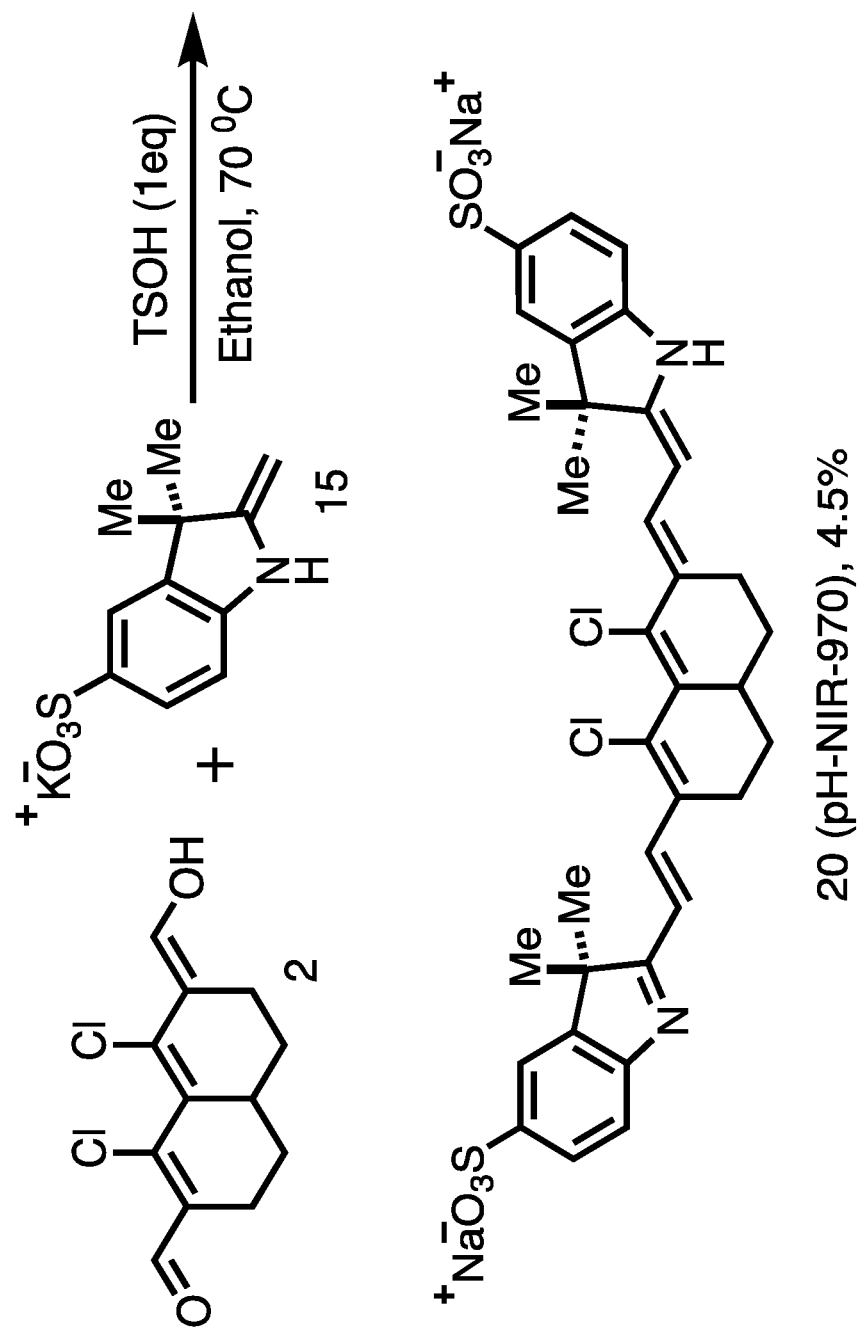
Figure 13:
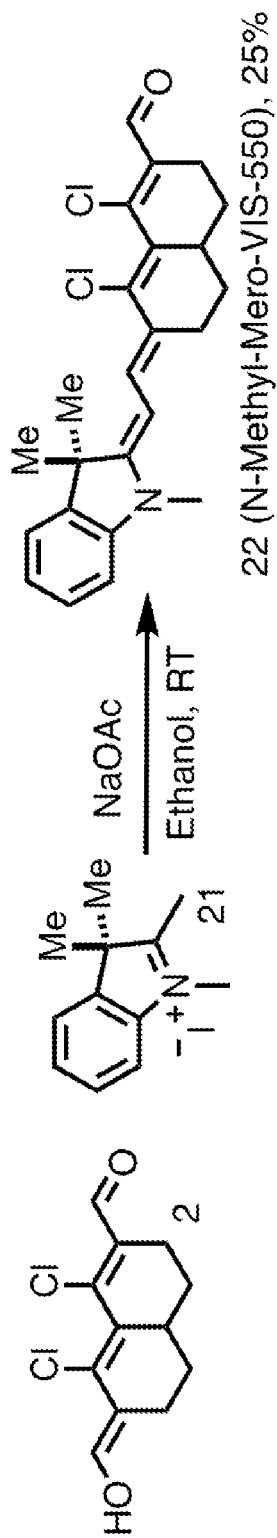
Figure 14:
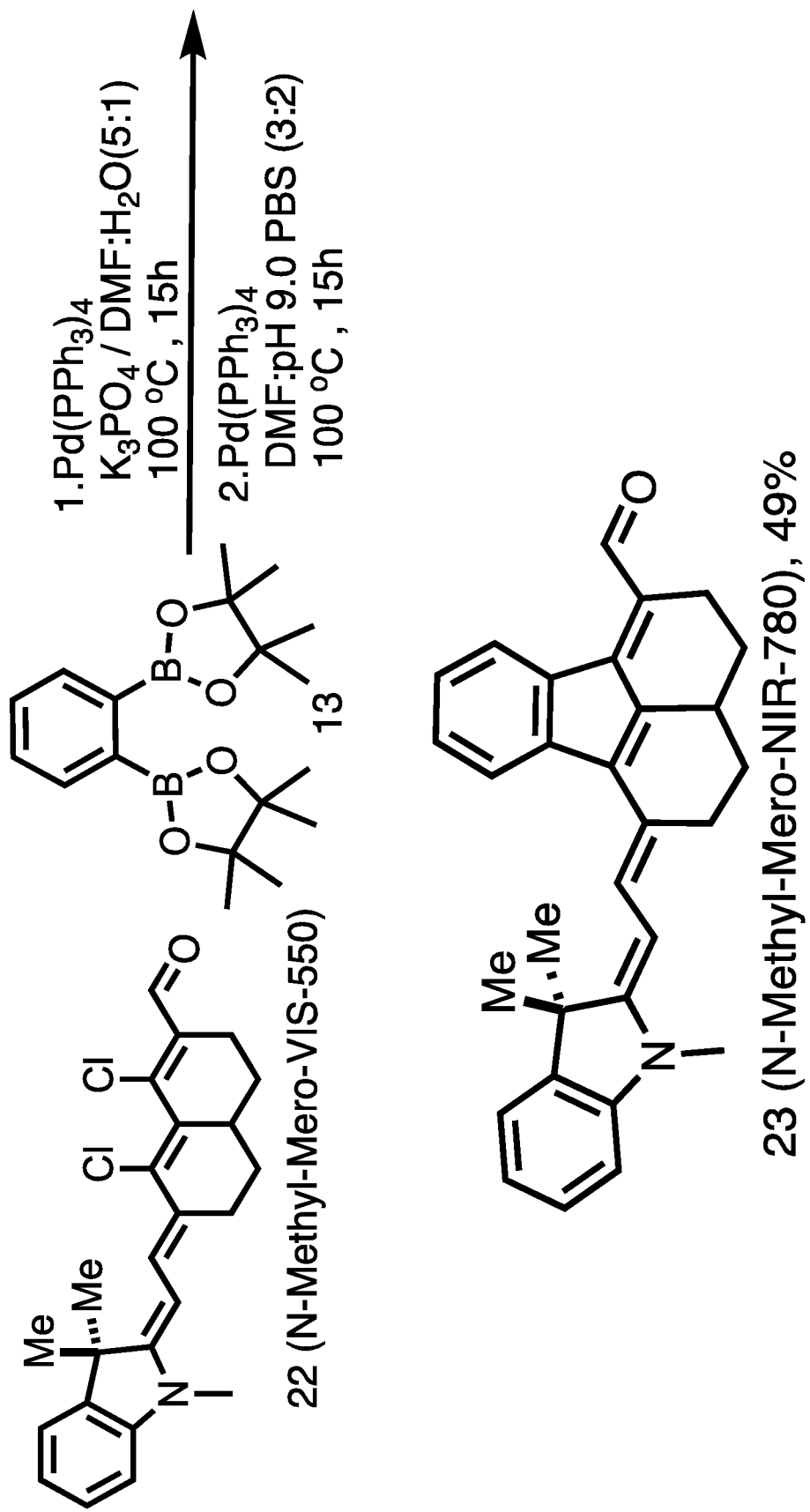
Figure 15:
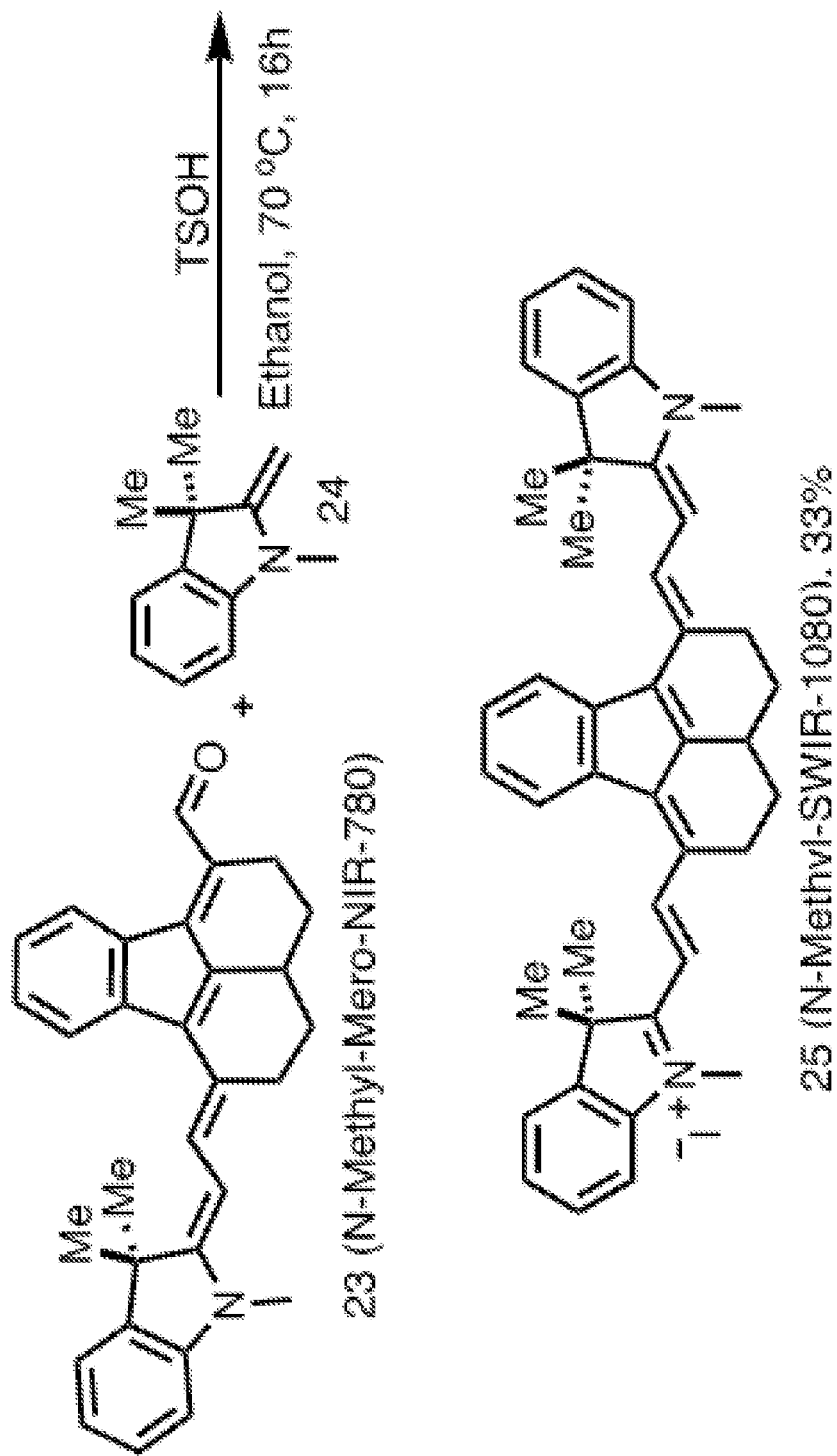
Figure 16:
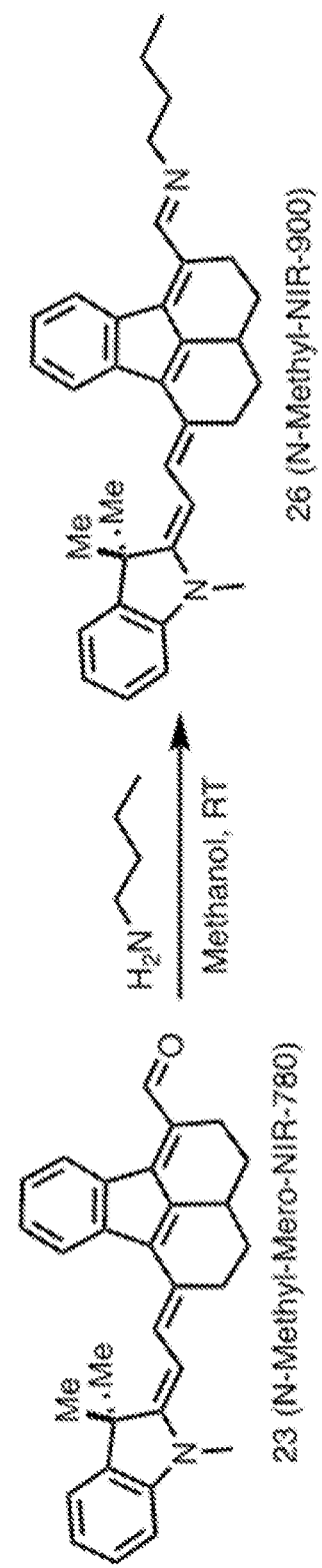

As shown in FIG. 5, compound 4 may coupled with 3,4-diboronic acid bis(pinacol) ester benzoic acid (compound 7), to create a tetra-sulfonated compound 8 (SWIR-1080). Aggregation was eliminated by modification with compound 9 to provide a pentasulfonated analog, compound 11 (SWIR-1090) (FIG. 6).

V. METHODS OF USE

Embodiments of the disclosed compounds according to any one of Formulas I-V may be useful for live-cell localization and tracking applications. In certain embodiments, inclusion of sulfonate or other polar functional groups may facilitate detectable labeling, such as antibody labeling. Furthermore, some embodiments of the disclosed compounds may be cell-permeable, an advantage for live-cell studies. Investigative, diagnostic, and theranostic uses are within the scope of the disclosure.

Compounds according to any one of Formulas I-V may be utilized in in vitro, ex vivo, and in vivo localization and tracking applications. In some embodiments, a compound according to Formula I that comprises at least one targeting agent is combined with a sample comprising a target capable of binding with the targeting agent, and the target is imaged by visualizing the compound. The sample may be, for instance, a tissue sample, a biological fluid (e.g., blood, urine, saliva), or a target area within a subject such as a location of a known or suspected tumor. Advantageously, combining the compound with the sample is performed under conditions (temperature, pH, concentration, etc.) effective to provide binding of the targeting agent and target. After a period time effective for binding to occur, which may range from a few seconds to several days, the compound is visualized. Prior to visualization, excess, unbound compound may be removed from the sample, e.g., by washing the sample under conditions effective to remove unbound compound without disrupting compound molecules bound to the target or by waiting a sufficient period of time (such as a few hours or days) for unbound compound to be eliminated from the target area in vivo.

In some embodiments, visualization comprises irradiating the sample or a targeted portion of a subject with targeted application of a quantity of light having a wavelength in the near-infrared or short-wave infrared range and a selected intensity, wherein the quantity of light is sufficient to produce fluorescence of the compound, and detecting any fluorescence emitted by the compound. Advantageously, the light has a wavelength at or near a maximum absorption wavelength of the compound according to any one of Formulas I-V. For example, the sample may be irradiated with light having a wavelength $\geq 650$ nm, $\geq 700$ nm, $\geq 750$ nm, $\geq 800$ nm, $\geq 850$ nm, $\geq 875$ nm, or $\geq 900$ nm, such as a wavelength within a range of 650-1700 nm, 750-1700 nm, 850-1700 nm, 850-1500 nm, 850-1200 nm, or 900-1100 nm.

In some embodiments, the light source is a laser. In certain embodiments, the laser is a Nd:YAG (neodymium-doped yttrium aluminum garnet, $Nd:Y_3Al_5O_{12}$) laser, which emits light at 1064 nm. Suitable light intensities may range from 1 mW/cm$^2$ to 1000 mW/cm$^2$, such as 1-750 mW/cm$^2$ or 300-700 mW/cm$^2$, depending on the target site and method of application. Near-infrared light sources can be obtained from commercial sources, including Thorlabs (Newton, N.J.), Laser Components, USA (Hudson, N.H.), ProPhotonix (Salem, N.H.) and others. In some embodiments, the effective quantity of NIR or SWIR light is 10-250 J, such as 10-200 J, 10-150 J, or 10-100 J.

In some embodiments, visualization may include techniques such as fluoroscopy, single-molecule localization microscopy (SMLM), photo-activated localization microscopy (PALM), stochastic optical reconstruction microscopy (STORM), direct stochastic optical reconstruction microscopy (dSTORM), biplane imaging (BP), temporal radial-aperture based intensity estimation (TRABI), fluorescence resonance energy transfer (FRET), and combinations thereof.

In some embodiments, an effective amount of a compound according to Formula I or a pharmaceutical composition comprising the compound is administered to a subject suspected of having a condition that may be detected and/or evaluated by visualizing a fluorophore bound to a target (e.g., a tumor) within the subject. Advantageously, the compound according to any one of Formulas I-V may include a targeting agent capable of binding to the target within the subject. Administration is performed by any suitable method, e.g., intravenous, intra-arterial, intramuscular, intratumoral, or subcutaneous injection, or oral, intranasal, or sublingual administration. The administered compound is subsequently irradiated by targeted application of a quantity of light having a wavelength in the NIR or SWIR range and a selected intensity to a target area of the subject, wherein the quantity of light is sufficient to excite the compound according to any one of Formulas I-V. When irradiating a target area (e.g., an area proximate a tumor), the effective quantity of far-red or NIR light may be 1-250 J/cm$^2$, such as 1-250 J/cm$^2$, such as 5-250 J/cm$^2$, 10-250 J/cm$^2$, 10-200 J/cm$^2$, 10-150 J/cm$^2$, 10-100 J/cm$^2$, or 30-100 J/cm$^2$. Any fluorescence from the compound in the targeted portion of the subject is detected, thereby diagnosing the subject as having the condition.

In certain theranostic embodiments, the condition is a tumor and the targeted portion of the subject includes the tumor site. The administered compound is visualized by exposing the tumor to light having a wavelength and intensity sufficient to induce fluorescence of the compound and detecting the fluorescence. Irradiation may be performed by external application of light to a targeted area of a subject. NIR or SWIR light is capable of penetrating transcutaneously into tissue to a depth of several centimeters. In other embodiments, irradiation may be performed by internal application of light, such as by using an endoscope, a fiber optic catheter, or an implantable fluorescence device. Internal application may be used when the target tissue, such as a tumor, is located at a depth that is unsuitable for external light application. For example, an endoscope may be used for light delivery into the lungs, stomach, or bladder. In some examples, the tumor site is exposed by surgical incision prior to exposing the tumor to light. The tumor may be excised using the area of fluorescence as guidance. In one embodiment, at least a portion of the tumor is excised from the subject before administering the therapeutically effective amount of the compound or the pharmaceutical composition comprising the compound to the subject. In an independent embodiment, the therapeutically effective amount of the compound or the pharmaceutical composition comprising the compound is administered to the subject before surgical excision of the tumor or a portion thereof.

The surface area for light application is generally selected to include target tissue, e.g., a tumor or portion of a tumor, or an area of skin external to the target tissue. When targeted application of external light is desired for an in vivo biological sample, the surface area can be controlled by use of an appropriate light applicator, such as a micro-lens, a Fresnel lens, or a diffuser arrangement. For targeted internal light application, a desired endoscope or fiber optic catheter diameter can be selected. In some applications, an indwelling catheter filled with a light scattering solution may be internally placed proximate the target tissue, and an optical fiber light source may be inserted into the catheter (see, e.g., Madsen et al., *Lasers in Surgery and Medicine* 2001, 29, 406-412).

In another embodiment, an in vitro or ex vivo evaluation may be performed to determine whether a compound according to any one of Formulas I-V will effectively bind to a tissue sample obtained from a subject having, or suspected of having, a condition that may be visualized by the compound. The compound comprises a targeting agent thought to be capable of binding to or associating with a target molecule indicative of or associated with the condition. In one non-limiting example, the targeting agent is a receptor ligand or antibody capable of binding to a target receptor. The compound is combined with the tissue sample, and the sample is subsequently irradiated with an effective amount of NIR or SWIR light. In one embodiment, the tissue sample is washed to remove excess, unbound compound, and fluorescence of the tissue sample is assessed. Fluorescence indicates that the compound has bound to the tissue sample.

In an independent embodiment, a compound according to any one of Formulas I-V may be used to visualize shapes and/or structures within a subject. For example, the compound or a pharmaceutical composition comprising the compound may be injected intravenously into a subject and subsequently visualized to show vascular structure with high resolution within the subject or within a target area of the subject. In such embodiments, the compound may not include a targeting agent.

In another independent embodiment, a compound according to any one of Formulas I-V may be utilized to visualize shapes and/or structures within a cell. A compound according to any one of Formulas I-V may include a targeting agent capable of binding to a desired component within a cell, e.g., a fixed or permeabilized cell. For example, the compound may include phalloidin as a targeting agent that binds to F-actin. Visualization of F-actin is useful for showing the overall shape and structure of a cell.

In still another independent embodiment, compound according to any one of Formulas I-V may be used for drug delivery to a subject. In such embodiments, the subject may have a condition that can be treated with a drug. The compound includes a drug effective to treat the condition. The compound or a pharmaceutical composition comprising the compound is administered to the subject by any suitable method. Presence and distribution of the compound and its drug in the subject may be confirmed by visualizing the compound as previously described, e.g., by exposing at least a portion (i.e., a targeted portion) of the subject to light having a wavelength and intensity sufficient to induce fluorescence of the compound, and detecting the fluorescence.

In yet another independent embodiment, a compound according to any one of Formulas I-V may be used for targeted drug delivery to a subject. In such embodiments, the subject may have a condition that can be treated with a drug. The compound may include (i) a targeting agent capable of binding to a target (e.g., a particular cell type) within the subject, and (ii) a drug effective to treat the condition. The compound or a pharmaceutical composition comprising the compound is administered to the subject by any suitable method. The compound binds to the target within the subject, thereby selectively delivering the drug to the target. Presence of the compound at the target may be confirmed by visualizing the compound as previously described, e.g., by exposing the target to light having a wavelength and intensity sufficient to induce fluorescence of the compound, and detecting the fluorescence. In some examples, the target is a cancer cell, such as a tumor cell, the targeting agent is an antibody capable of binding to the cancer cell, and the drug is an anti-cancer agent.

VI. EXAMPLES

Example 1

Cyanine Fluorophore Synthesis and Characterization

An exemplary synthesis scheme for several fluorophores is shown in FIGS. 2-6.

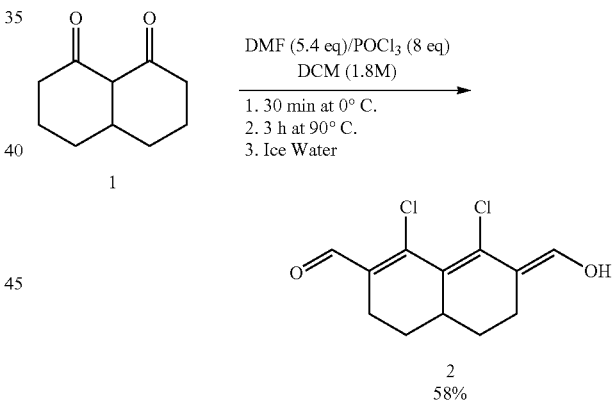

Synthesis of 2: To a microwave reaction vial equipped with a magnetic stir bar was added DMF (5 mL, 64.4 mmol, 5.4 eq) and 2 mL of $CH_2Cl_2$. The vessel was sealed under argon and cooled to 0° C., after which $POCl_3$ (9.45 mL, 101.08 mmol, 8 eq) was slowly added and stirred at 0° C. for 30 min. Decahydronaphthalene-1,8-dione (compound 1) (2.1 g, 12.6 mmol, 1 eq) was added in 2 mL $CH_2Cl_2$, and the reaction mixture was stirred at 90° C. for 1 h. The reaction was poured onto crushed ice and product extracted with $CH_2Cl_2$ (3×100 ml). The combined organic solution was dried over $Na_2SO_4$ and concentrated under reduced pressure to yield an orange colored thick liquid compound 2 (1.89 g, 58% yield) was used in the next step without further purification. LCMS calculated for $C_{12}H_{12}Cl_2O_2$ (M+H$^+$) 258.02, observed 258.7. NMR has few excess peaks unable to purify because it is unstable during column separation.

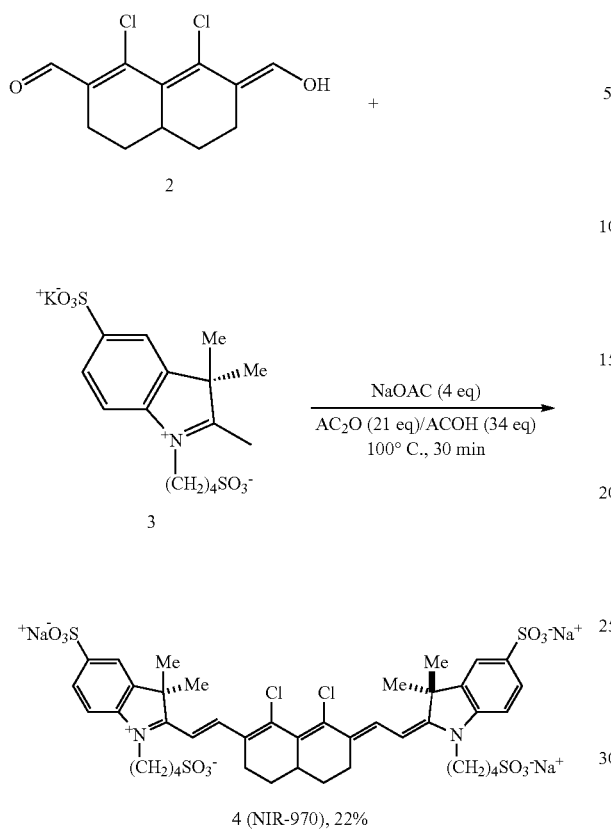

4 (NIR-970), 22%

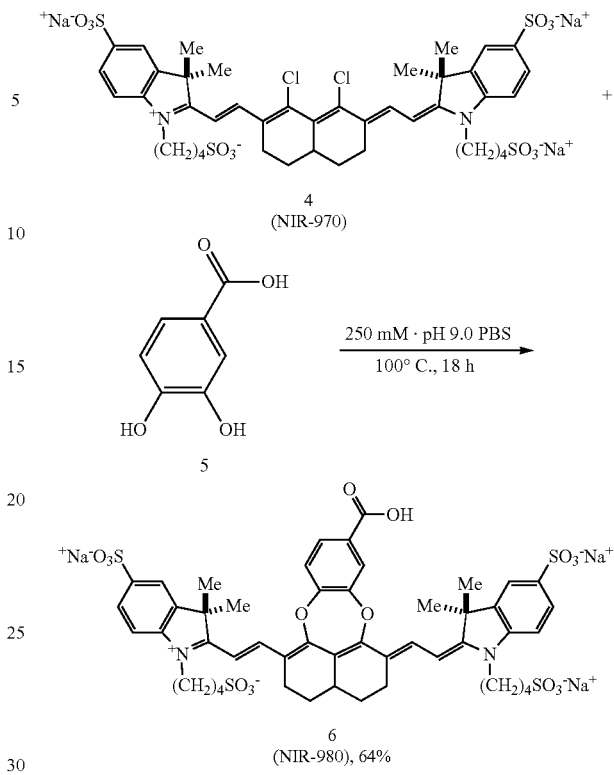

6 (NIR-980), 64%

Synthesis of 4 (NIR-970): To a microwave reaction vial equipped with a magnetic stir bar was added bis sulfonated Indolenine 3 (4.8 g, 11.6 mmol, 3 eq), compound 2 (1 g, 3.87 mmol, 1 eq) and sodium acetate (1.27 g, 15.5 mmol, 4 eq). After flushing with argon, acetic acid (7.53 mL, 131.78 mmol, 34 eq) and acetic anhydride (7.69 mL, 81.39 mmol, 21 eq) were added in succession. The brown solution was heated to 90° C. for 30 minutes. The reaction mixture was cooled, and diluted with saturated aqueous NaHCO$_3$ (5 mL). The resulting residue was purified by reversed-phase chromatography (150 g C$_{18}$ Aq, 0→30% acetonitrile/water), and the product-containing fractions were genevaced to afford 4 (NIR-970) (912 mg, 22% yield) as a green solid. $^1$H NMR (500 MHz, methanol-d$_4$) δ 8.39 (d, 2H), 7.94-7.91 (m, 4H), 7.43 (d, 2H), 6.44 (d, 2H), 4.25 (s, 4H), 3.02-2.98 (m, 2H), 2.92 (t, 5H), 2.56-2.53 (dd, 2H), 2.23 (s, 2H), 2.03-1.98 (m, 10H), 1.78 (s, 12H); $^{13}$C NMR (500 MHz, methanol-d$_4$) δ 172.05, 143.72, 143.28, 141.99, 141.79, 141.23, 131.64, 130.47, 126.81, 120.00, 110.38, 103.05, 50.30, 49.16, 44.08, 40.78, 29.21, 26.71, 25.84, 25.37, 22.18; HRMS (ESI) calculated for $C_{42}H_{47}Cl_2N_2O_{12}S_4^{3-}$ (M+3H) 972.14, observed 973.1 (MH$^+$).

Figure 19:
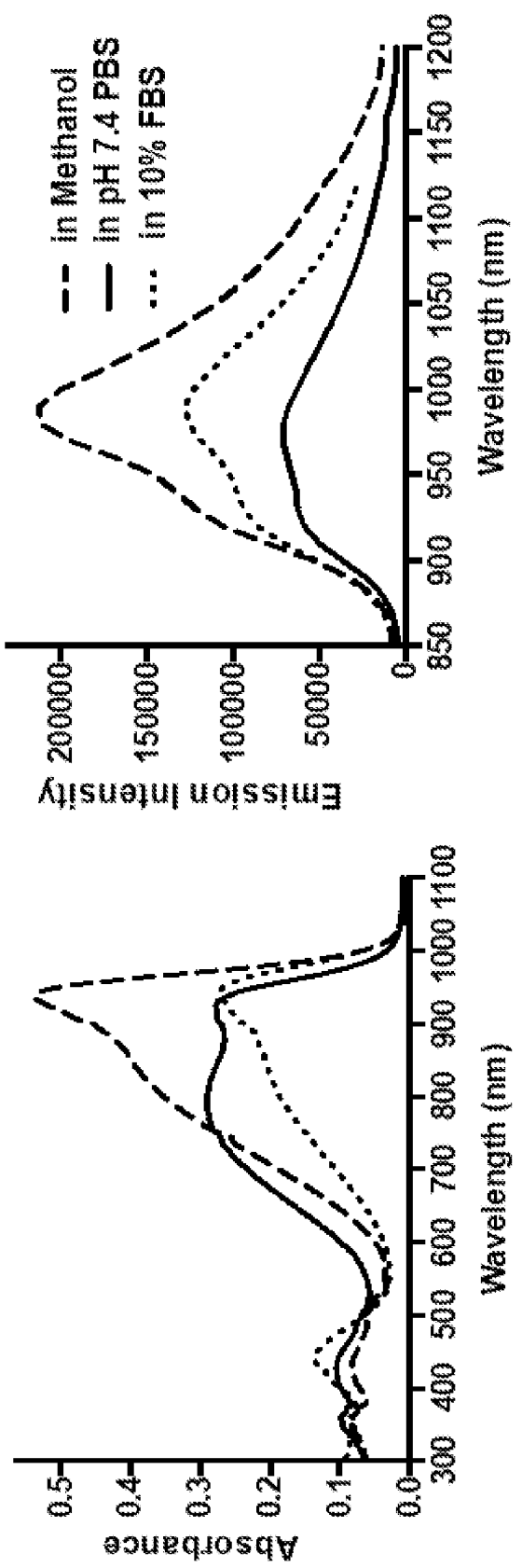
FIG. 19 shows absorbance (left) and emission (right, excitation at 770 nm) spectra of a 5 μM solution of cyanine fluorophore (compound 4, NIR-970) in different solvents as indicated.

FIG. 19 shows absorbance (left) and emission (right) spectra of compound 4 (NIR-970) in different solvents as indicated. Compound 4 (NIR-970) exhibited an absorbance maximum ($\lambda_{max,\ abs}$) of 920 nm, an emission maximum ($\lambda_{max,\ emiss}$) of 970 nm, and a molar absorptivity (ε, M$^{-1}$cm$^{-1}$) of 55,000 in pH 7.4 PBS, $\lambda_{max,\ abs}$=940 nm, $\lambda_{max,\ emiss}$=990 nm, and ε=53,000 in 10% (v/v) FBS in pH 7.4 PBS, and $\lambda_{max,\ abs}$=938 nm, $\lambda_{max,\ emiss}$=990 nm, and ε=102,000 in methanol.

Synthesis of 6 (NIR-890): To a microwave vial equipped with a magnetic stir bar was added compound 4 (187 mg, 0.18 mmol, 1 eq) and 3,4-Dihydroxy benzoic acid 5 (138.8 mg, 0.9 mmol, 5 eq). The vessel was sealed and flushed with argon, after which 4 mL of 250 mM pH 9.0 PBS was added and the reaction was heated to 100° C. for 18 hr. The reaction was cooled and diluted with saturated aqueous NaHCO$_3$ (3 mL), and the solution was directly purified by reversed-phase chromatography (50 g C$_{18}$ Aq, 0→40% acetonitrile/water). The product-containing fractions were genevaced to afford 6 (NIR-890) (131 mg, 64% yield) as a blue solid. $^1$H NMR (500 MHz, methanol-d$_4$) δ 8.62-8.59 (d, 1H), 8.52-8.49 (d, 1H), 7.83-7.75 (m, 6H), 7.26-7.20 (dd, 2H), 7.12-7.10 (d, 1H), 6.20-6.12 (dd, 2H), 4.10-4.03 (m, 4H), 2.85-2.78 (m, 7H), 2.51 (s, 1H), 2.40-2.31 (m, 2H), 2.02-1.99 (m, 2H), 1.92-1.89 (m, 8H), 1.88-1.72 (m, 13H); $^{13}$C NMR (500 MHz, methanol-d$_4$) δ 171.91, 171.49, 170.66, 162.72, 162.22, 151.20, 148.97, 144.00, 143.79, 141.54, 141.10, 140.94, 140.91, 140.60, 139.58, 127.03, 126.75, 126.72, 123.44, 123.30, 121.48, 119.99, 119.94, 119.44, 113.10, 109.90, 109.51, 100.71, 99.97, 50.42, 50.38, 43.61, 43.40, 36.95, 28.86, 27.18, 27.16, 27.14, 27.09, 25.67, 25.60, 23.85, 23.61, 22.25; HRMS (ESI) calculated for $C_{49}H_{51}N_2O_{16}S_4^{3-}$ (M+4H) 1055.21, observed 526.1 (M-2H)$^{-2}$, 350.4 (M-3H)$^{-3}$.

Figure 20:
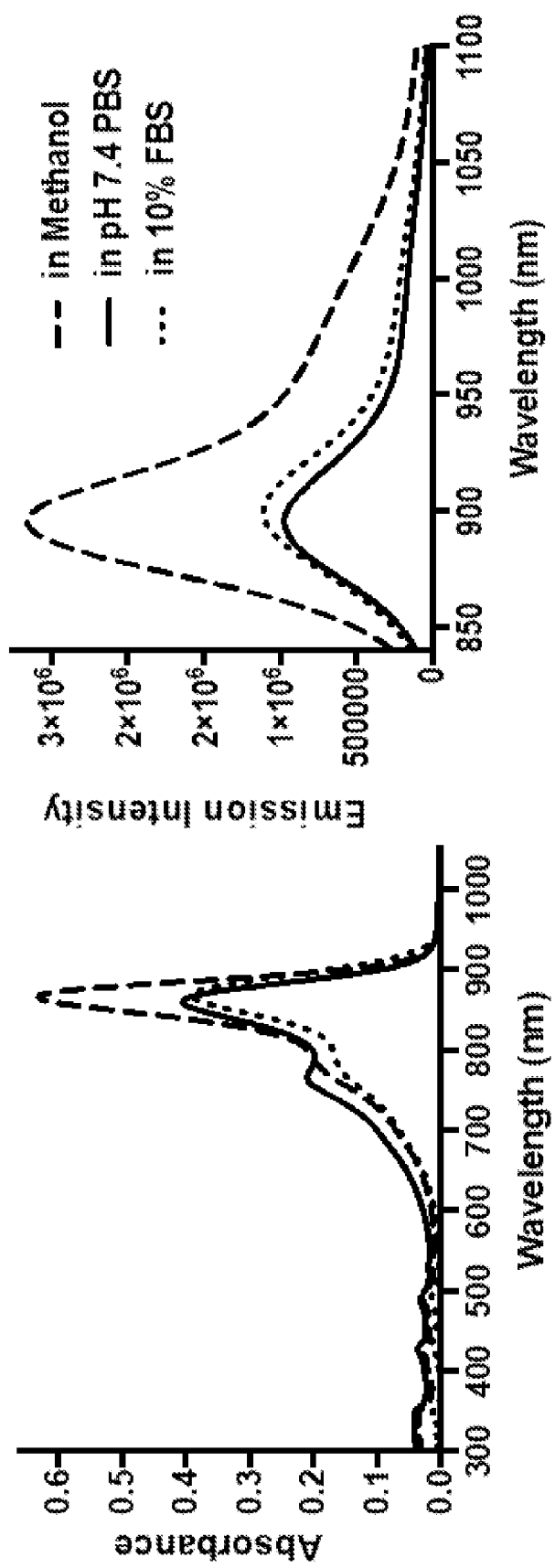
FIG. 20 shows absorbance (left) and emission (right, excitation at 820 nm) spectra of a 2 μM solution of cyanine fluorophore (compound 6, NIR-890) in different solvents as indicated.

FIG. 20 shows absorbance (left) and emission (right) spectra of compound 6 (NIR-890) in different solvents as indicated. Compound 6 exhibited absorbance maximum ($\lambda_{max,\ abs}$) of 860 nm, an emission maximum ($\lambda_{max,\ emiss}$) of 896 nm, and a molar absorptivity (ε, M$^{-1}$cm$^{-1}$) of 191,000 in pH 7.4 PBS, $\lambda_{max,\ abs}$=868 nm, $\lambda_{max,\ emiss}$=896 nm, and ε=192,000 in 10% (v/v) FBS in pH 7.4 PBS, and $\lambda_{max,\ abs}$=866 nm, $\lambda_{max,\ emiss}$=896 nm, and ε=208,000 in methanol.

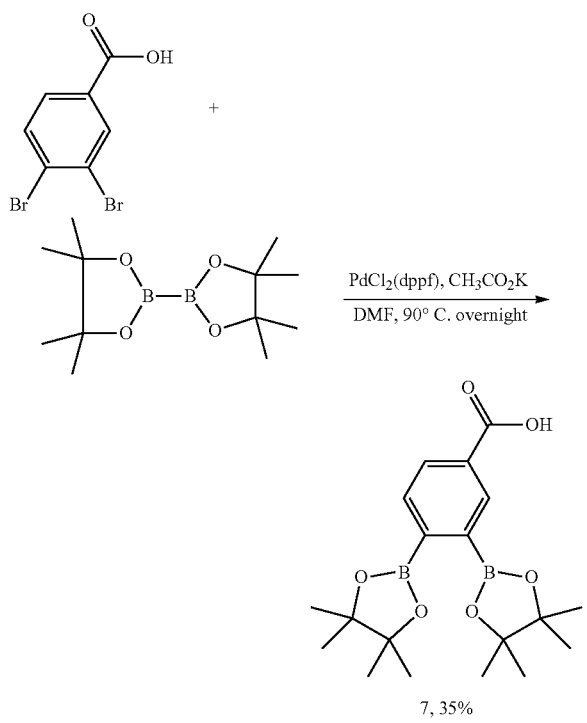

Synthesis of 7: To a microwave vial equipped with a magnetic stir bar was added 3,4-dibromobenzoic acid (500 mg, 1.78 mmol, 1 eq) and bis (pinacol) diborane (4.53 g, 17.86 mmol, 10 eq), potassium acetate (1.75 g, 17.86 mmol, 10 eq) and [1,1'-bis(diphenylphosphino)ferrocene]palladium(II) dichloride [$PdCl_2$(dppf)] (130 mg, 0.0017 mmol, 0.1 eq). The vessel was sealed and flushed with argon. DMF (15 mL) was added and the reaction was heated to 90° C. for 24 h. The solvent was evaporated under reduced pressure and dissolved in 1:1 water and ethyl acetate mixture (100 ml). Separated the ethyl acetate layer and extracted the remaining product from water layer with ethyl acetate (3×50 ml). The combined organic solution was washed with water, dried over $Na_2SO_4$ and concentrated under reduced pressure. The resulting residue was purified by normal-phase chromatography (silica gel column, 0→50% ethyl acetate/hexane), and the product-containing fractions were evaporated to afford compound 7 (233 mg, 35% yield) as a white solid. $^1$H NMR (400 MHz, chloroform-d) δ 8.32 (m, 1H), 8.01 (d, 1H), 7.67-7.65 (dd, 1H), 1.32-1.31 (d, 24H); $^{13}$C NMR (400 MHz, chloroform-d) δ 171.24, 135.03, 133.37, 130.56, 129.35, 84.34, 83.27, 24.92; LCMS calculated for $C_{19}H_{29}B_2O_6$ (M+4H) 374.21, observed 375.0.

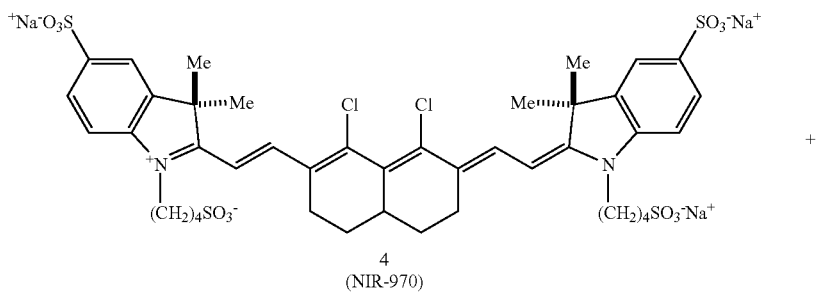

4
(NIR-970)

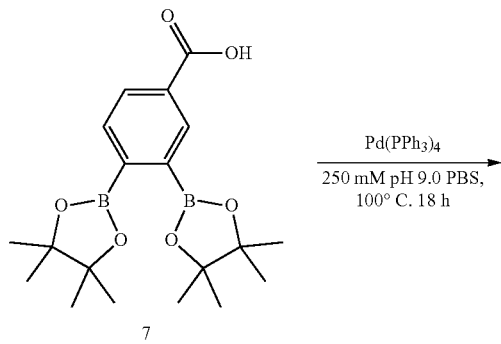

-continued

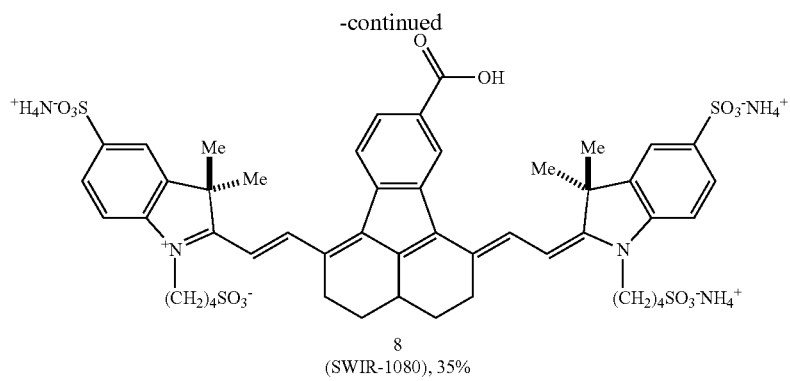

8
(SWIR-1080), 35%

Synthesis of 8 (SWIR-1080): To a microwave vial equipped with a magnetic stir bar was added Compound 4 (110 mg, 0.105 mmol, 1 eq), 7 (198 mg, 0.52 mmol, 5 eq) and Pd(PPh$_3$)$_4$ (12.24 mg, 0.01 mmol, 0.1 eq). The vessel was sealed and flushed with argon. 1 ml of 250 mM pH 9.0 PBS was added and the reaction was heated to 100° C. until product formation (~18 h). The reaction was cooled and diluted with 2 ml of saturated sodium bicarbonate and filtered through celite. purified by reversed-phase chromatography (50 g C$_{18}$ Aq, 0→40% acetonitrile/water). Obtained major product with some impurities so repeated the purification same as above. The product-containing fractions were genevaced to afford 8 (SWIR-1080) (41 mg, 35% yield) as a red solid. $^1$H NMR (400 MHz, methanol-d$_4$) δ 8.78-8.75 (d, 1H), 8.62-8.61 (d, 1H), 8.37-8.34 (d, 1H), 8.05-8.01 (m, 2H), 7.97-7.92 (m, 3H), 7.84-7.82 (d, 1H), 7.53-7.51 (d, 1H), 7.33-7.31 (d, 1H), 6.74-6.70 (d, 1H), 6.47-6.43 (d, 1H), 4.37-4.33 (dd, 2H), 4.21-4.17 (t, 2H), 3.24-3.21 (d, 1H), 2.97-2.93 (m, 4H), 2.72-2.61 (m, 3H), 2.32-2.28 (t, 2H), 2.05-1.97 (m, 12H), 1.91-1.83 (m, 9H), 1.46 (s, 2H); $^{13}$C NMR (500 MHz, methanol-d$_4$) δ 172.68, 169.03, 146.29, 145.54, 144.03, 143.62, 143.47, 142.60, 141.79, 141.21, 140.88, 140.78, 139.95, 138.72, 136.41, 132.68, 131.46, 129.44, 126.91, 126.77, 123.38, 121.85, 119.99, 119.94, 110.98, 109.69, 104.89, 102.25, 50.43, 50.30, 49.50, 44.27, 43.59, 33.33, 29.61-29.46, 26.79, 26.75, 26.65, 26.61, 26.03, 25.90, 25.79, 25.68, 22.28, 22.22; HRMS (ESI) calculated for C$_{49}$H$_{51}$N$_2$O$_{14}$S$_4$$^{3-}$ (M+4H) 1023.22, observed 1022.23 (M−H), 339.74 (M−3H)$^{-3}$, 510.11 (M−2H)$^{-2}$.

Figure 21:
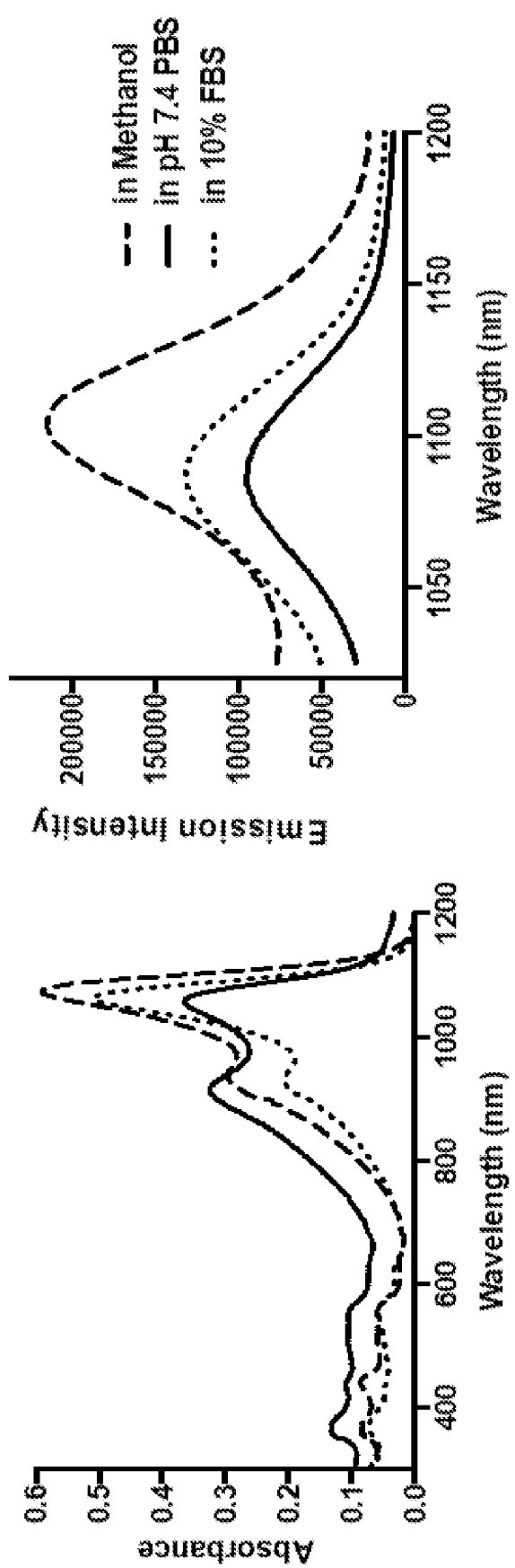
FIG. 21 shows absorbance (left) and emission (right, excitation at 900 nm) spectra of a 5 μM solution of cyanine fluorophore (compound 8, SWIR-1080) in different solvents as indicated.

FIG. 21 shows absorbance (left) and emission (right) spectra of compound 8 (SWIR-1080) in different solvents as indicated. Compound 8 (SWIR-1080) is a water-soluble cyanine fluorophore, exhibited an absorbance maximum ($λ_{max, abs}$) of 1058 nm, an emission maximum ($λ_{max, emiss}$) of 1084 nm, and a molar absorptivity (ε, M$^{-1}$cm$^{-1}$) of 70,000 in pH 7.4 PBS, $λ_{max, abs}$=1062 nm, $λ_{max, emiss}$=1086 nm, and ε=99,000 in 10% (v/v) FBS in pH 7.4 PBS and $λ_{max, abs}$=1072 nm, $λ_{max, emiss}$=1103 nm, and ε=117,000 in methanol.

-continued

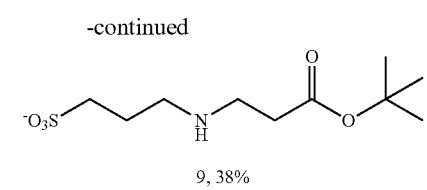

9, 38%

Synthesis of 9: To a microwave vial equipped with a magnetic stir bar was added β-Alanine t-butyl ester hydrochloride (291 mg, 1.60 mmol, 1 eq) and 1,3-propanesultone (220 mg, 1.8 mmol, 1.1 eq). The vessel was sealed and flushed with argon. 4 ml of THF was added and the reaction was heated to 65° C. for 2 h, during which the white colored product precipitated. The reaction mixture was cooled and filtered. The resulting solid was washed with acetone and dried under vacuum to yield 207 mg (38% yield) of compound 9 white flaky solid. $^1$H NMR (400 MHz, water-d$_2$) δ 3.24-3.22 (t, 2H), 3.16-3.13 (m, 2H), 2.94-2.91 (t, 2H), 2.68-2.66 (t, 2H), 2.08-2.04 (m, 2H), 1.38 (s, 9H); $^{13}$C NMR (400 MHz, water-d$_2$) δ 171.37, 83.70, 47.75, 46.36, 42.91, 31.35, 27.11, 21.15; HRMS (ESI) calculated for C$_{10}$H$_{20}$NO$_5$S$^-$ (M+H) 267.11, observed 268.12 (MH)$^+$.

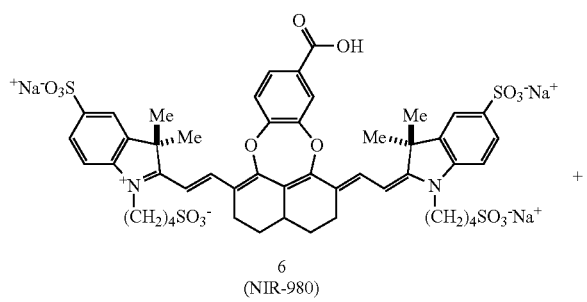

6
(NIR-980)

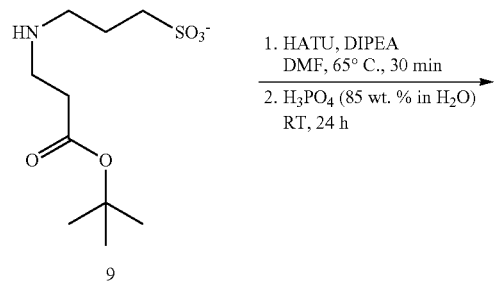

1. HATU, DIPEA
   DMF, 65° C., 30 min
2. H$_3$PO$_4$ (85 wt. % in H$_2$O)
   RT, 24 h

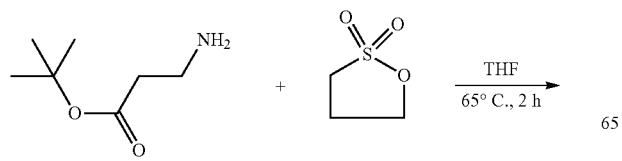

9

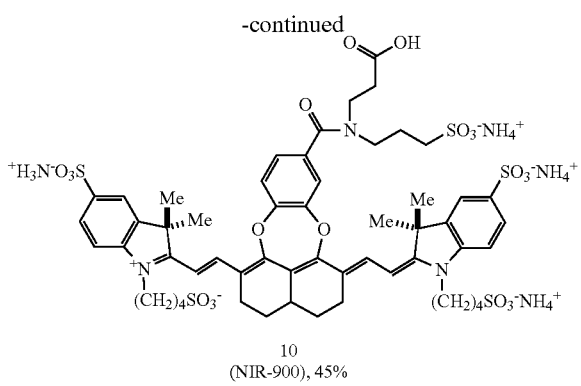

10
(NIR-900), 45%

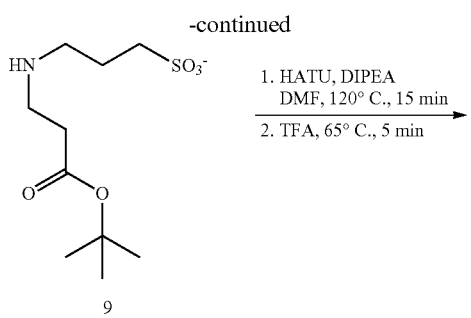

9

Synthesis of 10 (NIR-900): To a microwave vial equipped with a magnetic stir bar was added Compound 6 (110 mg, 0.098 mmol, 1 eq), compound 9 (78.29 mg, 0.29 mmol, 3 eq), and HATU (111.92 mg, 0.29 mmol, 2 eq). The vessel was sealed and flushed with argon. DMF (1.5 mL) and DIPEA (85.68 μL, 0.49 mmol, 5 eq) was added and the reaction was heated to 65° C. for 30 min. The reaction mixture was cooled and precipitated into ether via centrifugation (12 ml). The precipitated brown solid was transferred to a microwave vial with 2 mL phosphoric acid (85 weight % in water) and stirred at RT until tert-butyl deprotection occurred (~24 hr). The reaction was diluted 5 mL of saturated sodium bicarbonate, and directly purified by reversed-phase chromatography (50 g $C_{18}$ Aq, 0→40% acetonitrile/water). The product-containing fractions were genevaced to afford 10 (NIR-900) (58.5 mg, 45% yield) as a green solid. $^1$H NMR (400 MHz, methanol-$d_4$) δ 8.68-8.62 (dd, 2H), 7.96-7.89 (m, 4H), 7.40-7.34 (q, 5H), 6.34-6.27 (dd, 2H), 4.24-4.18 (m, 4H), 3.81-3.67 (d, 4H), 2.99-2.92 (m, 8H), 2.68-2.64 (m, 6H), 2.15-2.13 (d, 3H), 2.03-1.98 (m, 10H), 1.90-1.85 (m, 12H); $^{13}$C NMR (500 MHz, methanol-$d_4$) δ 172.77, 169.00, 167.93, 146.51, 145.67, 144.09, 143.64, 143.49, 142.57, 141.89, 141.22, 140.90, 140.79, 139.96, 138.73, 136.43, 132.70, 131.47, 129.45, 126.92, 126.78, 123.39, 121.86, 120.01, 119.95, 111.00, 109.70, 104.90, 102.26, 50.44, 50.31, 49.51, 44.27, 43.59, 33.33, 29.61, 29.47, 26.80, 26.76, 26.65, 26.61, 26.04, 25.90, 25.80, 25.68, 22.28, 22.22; HRMS (ESI) calculated for $C_{55}H_{61}N_3O_{20}S_5^{4-}$ (M+5H) 1248.25, observed 1247.27 (M−H), 310.81 (M−4H)$^{-4}$, 414.75 (M−3H)$^{-3}$, 622.63 (M−2H)$^{-2}$.

FIG. 22 shows absorbance (left) and emission (right) spectra of compound 10 (NIR-900) in different solvents as indicated. Compound 10 (NIR-900) exhibited absorbance maximum ($\lambda_{max,\ abs}$) of 862 nm, an emission maximum ($\lambda_{max,\ emiss}$) of 896 nm, and a molar absorptivity (ε, $M^{-1}cm^{-1}$) of 145,000 in pH 7.4 PBS, $\lambda_{max,\ abs}$=871 nm, $\lambda_{max,\ emiss}$=900 nm, and ε=137,000 in 10% (v/v) FBS in pH 7.4 PBS, and $\lambda_{max,\ abs}$=869 nm, $\lambda_{max,\ emiss}$=896 nm, and ε=187,000 in methanol.

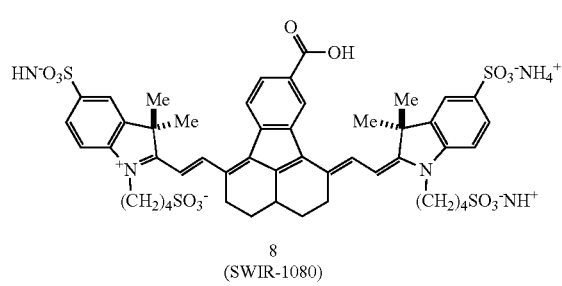

8
(SWIR-1080)

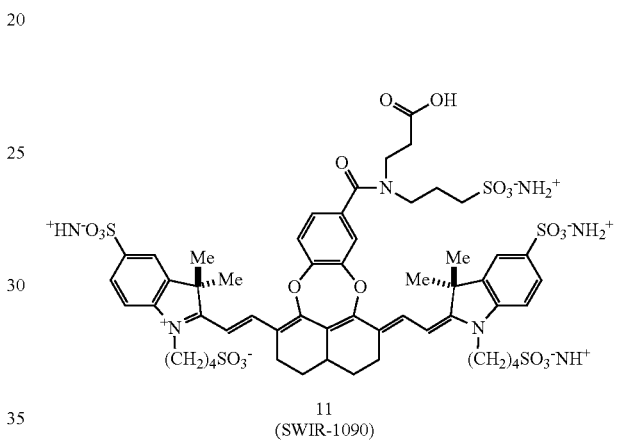

11
(SWIR-1090)

Synthesis of 11 (SWIR-1090): To a microwave vial equipped with a magnetic stir bar was added Compound 8 (2 mg, 0.0018 mmol, 1 eq), compound 9 (2.39 mg, 0.009 mmol, 5 eq), and HATU (2.05 mg, 0.0054 mmol, 3 eq). The vessel was sealed and flushed with argon. DMF (150 μL) and DIPEA (0.94 μL, 0.0054 mmol, 3 eq) were added and the reaction was heated to 120° C. for 15 min. The reaction mixture was cooled and precipitated into ether (10 ml) and centrifuged. Precipitated brown solid was transferred into a microwave reaction vial sealed and stirred with 10 μL TFA at 65° C. for 10 min. TFA was removed under reduced pressure, and the reaction was diluted with water and directly purified by reversed-phase chromatography (prep isco, 0→50% acetonitrile/2 mM ammonium bicarbonate in water). The product-containing fractions were evaporated to afford 11 (SWIR-1090) (0.8 mg, 22% yield) as a red solid. $^1$H NMR (500 MHz, methanol-$d_4$) δ; LCMS calculated for $C_{55}H_{61}N_3O_{18}S_5^{4-}$ (M+5H) 1216.40, observed 303.1 (M/4+1).

Figure 23:
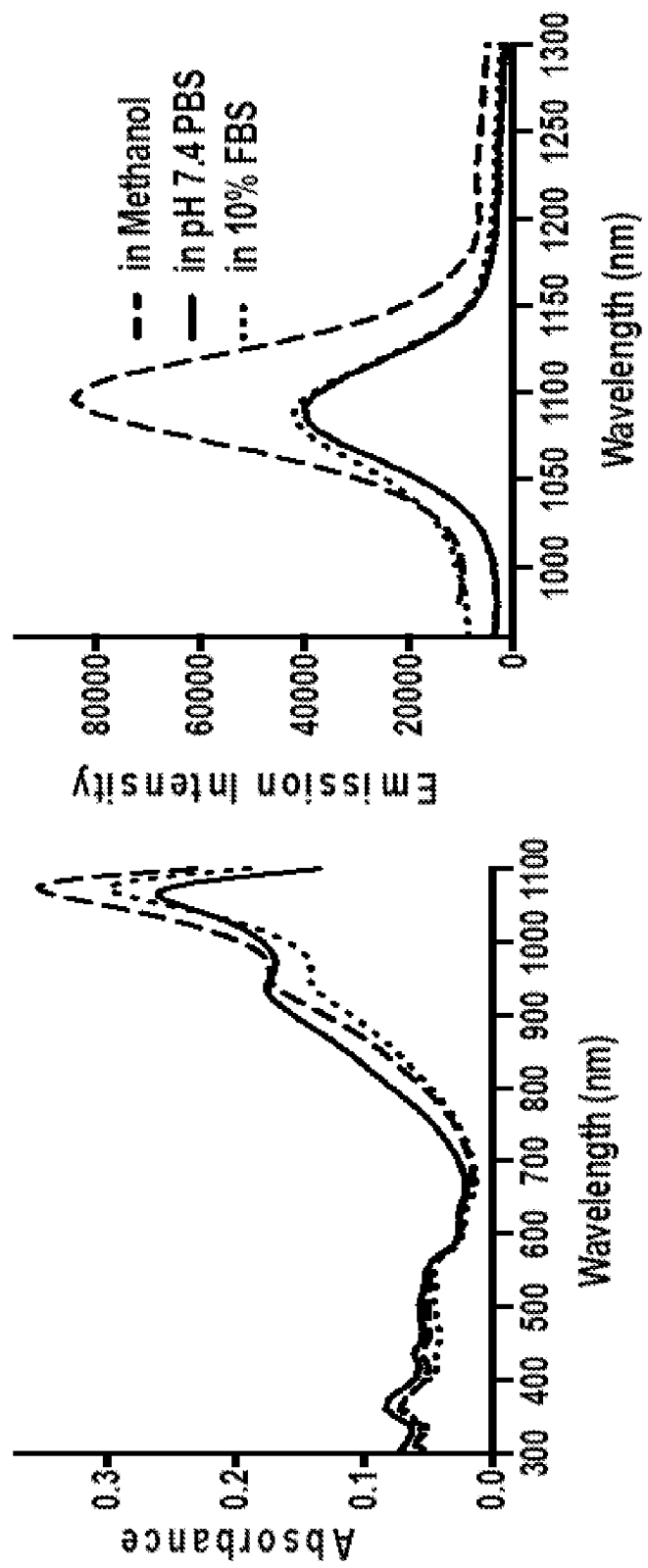
FIG. 23 shows absorbance (left) and emission (right, excitation at 900 nm) spectra of a 5 μM solution of cyanine fluorophore (compound 11, SWIR-1090) in different solvents as indicated.

FIG. 23 shows absorbance (left) and emission (right) spectra of compound 11 (SWIR-1090) in different solvents as indicated. Compound 11 (SWIR-1090) exhibited an absorbance maximum ($\lambda_{max,\ abs}$) of 1065 nm, an emission maximum ($\lambda_{max,\ emiss}$) of 1090 nm, and a molar absorptivity (ε, $M^{-1}cm^{-1}$) of 38,000 in pH 7.4 PBS, $\lambda_{max,\ abs}$=1074 nm, $\lambda_{max,\ emiss}$=1090 nm, and ε=37,000 in 10% (v/v) FBS in pH 7.4 PBS, and $\lambda_{max,\ abs}$=1074 nm, $\lambda_{max,\ emiss}$=1096 nm, and ε=72,000 in methanol.

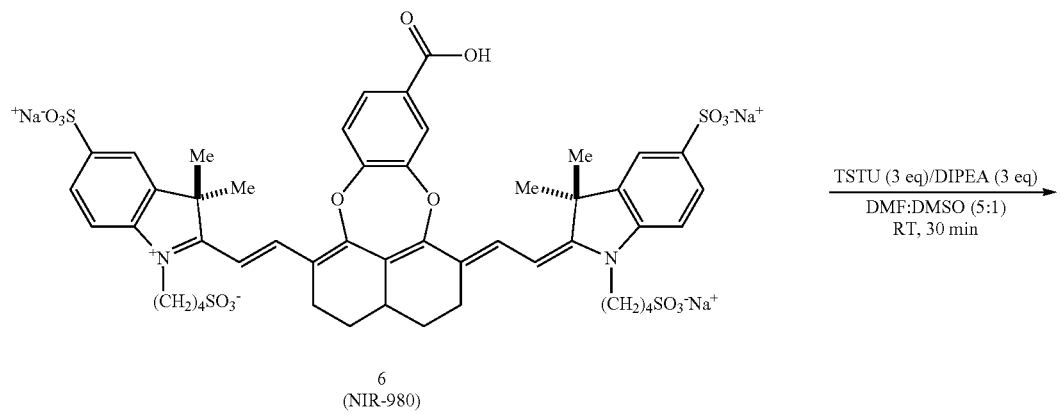

6
(NIR-980)

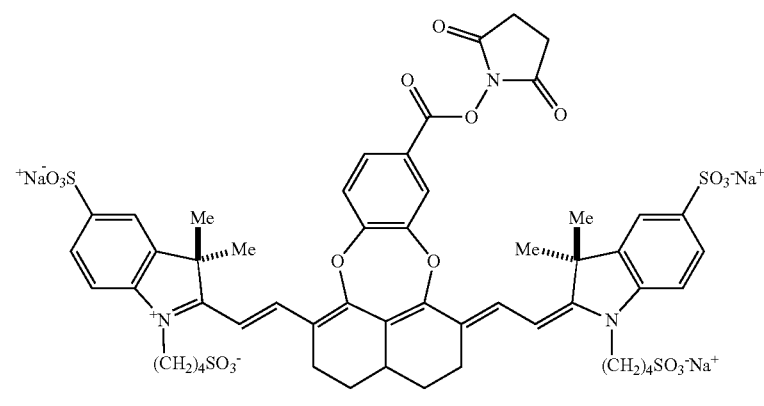

6a, 93%

Synthesis of 6a: To a 1.5 ml Eppendorf® tube which has compound 6 (3.96 mg, 0.0035 mmol, 1 eq) added TSTU (3.19 mg, 0.01 mmol, 3 eq), DIPEA (1.82 µL, 0.01 mmol, 3 eq) and DMF:DMSO (300 µL, 5:1), were added and stirred at room temperature under argon. LCMS showed complete conversion to NHS product in 30 min. The reaction was inversely added to diethyl ether (10 mL) resulting in a green precipitate. After centrifugation the solid was placed under vacuum for 2 hour, yielding 6a (4 mg, 93% yield) as green coloured solid. LCMS calculated for $C_{53}H_{54}N_3O_{18}S_4^{3-}$ $(M-3H)^{3-}$ 382.74, observed 383.

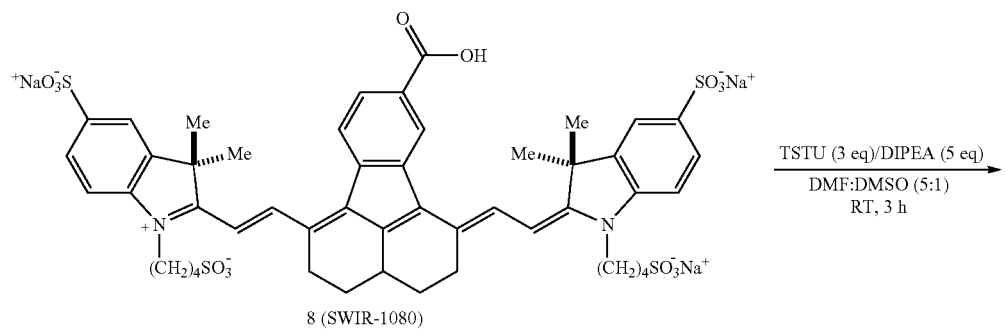

8 (SWIR-1080)

-continued

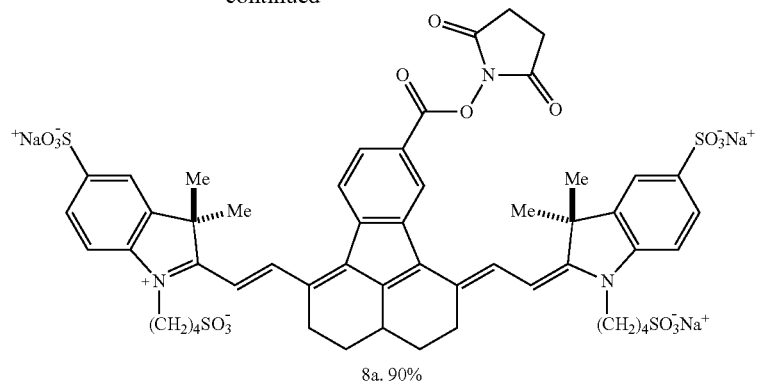

8a. 90%

Synthesis of 8a: To a 1.5 ml Eppendorf® tube which has compound 8 (6.5 mg, 0.006 mmol, 1 eq) added TSTU (5.38 mg, 0.0179 mmol, 3 eq), DIPEA (5.2 μL, 0.029 mmol, 5 eq) and DMF:DMSO (300 μL, 5:1), were added and stirred at room temperature under argon. LCMS showed complete conversion to NHS product in 3 h. The reaction mixture was added to diethyl ether (10 mL) resulting in a green precipitate. After centrifugation the solid was placed under vacuum for 2 hour, yielding 8a (5 mg, 70% yield) as redish solid. LCMS calculated for $C_{49}H_{51}N_2O_{14}S_4$ $(M-3H)^{3-}$ 372.08, observed 372.

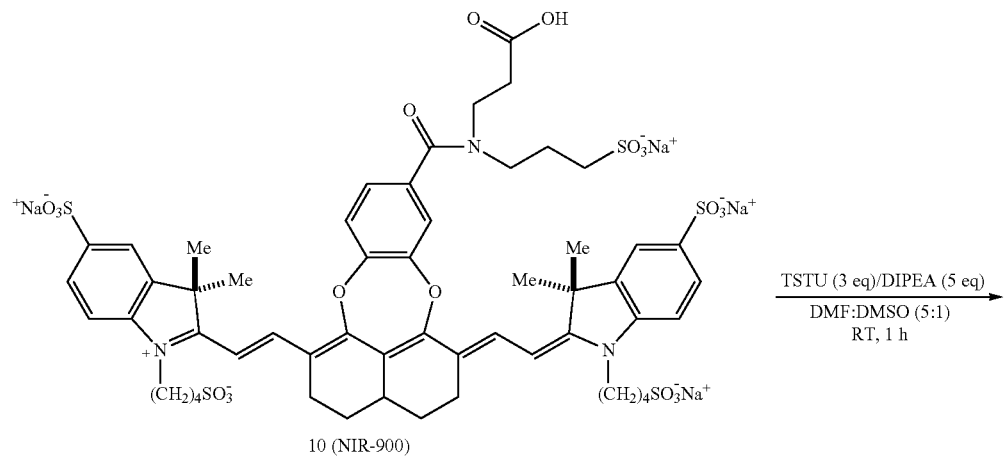

10 (NIR-900)

TSTU (3 eq)/DIPEA (5 eq)
DMF:DMSO (5:1)
RT, 1 h

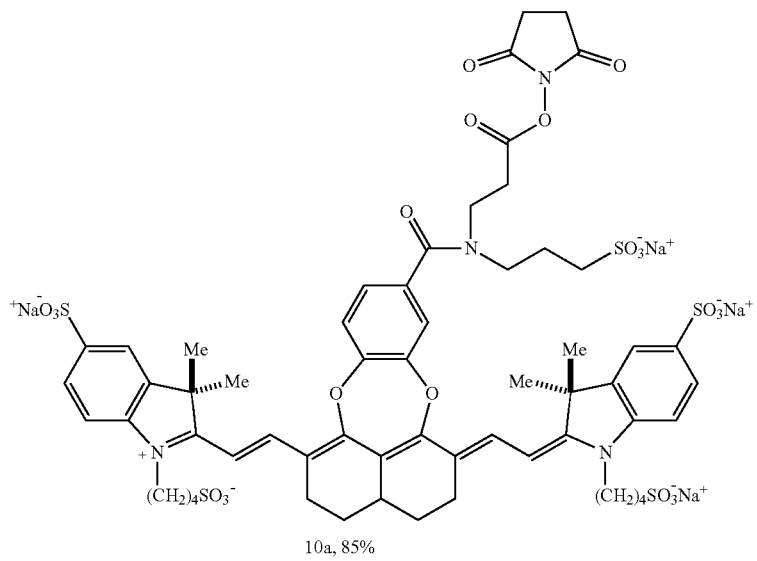

10a, 85%

Synthesis of 10a: To a 1.5 ml Eppendorf® tube which has compound 10 (13 mg, 0.009 mmol, 1 eq) added TSTU (8.79 mg, 0.029 mmol, 3 eq), DIPEA (8.5 µL, 0.048 mmol, 5 eq) and DMF:DMSO (500 µL, 5:1), were added and stirred at room temperature under argon. LCMS showed complete conversion to NHS product in 1 h. The reaction mixture was added to diethyl ether (10 mL) resulting in a green precipitate. After centrifugation the solid was placed under vacuum for 2 hour, yielding 10a (12 mg, 85% yield) as green coloured solid. LCMS calculated for $C_{59}H_{64}N_4O_{22}S_5^{4-}$ $(M-4H)^{4-}$ 335.07, observed 335.

Example 2

Additional Cyanine Fluorophores

Additional cyanine fluorophores as disclosed herein were synthesized and characterized.

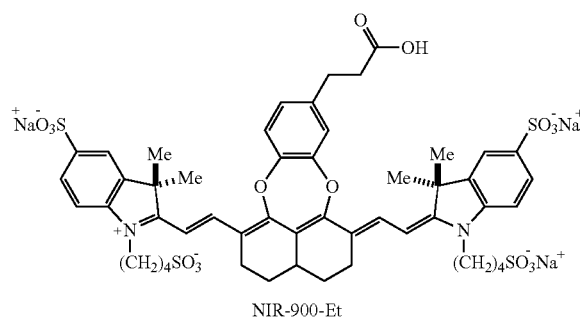

NIR-900-Et

Figure 24:
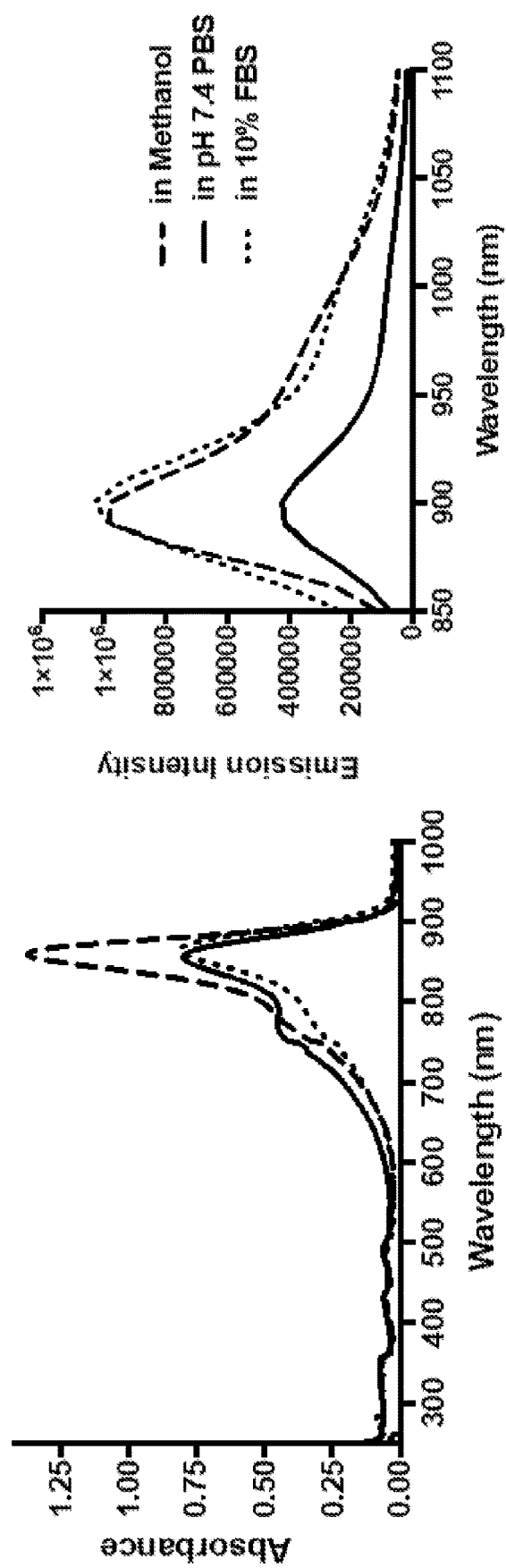
FIG. 24 shows absorbance (left) and emission (right, excitation at 860 nm) spectra of a 5 μM solution of cyanine fluorophore (NIR-900-Et) in different solvents as indicated.

FIG. 24 shows absorbance (left) and emission (right) spectra of NIR-900-Et in different solvents as indicated. It exhibits an absorbance maximum ($\lambda_{max,\ abs}$) of 856 nm, an emission maximum ($\lambda_{max,\ emiss}$) of 900 nm, and a molar absorptivity ($\varepsilon$, $M^{-1}cm^{-1}$) of 172,000 in pH 7.4 PBS, $\lambda_{max,\ abs}$ of 864 nm, $\lambda_{max,\ emiss}$ of 900 nm, and $\varepsilon$ of 148,000 in 10% (v/v) FBS in pH 7.4 PBS, and $\lambda_{max,\ abs}$ of 860 nm, $\lambda_{max,\ emiss}$ of 890 nm, and $\varepsilon$ of 253,000 in methanol.

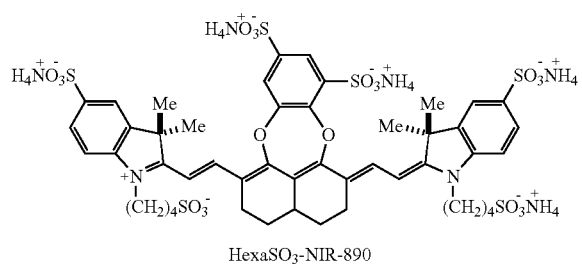

HexaSO₃-NIR-890

Figure 25:
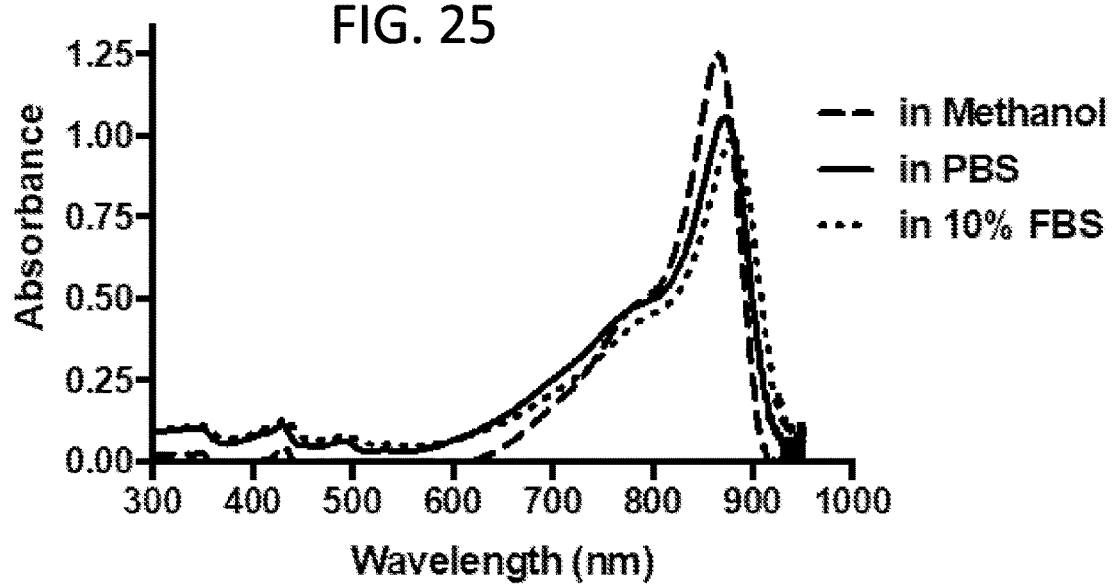
FIG. 25 shows absorbance spectra of a cyanine fluorophore (HexaSO$_3$-NIR-890) in different solvents as indicated.

FIG. 25 shows absorbance spectra of HexaSO₃-NIR-890 in different solvents as indicated.

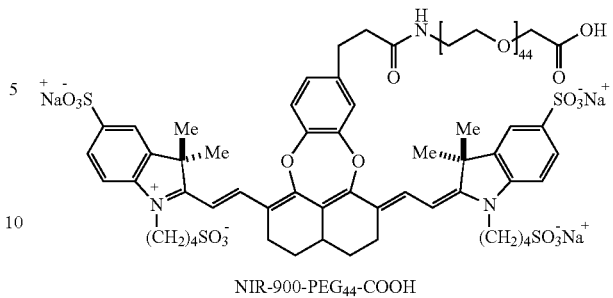

NIR-900-PEG₄₄-COOH

Figure 26:
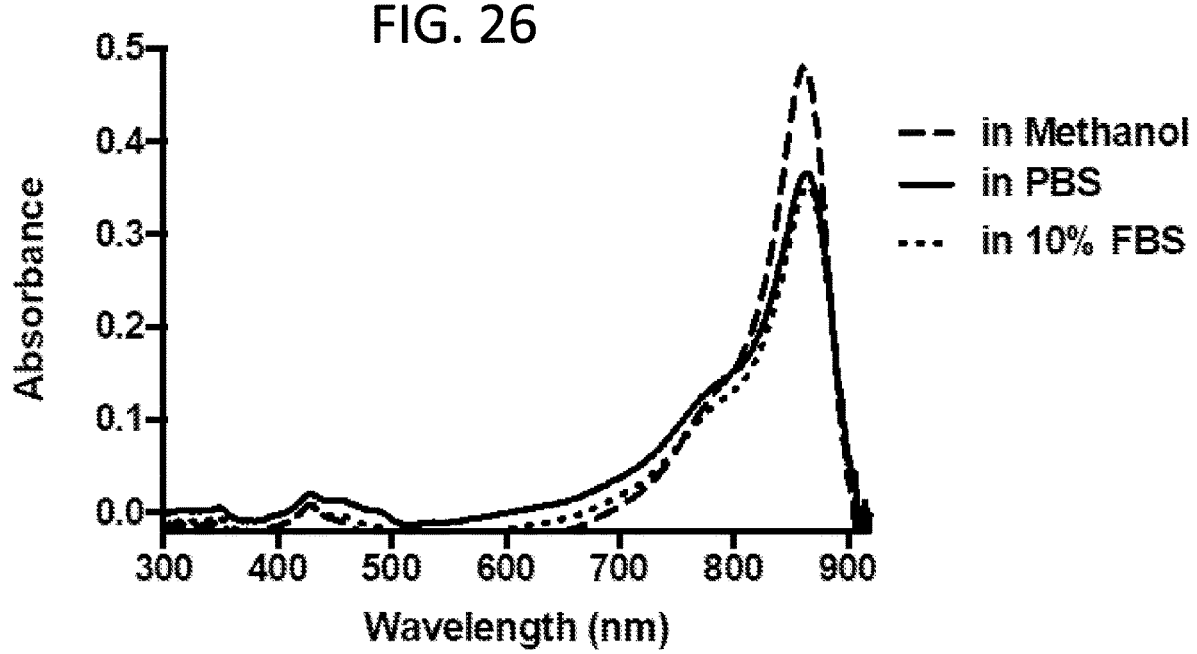
FIG. 26 shows absorbance spectra of a cyanine fluorophore (NIR-900-PEG$_{44}$-COOH) in different solvents as indicated.

FIG. 26 shows absorbance spectra of NIR-900-PEG₄₄-COOH in different solvents as indicated.

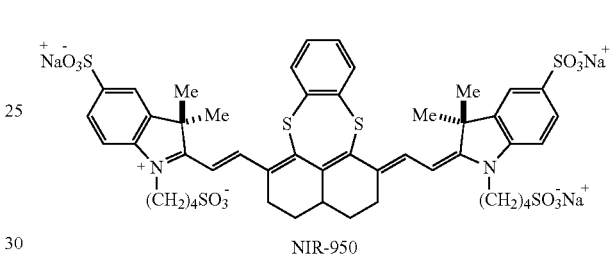

NIR-950

Figure 27:
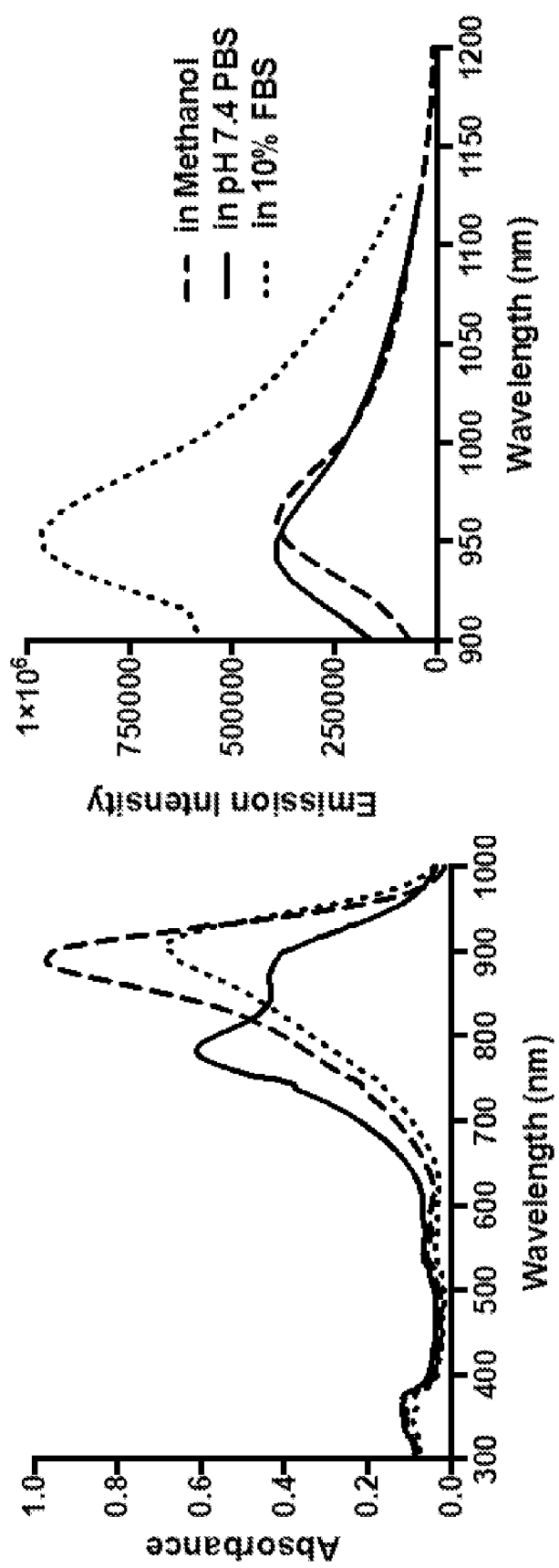
FIG. 27 shows absorbance (left) and emission (right, excitation at ~890 nm) spectra of a 5 μM solution of cyanine fluorophore (NIR-950) in different solvents as indicated.

FIG. 27 shows absorbance (left) and emission (right) spectra of NIR-950. It exhibits an absorbance maximum ($\lambda_{max,\ abs}$) of 880 nm, an emission maximum ($\lambda_{max,\ emiss}$) of 950 nm, and a molar absorptivity ($\varepsilon$, $M^{-1}cm^{-1}$) of 79,000 in pH 7.4 PBS, $\lambda_{max,\ abs}$ of 902 nm, $\lambda_{max,\ emiss}$ of 955 nm, and $\varepsilon$ of 128,000 in 10% (v/v) FBS in pH 7.4 PBS, and $\lambda_{max,\ abs}$ of 890 nm, $\lambda_{max,\ emiss}$ of 960 nm, and $\varepsilon$ of 193,000 in methanol.

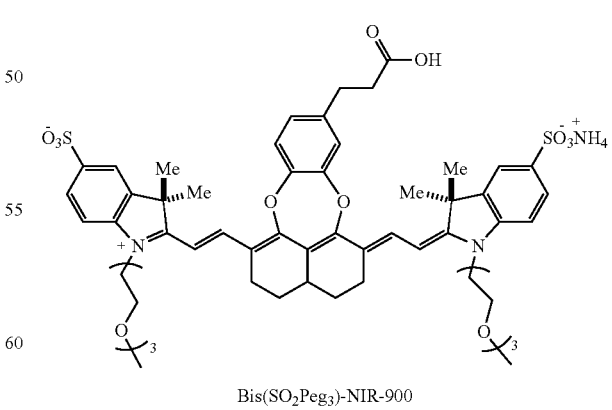

Bis(SO₂Peg₃)-NIR-900

Figure 28:
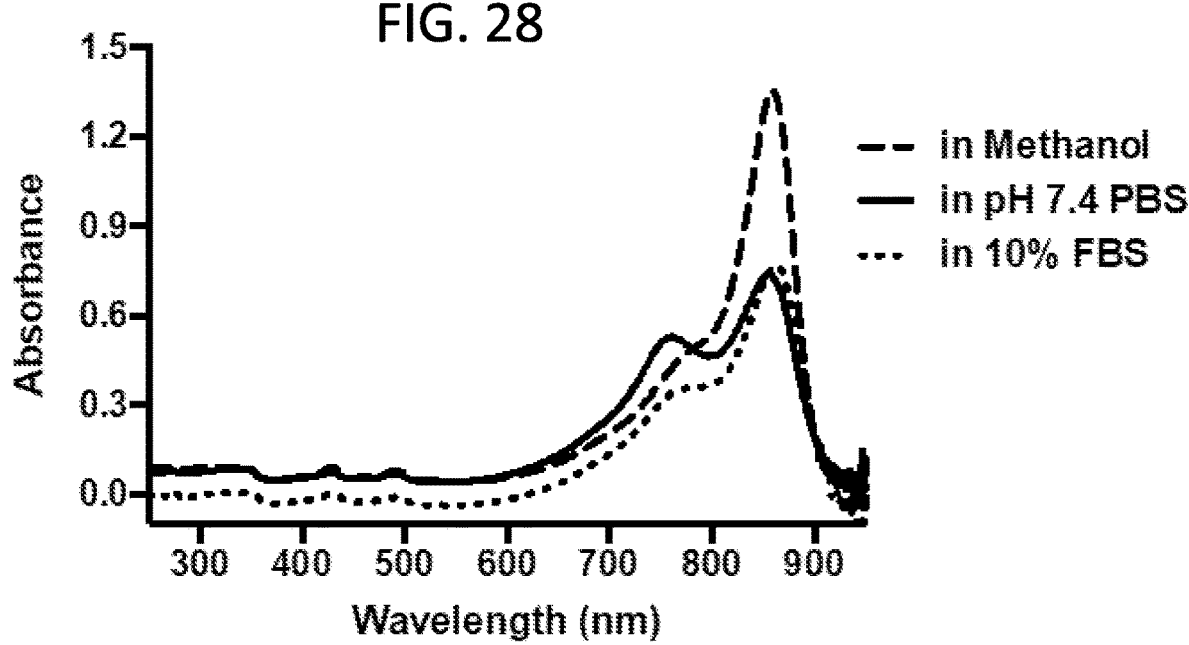
FIG. 28 shows absorbance spectra of a cyanine fluorophore (Bis(SO$_3$Peg$_3$)-NIR-900) in different solvents as indicated.

FIG. 28 shows absorbance spectra of Bis(SO₃Peg₃)-NIR-900 in different solvents as indicated.

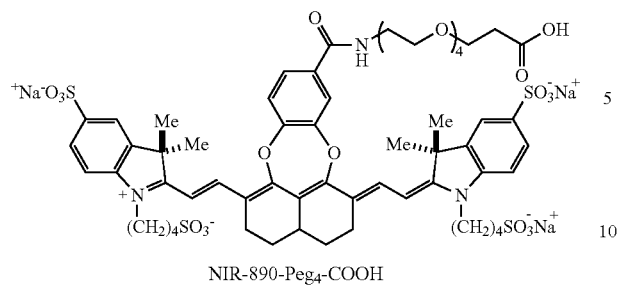

NIR-890-Peg4-COOH

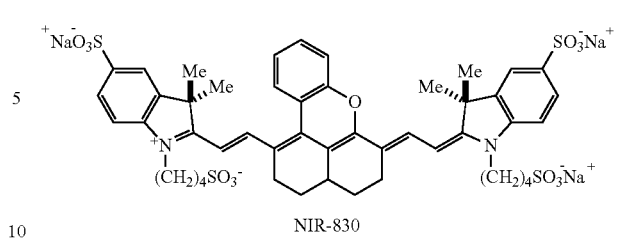

NIR-830

Figure 29:
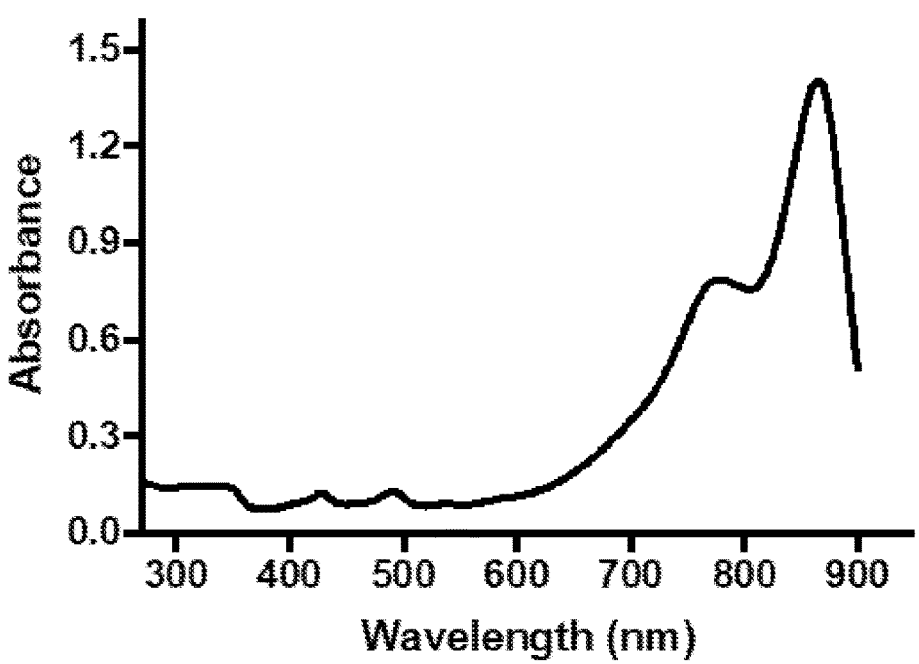
FIG. 29 shows an absorbance spectrum of a cyanine fluorophore (NIR-890-Peg$_4$-COOH) in pH 7.4 PBS.

FIG. 29 shows the absorbance spectrum of NIR-890-Peg4-COOH in pH 7.4 PBS.

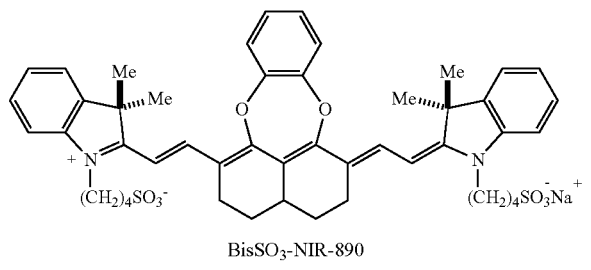

BisSO3-NIR-890

Figure 30:
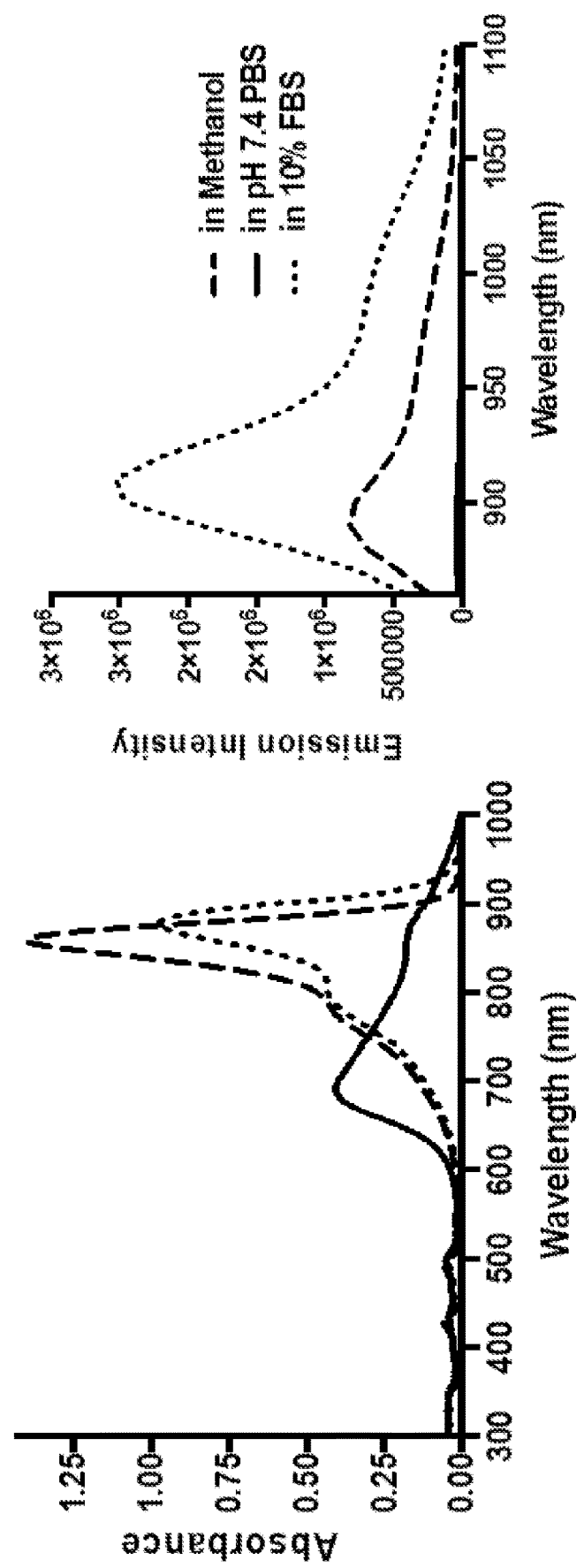
FIG. 30 shows absorbance (left) and emission (right, excitation at ~860 nm) spectrum of a cyanine fluorophore (BisSO$_3$-NIR-890) in different solvents as indicated.

FIG. 30 shows absorbance (left) and emission (right) spectra of BisSO3-NIR-890. It exhibits an absorbance maximum ($\lambda_{max,\ abs}$) of 860 nm, an emission maximum ($\lambda_{max,\ emiss}$) of 890 nm, and a molar absorptivity ($\varepsilon$, $M^{-1}cm^{-1}$) of 275,000 in methanol, $\lambda_{max,\ abs}$ of 689 nm, $\lambda_{max,\ emiss}$ of 890 nm, in PBS and $\lambda_{max,\ abs}$ of 877 nm, $\lambda_{max,\ emiss}$ of 900 nm, and $\varepsilon$ of 187,000 in 10% FBS.

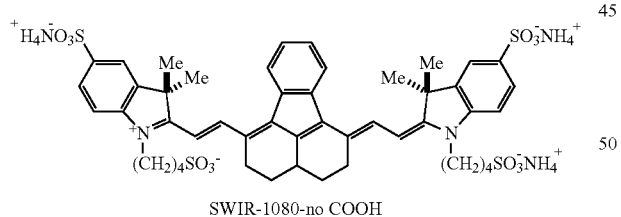

SWIR-1080-no COOH

Figure 31:
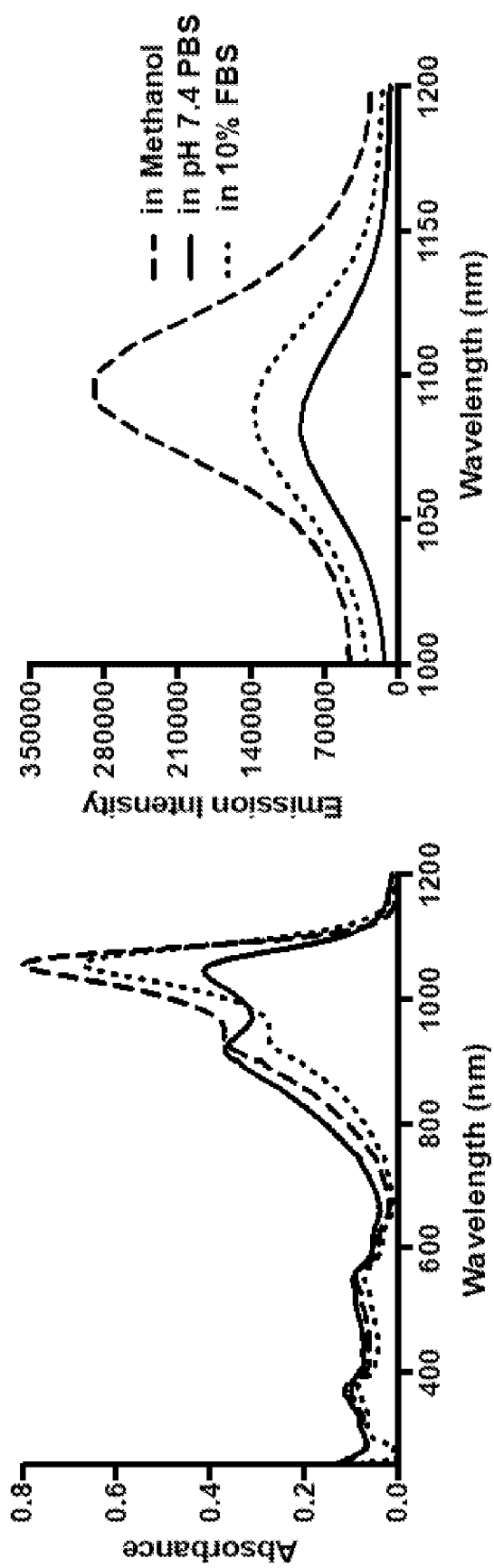
FIG. 31 shows absorbance (left) and emission (right, excitation at 900 nm) spectrum of 5 μM cyanine fluorophore solution (SWIR-1080-no COOH) in different solvents as indicated.

FIG. 31 shows absorbance (left) and emission (right) spectra of SWIR-1080-no COOH in different solvents as indicated. It exhibits an absorbance maximum ($\lambda_{max,\ abs}$) of 1046 nm, an emission maximum ($\lambda_{max,\ emiss}$) of 1080 nm, and a molar absorptivity ($\varepsilon$, $M^{-1}cm^{-1}$) of 76,000 in pH 7.4 PBS, and $\lambda_{max,\ abs}$ of 1056 nm, $\lambda_{max,\ emiss}$ of 1090 nm, and $\varepsilon$ of 131,000 in 10% (v/v) FBS in pH 7.4 PBS, and $\lambda_{max,\ abs}$ of 1056 nm, $\lambda_{max,\ emiss}$ of 1100 nm, and $\varepsilon$ of 154,000 in methanol.

Figure 32:
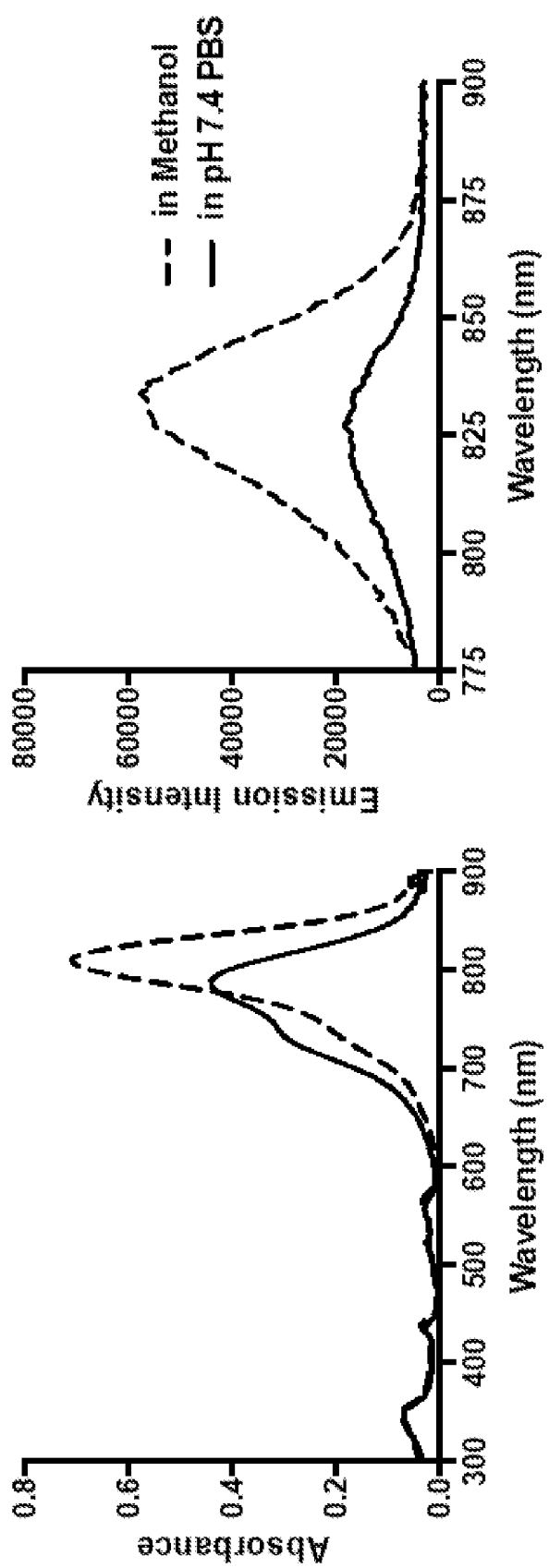
FIG. 32 shows absorbance (left) and emission (right, excitation at 770 nm) spectrum of a cyanine fluorophore solution (NIR-830) in different solvents as indicated.

FIG. 32 shows absorbance (left) and emission (right) spectra of NIR-830 in different solvents as indicated. It exhibits an absorbance maximum ($\lambda_{max,\ abs}$) of 810 nm and an emission maximum ($\lambda_{max,\ emiss}$) of 830 nm in methanol, and $\lambda_{max,\ abs}$ of 790 nm and $\lambda_{max,\ emiss}$ of 830 nm in pH 7.4 PBS.

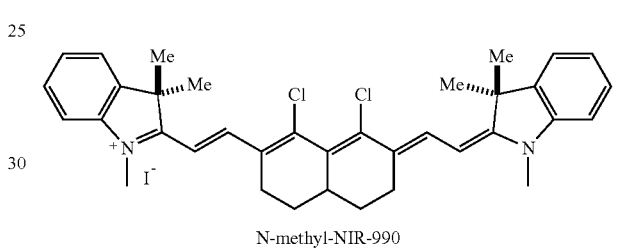

N-methyl-NIR-990

Figure 33:
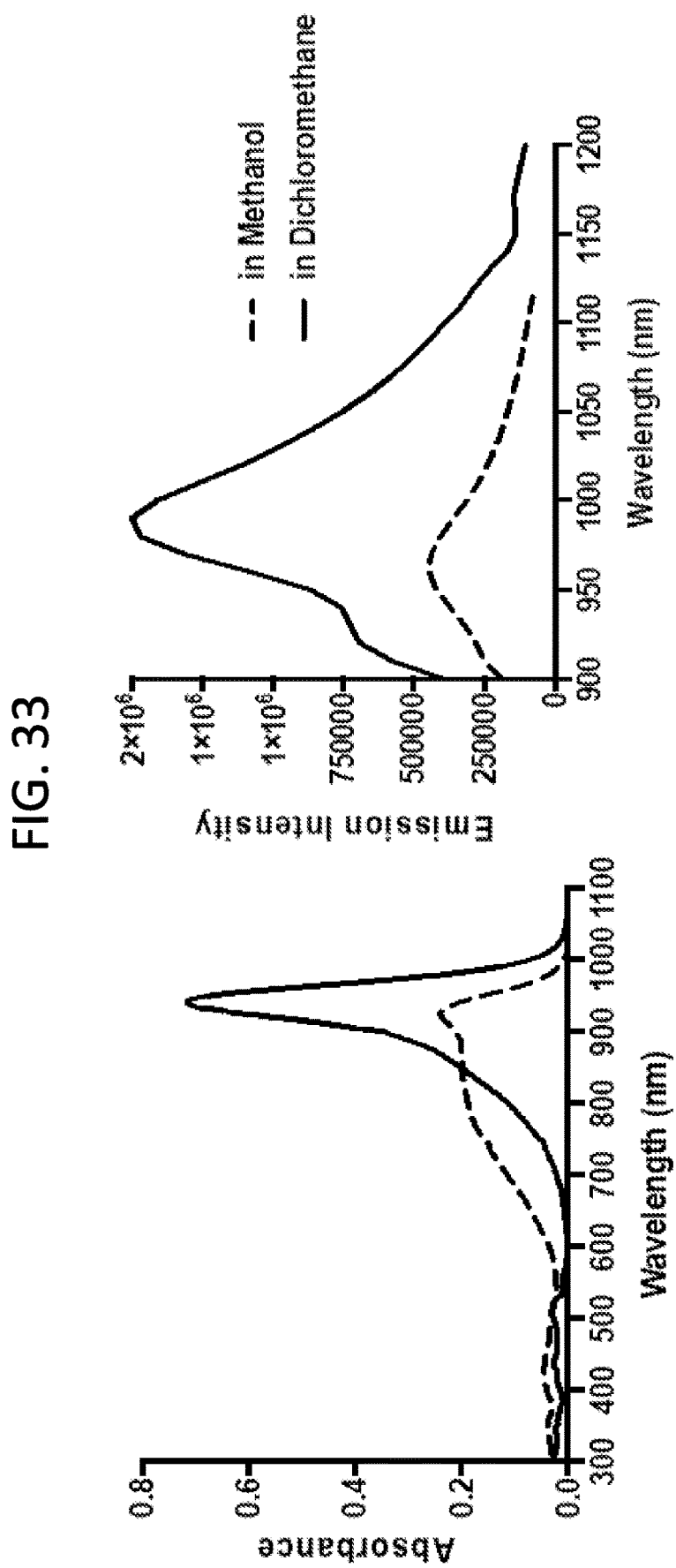
FIG. 33 shows absorbance (left) and emission (right, excitation at 900 nm) spectrum of a cyanine fluorophore solution (N-methyl-NIR-990) in different solvents as indicated.

FIG. 33 shows absorbance (left) and emission (right) spectra of N-methyl-NIR-990 in different solvents as indicated. N-methyl-NIR-990 an organic soluble cyanine fluorophore, exhibits an absorbance maximum ($\lambda_{max,\ abs}$) of 940 nm, an emission maximum ($\lambda_{max,\ emiss}$) of 990 nm, and a molar absorptivity ($\varepsilon$, $M^{-1}cm^{-1}$) of 134,658 in dichloromethane, and $\lambda_{max,\ abs}$ of 922 nm, $\lambda_{max,\ emiss}$ of 960 nm, and $\varepsilon$ of 46,886 in methanol.

Example 3

Antibody-Cyanine Fluorophore Conjugates

Figure 35:
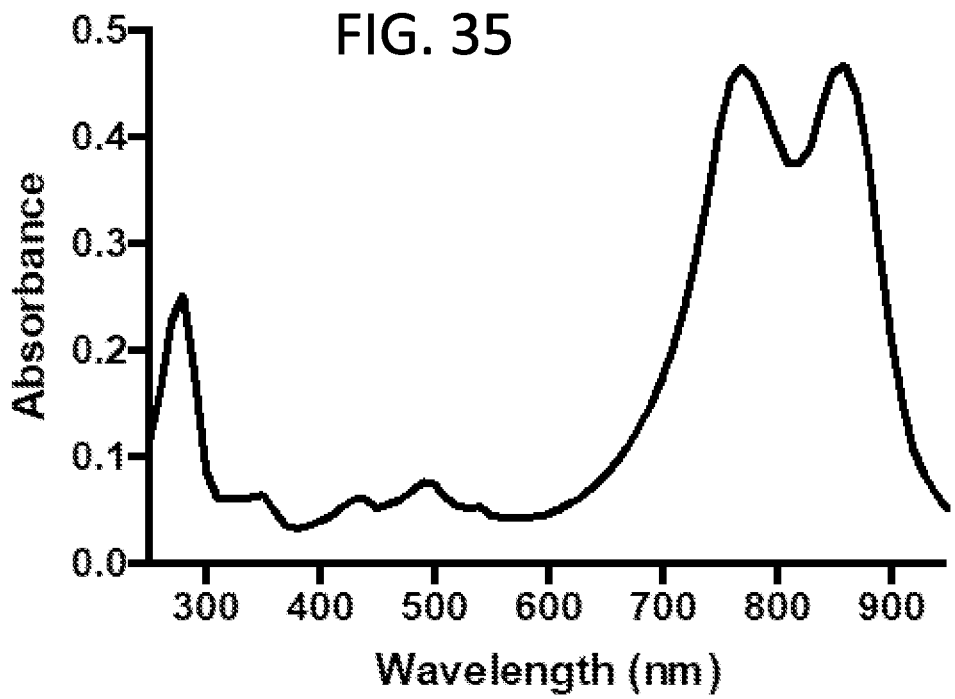
FIG. 35 is an absorbance spectrum of an antibody conjugate of a cyanine fluorophore (NIR-900-Et-Panitumumab) in pH 7.4 PBS.
Figure 36:
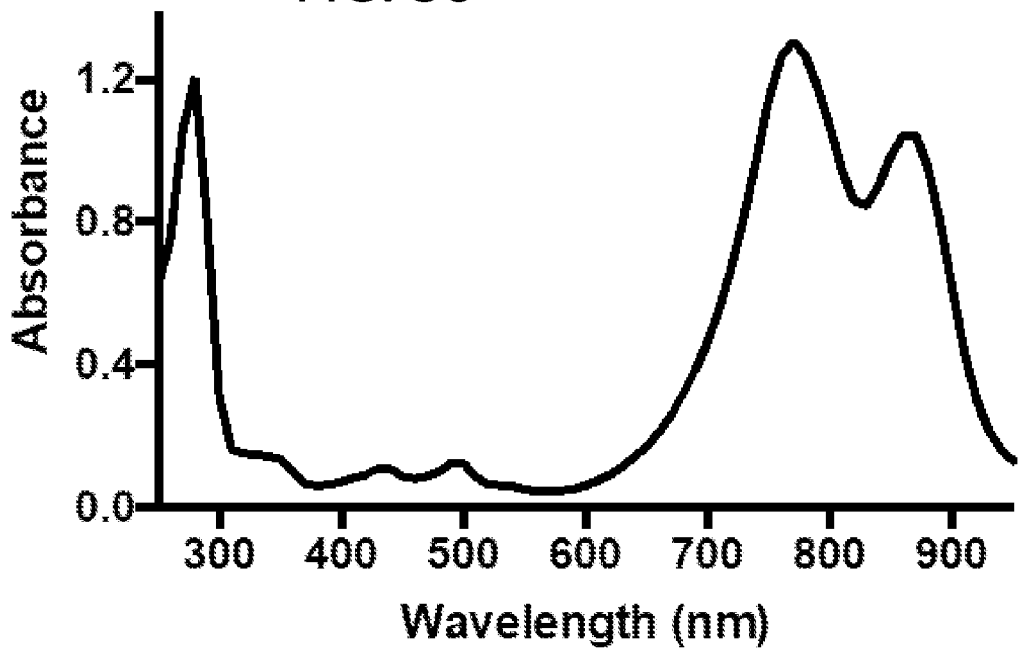
FIG. 36 is an absorbance spectrum of an antibody conjugate of a cyanine fluorophore (NIR-890-Peg$_4$-Panitumumab) in pH 7.4 PBS.
Figure 37:
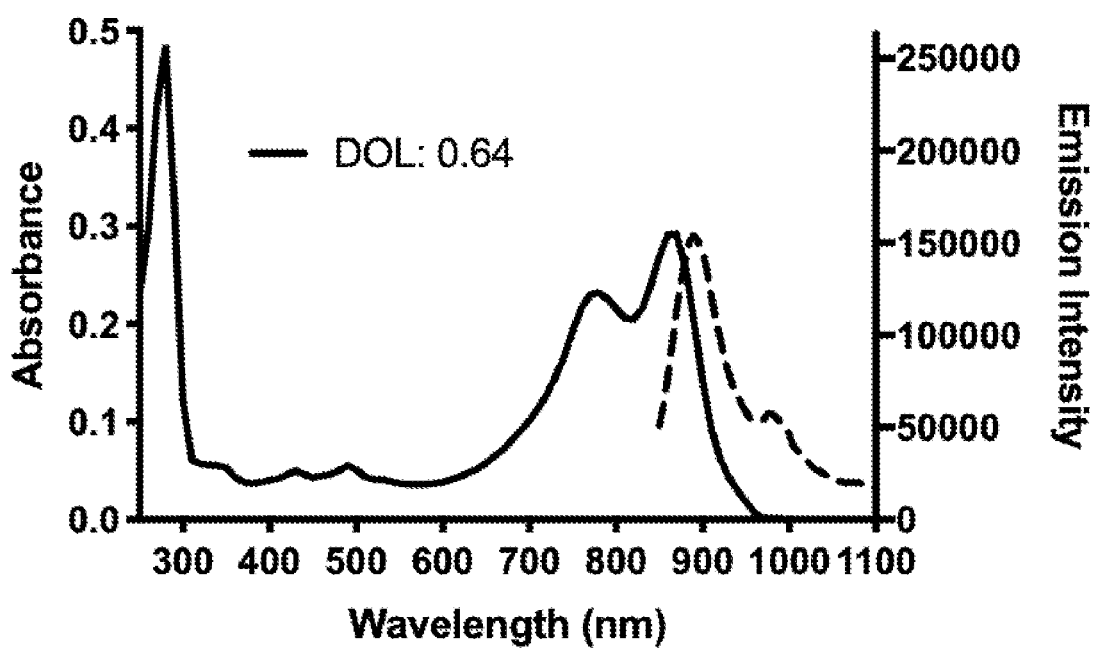
FIG. 37 is an absorbance (solid line) and emission (dashed line, excitation at 820 nm) spectrum of an antibody conjugate of a cyanine fluorophore (compound 6, NIR-890-Panitumumab) in pH 7.4 PBS.
Figure 38:
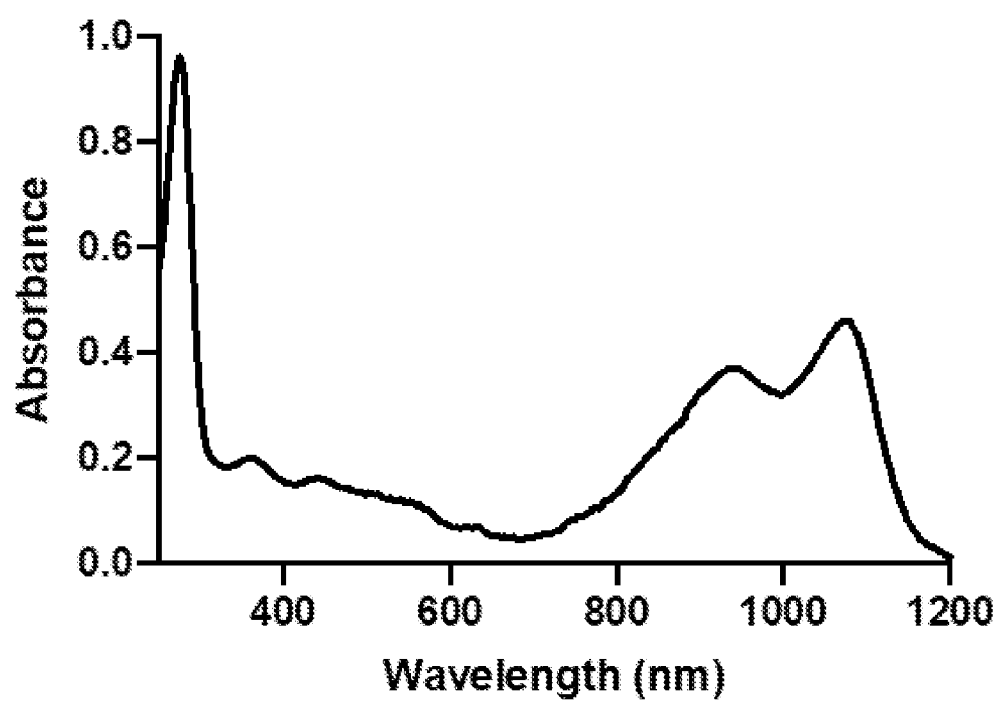
FIG. 38 is absorbance (solid line) spectrum of an antibody conjugate of a cyanine fluorophore (SWIR-1080-Panitumumab) in pH 7.4 PBS.

Several antibody-cyanine fluorophore conjugates were prepared and characterized. Panitumumab antibodies were conjugated to activated esters of compounds NIR-890, NIR-900, SWIR-1080, SWIR-1090, NIR-900-Et, and NIR-890-Peg4COOH. In the structures below, Ab=panitumumab. The absorbance spectra of the conjugates in pH 7.4 PBS are shown in FIG. 34 (NIR-900-Panitumumab), FIG. 35 (NIR-900-Et-Panitumumab), FIG. 36 (NIR-890-Peg4-COOH-Panitumumab), FIG. 37 (NIR-890-Panitumumab) and FIG. 38 (SWIR-1080-Panitumumab).

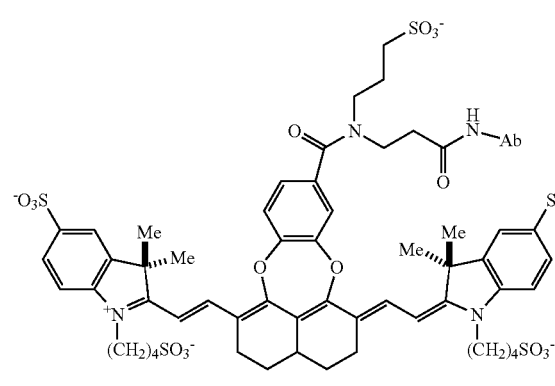

NIR-900-Panitumumab

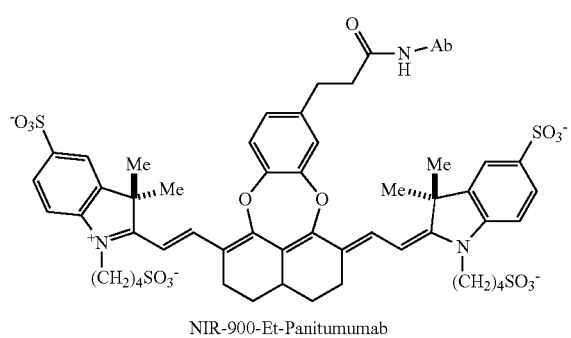

NIR-900-Et-Panitumumab

NIR-890-Peg₄-Panitumumab

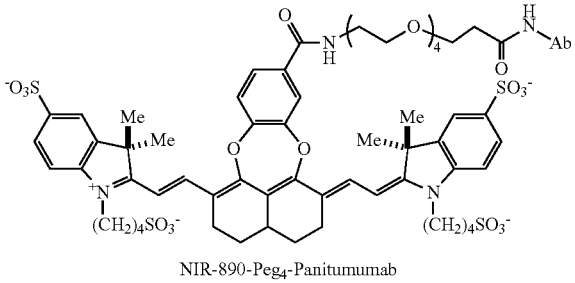

NIR-890-Panitumumab

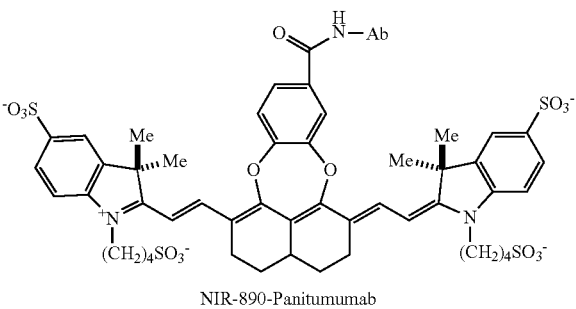

SWIR-1080-Panitumumab

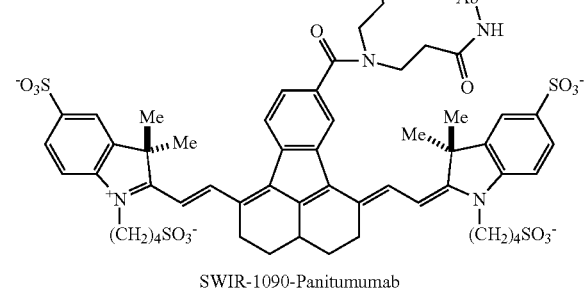

SWIR-1090-Panitumumab

Example 4

Dextran-Cyanine Fluorophore Conjugates

Several dextran-cyanine fluorophore conjugates were prepared and characterized. Dextran 10 kDa and Dextran 70 kDa were conjugated to activated esters of compounds NIR-890, NIR-900 and SWIR-1080.

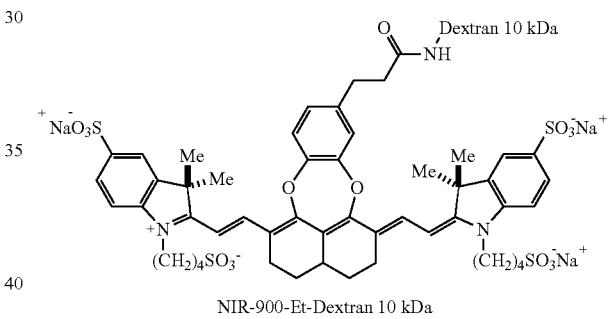

NIR-900-Et-Dextran 10 kDa

NIR-900-Dextran 10 kDa

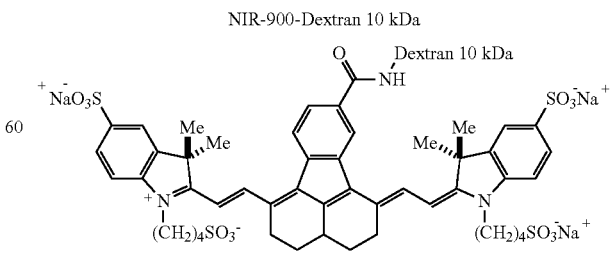

SWIR-1080-Dextran 10 kDa

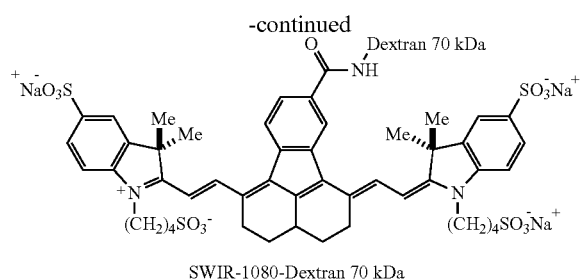

SWIR-1080-Dextran 70 kDa

Example 5 pH Sensitive Cyanine Fluorophore Synthesis and Characterization

An exemplary synthesis scheme for several fluorophores is shown in FIGS. 7-12.

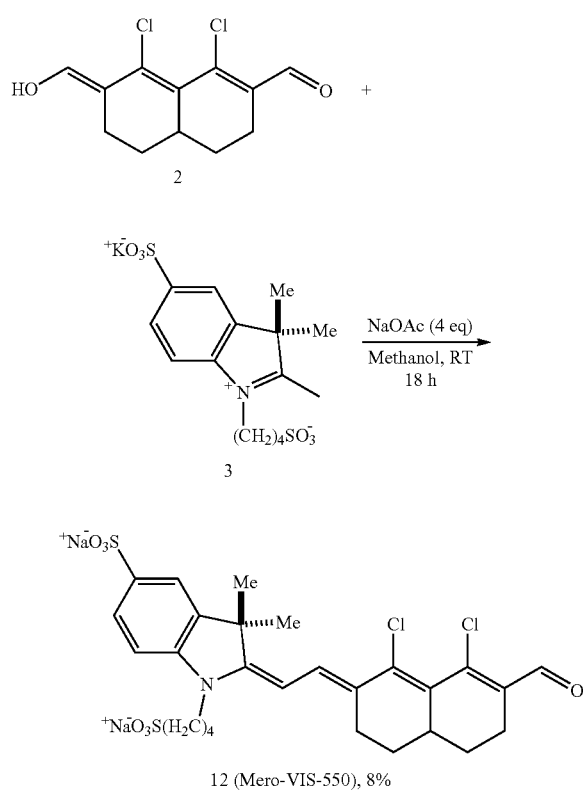

12 (Mero-VIS-550), 8%

Synthesis of 12: To a microwave reaction vial equipped with a magnetic stir bar was added bis sulfonated Indolenine 3 (1.12 g, 2.71 mmol, 1 eq), compound 2 (1.4 g, 5.4 mmol, 2 eq) and sodium acetate (445 mg, 5.4 mmol, 1 eq). After flushing with argon, methanol (8 mL) was added. The brown solution stirred at room temperature for overnight (~18 h). Evaporated the solvent, and the reaction mixture was diluted with saturated aqueous NaHCO$_3$ (20 mL). The resulting residue was purified by reversed-phase chromatography (150 g C$_{18}$ Aq, 0→30% acetonitrile/water), and the product-containing fractions were genevaced to afford 12 (156 mg, 8.7% yield) as a red solid. $^1$H NMR (400 MHz, methanol-d$_4$) δ 10.33 (s, 1H), 7.73-7.71 (m, 1H), 7.68-7.65 (m, 2H), 6.87-6.85 (d, 1H), 5.73-5.71 (d, 1H), 3.82-3.79 (t, 2H), 2.98-2.95 (m, 2H), 2.92-2.88 (t, 2H), 2.59 (m, 1H), 2.49-2.47 (m, 1H), 2.44-2.40 (m, 1H), 2.11-2.07 (m, 1H), 1.95-1.92 (m, 2H), 1.87-1.85 (m, 3H), 1.67-1.66 (d, 6H), 1.45-1.40 (m, 2H); LCMS calculated for C$_{27}$H$_{29}$Cl$_2$NO$_7$S$_2$$^{2-}$ 613.08, observed 616.1 [(M+2H)+1], and 306.6 [(M+2H)/2].

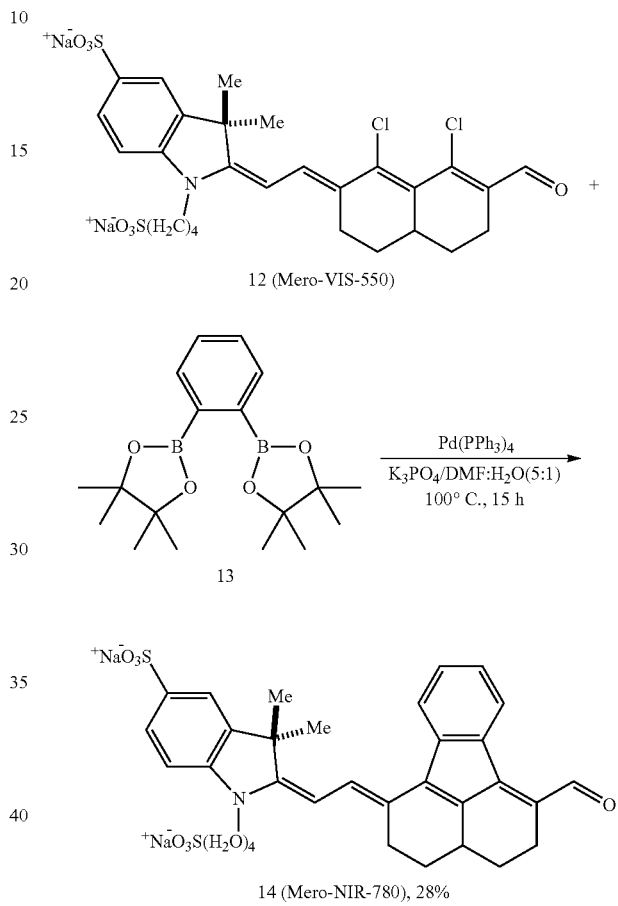

14 (Mero-NIR-780), 28%

Synthesis of 14: To a microwave vial equipped with a magnetic stir bar was added Compound 12 (40 mg, 0.65 mmol, 1 eq), 13 (60 mg, 0.18 mmol, 3 eq), Pd(PPh$_3$)$_4$ (7 mg, 0.006 mmol, 0.1 eq) and potassium phosphate tribasic (64.4 mg, 0.3 mmol, 5 eq). The vessel was sealed and flushed with argon. 0.3 ml of 5:1 ratio of DMF:H$_2$O was added, and the reaction was heated to 100° C. until product formation (~24 h). The reaction was cooled and diluted with 2 ml of saturated sodium bicarbonate and filtered through celite. The reaction solution was purified by reversed-phase chromatography (15.5 g C$_{18}$ Aq, 0→40% acetonitrile/water). The product-containing fractions were genevaced to afford 14 (11.4 mg, 28% yield) as a red solid. $^1$H NMR (400 MHz, methanol-d$_4$) δ 10.64 (s, 1H), 7.81-7.78 (d, 1H), 7.64-7.62 (d, 1H), 77.54 (m, 2H), 7.60-7.26 (t, 2H), 7.12-7.09. (t, 1H), 6.73-6.71 (d, 1H), 5.71-5.68 (d, 1H), 3.71-3.67 (t, 2H), 2.80-2.77 (t, 3H), 2.50-2.43 (m, 2H), 2.36-2.33 (t, 2H), 2.23-2.17 (m, 2H), 2.09-2.00 (m, 4H), 1.63-1.60 (d, 6H), 1.57-1.55 (d, 2H); LCMS calculated for C$_{33}$H$_{33}$NO$_7$S$_2$$^{2-}$ 619.17, observed 620.2 (M+1, and 309.7 (M/2.

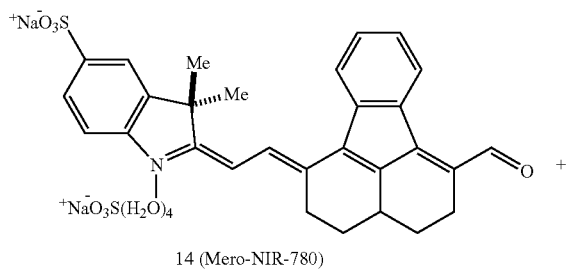

14 (Mero-NIR-780)

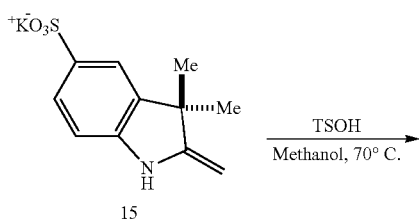

15 water and directly purified by reversed-phase chromatography (prep isco, 0→50% acetonitrile/2 mM ammonium bicarbonate in water). The product-containing fractions were genevaced to afford 16 (2.3 mg, 16% yield) as a green solid. $^1$H NMR (400 MHz, methanol-$d_4$) 8.76-8.72 (d, 1H), 8.14-8.12 (d, 1H), 7.93-7.89 (m, 2H), 7.80-7.78 (d, 1H), 7.71-7.68 (m, 2H), 7.64-7.58 (m, 2H), 7.37-7.30 (m, 2H), 6.98-6.94 (d, 1H), 6.82-6.80 (d, 1H), 5.83-5.80 (d, 1H), 3.80 (s, 2H), 3.15-3.09 (m, 2H), 2.95-2.91 (t, 2H), 2.69-2.64 (m, 2H), 2.50-2.45 (m, 1H), 2.22 (s, 2H), 1.99-1.86 (m, 4H), 1.78-1.75 (d, 6H), 1.56 (s, 6H), 1.46-1.41 (m, 2H); calculated for $C_{44}H_{43}N_2O_9S_3^{3-}$ 839.21, observed 841.2, 420.0 (M+½).

Figure 39:
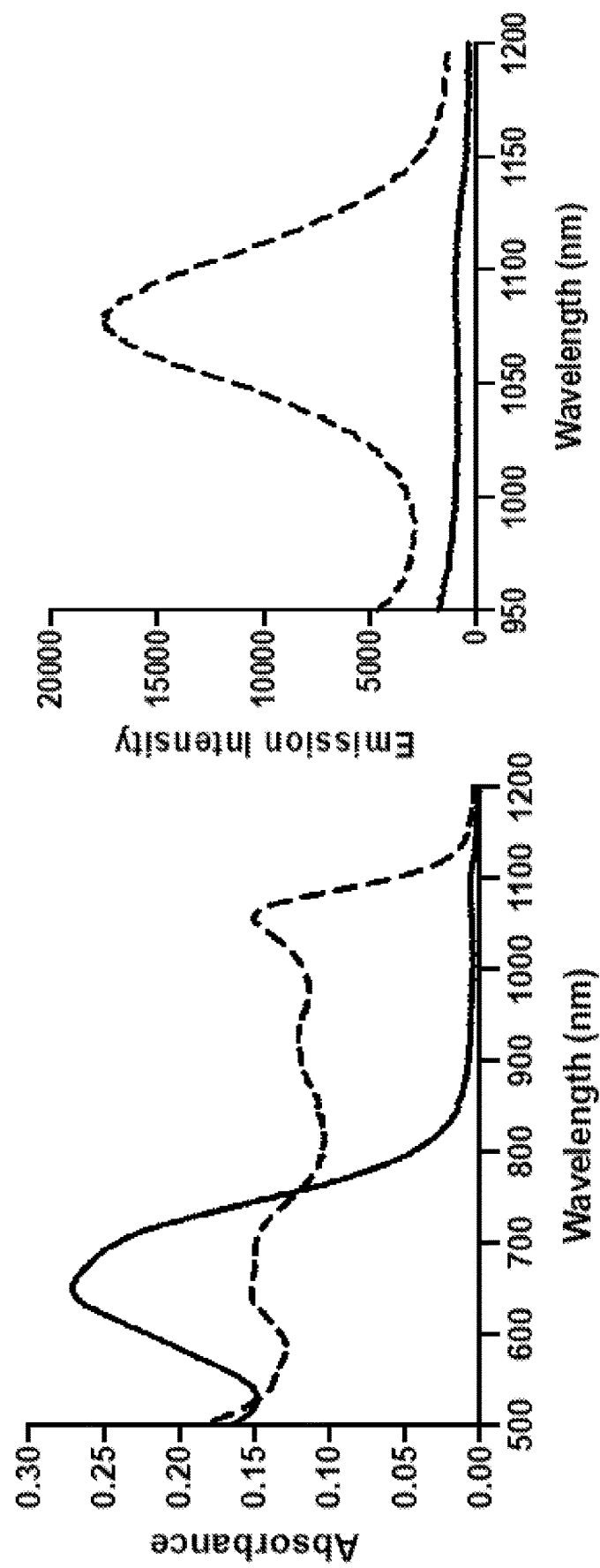
FIG. 39 is absorbance (left) and emission (right, excitation at 900 nm) spectra of 10 μM concentrated Compound 16 (pH-SWIR-1080) in pH 7.52 PBS 20% DMSO (solid) and pH 4.39 PBS 20% DMSO (dashed).

FIG. 39 shows absorbance (left) and emission (right, excitation at 900 nm) spectra of 10 mM concentrated Compound 16 (pH-SWIR-1080) in pH 7.52 PBS 20% DMSO (solid) and pH 4.39 PBS 20% DMSO (dashed). Compound 16 (pH-SWIR-1080) exhibited an absorbance maximum ($\lambda_{max, abs}$) of 650 nm with out an emission and a molar absorptivity ($\varepsilon$, M$^{-1}$cm$^{-1}$) of 29,000 in in pH 7.52 PBS 20% DMSO, $\lambda_{max, abs}$=1056 nm, $\lambda_{max, emiss}$=1080 nm, and $\varepsilon$=21,000 in pH 4.39 PBS 20% DMSO.

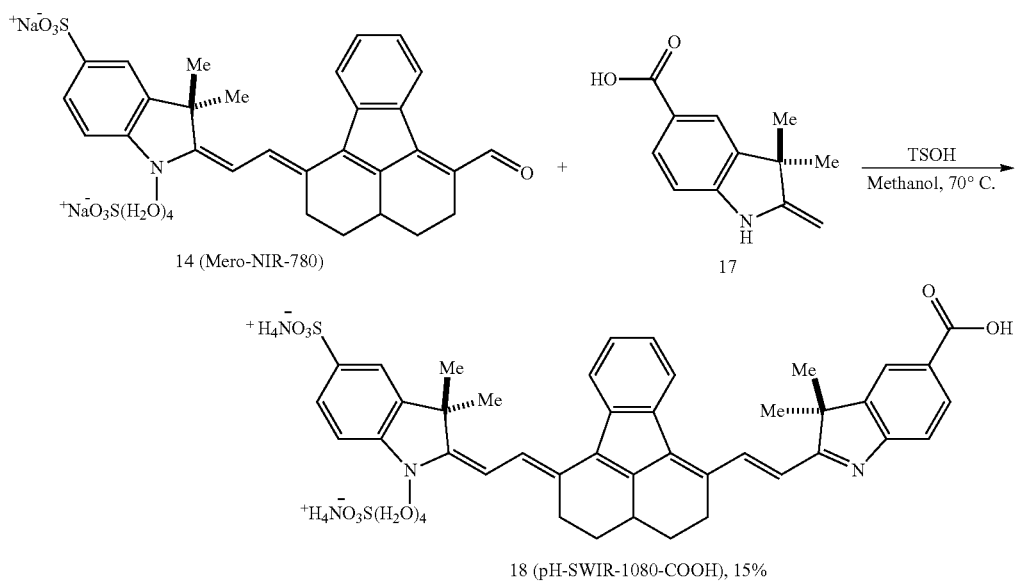

18 (pH-SWIR-1080-COOH), 15%

-continued

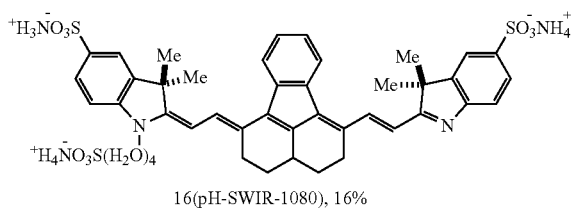

16(pH-SWIR-1080), 16%

Synthesis of 16: To a microwave reaction vial equipped with a magnetic stir bar was added compound 15 (10.94 mg, 0.016 mmol, 1 eq), compound 14 (13.68 mg, 0.04 mmol, 3 eq) and p-toluene sulfonic acid, mono hydrate (6.2 mg, 0.03 mmol, 2 eq). After flushing with argon, methanol (0.3 ml) was added. Reaction mixture was heated to 70° C. for 4.5 h. Solvent was evaporated, and the reaction was diluted with Synthesis of 18: To a microwave reaction vial equipped with a magnetic stir bar was added compound 14 (18 mg, 0.027 mmol, 1 eq), compound 17 (16.4 mg, 0.081 mmol, 3 eq) and p-Toluene sulfonic acid, mono hydrate (10.29 mg, 0.05 mmol, 2 eq). After flushing with argon, methanol (0.4 ml) was added. Reaction mixture was heated to 70° C. for 2 h. Solvent was evaporated, and the reaction was diluted with water and directly purified by reversed-phase chromatography (prep isco, 0→50% acetonitrile/2 mM ammonium bicarbonate in water). The product-containing fractions were genevaced to afford 18 (3.5 mg, 15% yield) as a green solid. $^1$H NMR (400 MHz, methanol-$d_4$) 8.61-8.56 (d, 1H), 8.01-7.98 (d, 1H), 7.94-7.91 (d, 2H), 7.66-7.65 (d, 1H), 7.58-7.54 (m, 2H), 7.47-7.43 (d, 2H), 7.25-7.22 (t, 1H), 7.18-7.14 (t, 1H), 6.85-6.80 (d, 1H), 6.68-6.66 (d, 1H), 5.69-5.66 (d, 1H), 3.66 (s, 2H), 3.02-2.93 (m, 3H), 2.81-2.78 (t, 2H), 2.10 (s, 3H), 1.85-1.83 (t, 3H), 1.77-1.75 (d, 2H), 1.63-1.61 (d, 6H), 1.42 (s, 6H), 1.33-1.31 (d, 2H); calculated for $C_{45}H_{44}N_2O_8S_2^{2-}$ 804.26, observed 807.3 [(M+2H)+1], 403.4 [(M+2H)/2].

Figure 40:
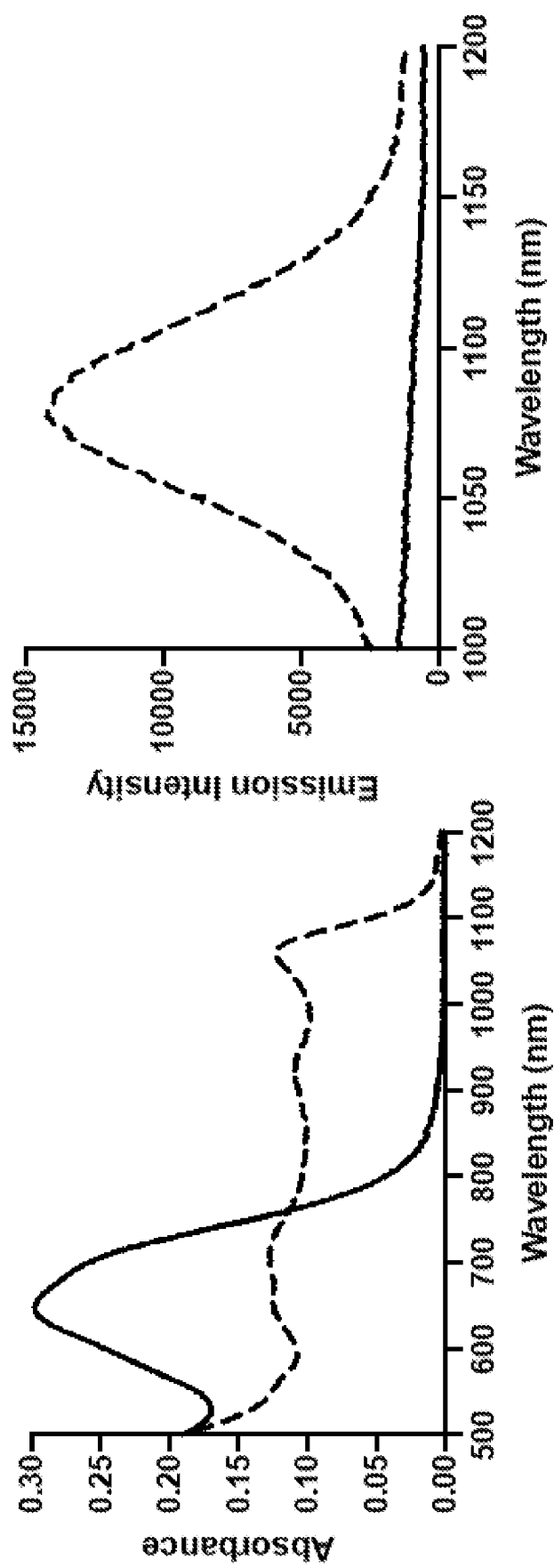
FIG. 40 is absorbance (left) and emission (right, excitation at 900 nm) spectra of 10 μM concentrated Compound 18 (pH-SWIR-1080-COOH) in pH 7.52 PBS 20% DMSO (solid) and pH 4.42 PBS 20% DMSO (dashed).

FIG. 40 shows absorbance (left) and emission (right, excitation at 900 nm) spectra of 10 mM concentrated Compound 18 (pH-SWIR-1080-COOH) in pH 7.52 PBS 20% DMSO (solid) and pH 4.42 PBS 20% DMSO (dashed). Compound 18 (pH-SWIR-1080-COOH) exhibited an absorbance maximum ($\lambda_{max,\ abs}$) of 650 nm with out an emission in pH 7.52 PBS 20% DMSO, $\lambda_{max,\ abs}$=1056 nm, $\lambda_{max,\ emiss}$=1080 nm in pH 4.39 PBS 20% DMSO.

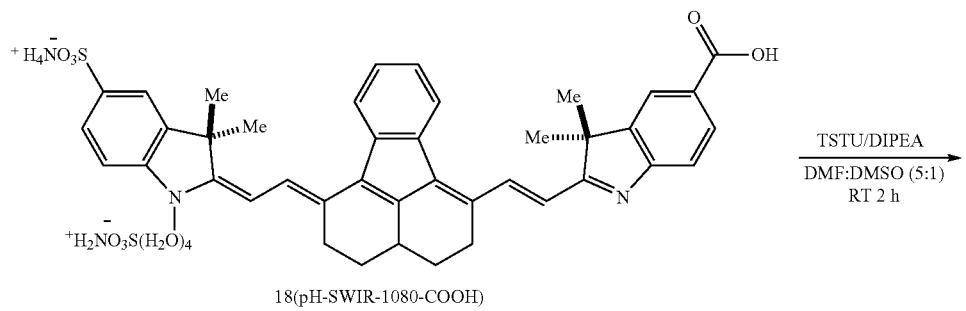

18(pH-SWIR-1080-COOH)

TSTU/DIPEA
DMF:DMSO (5:1)
RT 2 h

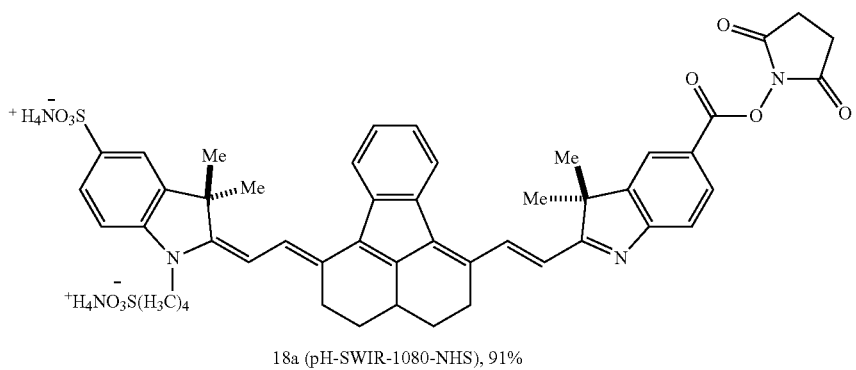

18a (pH-SWIR-1080-NHS), 91%

Synthesis of 18a: To a 1.5 ml Eppendorf® tube which has compound 18 (1.76 mg, 0.002 mmol, 1 eq) added TSTU (1.88 mg, 0.0062 mmol, 3 eq), DIPEA (1.8 µL, 0.014 mmol, 5 eq) and DMF:DMSO (200 µL, 5:1), were added and stirred at room temperature under argon. LCMS showed complete conversion to NHS product in 60 min. The reaction mixture was added to diethyl ether (10 mL) resulting in a green precipitate. After centrifugation the solid was placed under vacuum for 2 hours, yielding 18a (1.8 mg, 91% yield) as green solid. LCMS calculated for $C_{49}H_{47}N_3O_{10}S_2^{2-}$ (M+2H) 903.27, observed 904.3.

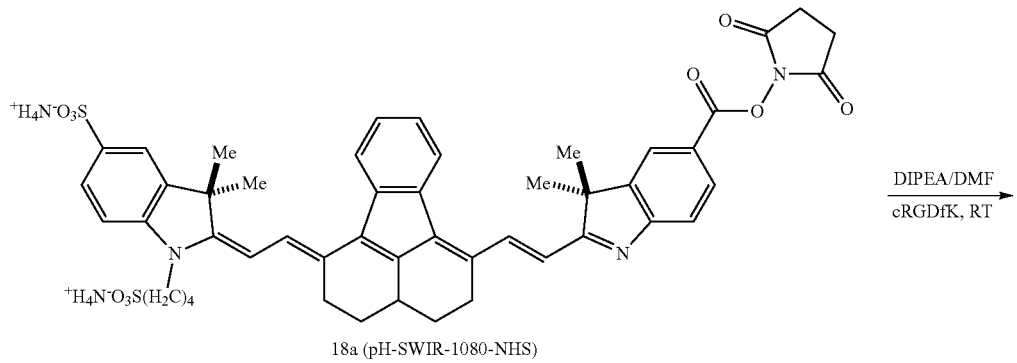

18a (pH-SWIR-1080-NHS)

DIPEA/DMF
cRGDfK, RT

-continued

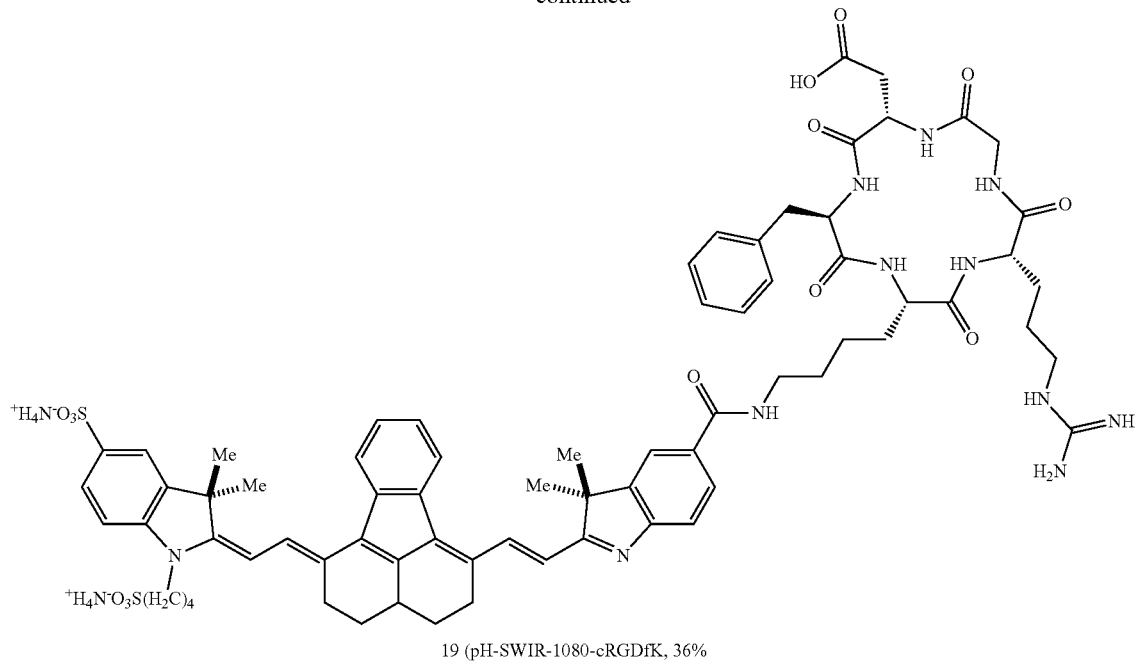

19 (pH-SWIR-1080-cRGDfK, 36%)

Synthesis of 19: To a 1.5 ml Eppendorf® tube was added cRGDfK (peptide international, PCI-3661-PI) (1.8 mg, 0.0024 mmol, 1.5 eq) added DIPEA (1.6 μL, 0.016 mmol, 5 eq) and DMF (200 μL) and vortexed for 30 seconds then added to the another 1.5 ml Eppendorf® tube which has compound 18a (1.8 mg, 0.0019 mmol, leg) stirred at room temperature under argon. LCMS showed major product conversion in 2 h. The reaction mixture was added to diethyl ether (10 mL) resulting in a green precipitate. After centrifugation the solid was diluted with water and purified by reversed-phase chromatography (prep isco, 0→50% acetonitrile/2 mM ammonium bicarbonate in water). The product-containing fractions were genevaced to afford 19 (0.98 mg, 36% yield) as a green solid. LCMS calculated for $C_{72}H_{83}N_{11}O_{14}S_2{}^{2-}$ (M+2H) 1391.56, observed 1392.6 and 696.9 (M+2H)/2.

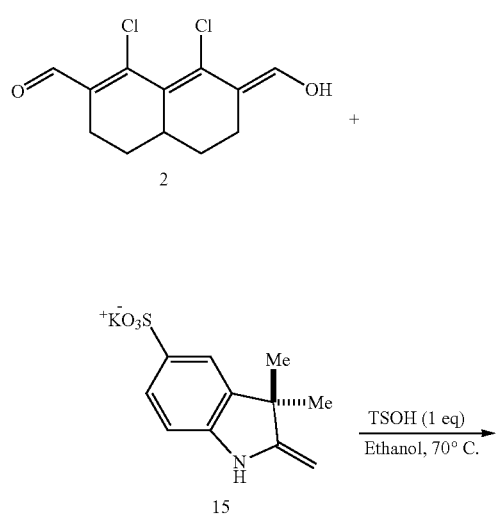

-continued

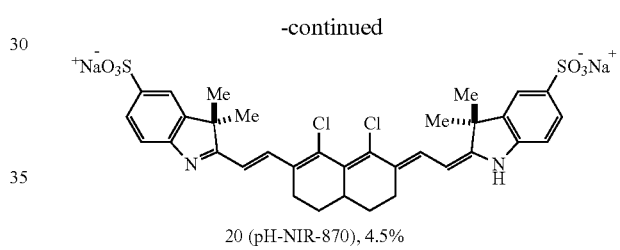

20 (pH-NIR-870), 4.5%

Synthesis of 20: To a microwave reaction vial equipped with a magnetic stir bar was added sulfonated Indolenine 15 (335.6 mg, 1.24 mmol, 3 eq), compound 2 (103 mg, 0.4 mmol, 1 eq) and p-Toluene sulfonic acid, mono hydrate (79 g, 0.4 mmol, 1 eq). After flushing with argon, ethanol (5 ml) was added. Reaction mixture was heated to 70° C. for 2 h. Solvent was evaporated, and the reaction mixture was diluted with saturated aqueous NaHCO$_3$ (2 mL). The resulting residue was purified by reversed-phase chromatography (30 g C$_{18}$ Aq, 0→30% acetonitrile/water), and the product-containing fractions were genevaced to afford 20 (13.2 mg, 4.5% yield) as a green solid. $^1$H NMR (400 MHz, methanol-d$_4$+drop of TFA) 8.24 (s, 1H), 8.14-8.13 (d, 1H), 8.06-8.03 (dd, 1H), 7.89 (d, 2H), 7.85-7.83 (dd, 2H), 7.74-7.67 (m, 1H), 7.25-7.23 (d, 2H), 2.91-2.86 (d, 2H), 2.50-2.43 (m, 2H), 2.21-2.17 (m, 2H), 1.74 (s, 2H), 1.63 (s, 1H), 1.59 (d, 12H); calculated for $C_{34}H_{33}Cl_2N_2O_6S^{2-}$ 699.2, observed 699.3, 349.2 (M/2).

Example 6

Hydrophobic Cyanine Fluorophore Synthesis and Characterization

An exemplary synthesis scheme for several fluorophores is shown in FIGS. 13-16.

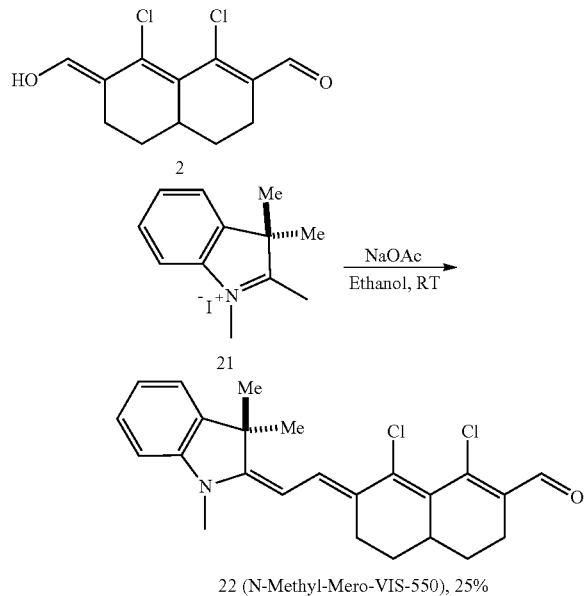

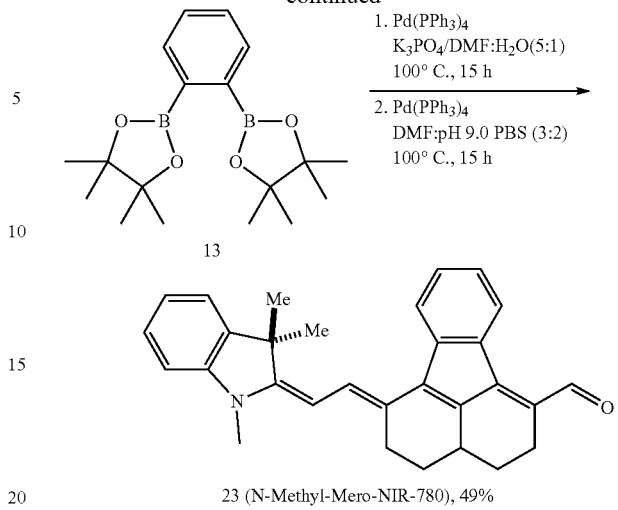

23 (N-Methyl-Mero-NIR-780), 49%

Synthesis of 22: To a microwave reaction vial equipped with a magnetic stir bar was added compound 2 (952 mg, 3.16 mmol, 1 eq), compound 21 (1.3 g, 5.05 mmol, 1.6 eq) and sodium acetate (259 mg, 3.16 mmol, 1 eq). After flushing with argon, ethanol (7 ml) was added. The reaction mixture was stirred at room temperature for 2.5 h. Evaporated the solvent, and the reaction mixture was diluted with dichloromethane. Washed the reaction mixture with water and dried through sodium sulphate and filtered. Evaporated the solvent and purified by normal-phase chromatography (40 g silica column, 0-100% hexane/dichloromethane). The product-containing fractions were evaporated to afford 22 (325 mg, 25% yield) as a red colored solid. $^1$H NMR (400 MHz, Chloroform-d) δ 10.36 (s, 1H), 7.65-7.62 (d, 1H), 7.21-7.17 (m, 2H), 6.92-6.88 (t, 1H), 6.68-6.66 (d, 1H), 5.46-5.43 (d, 1H), 3.20 (s, 3H), 2.58-2.53 (m, 2H), 2.51-2.49 (d, 1H), 2.43-2.38 (m, 3H), 2.22-2.17 (m, 1H), 1.65-1.63 (d, 6H), 1.38-1.36 (m, 2H); $^{13}$C NMR (500 MHz, chloroform-d) δ 192.27, 161.01, 144.73, 144.64, 139.15, 137.30, 134.97, 128.61, 128.41, 127.80, 126.16, 121.72, 120.34, 106.35, 92.95, 46.15, 40.16, 29.73, 29.60, 29.28, 28.46, 28.06, 24.89, 24.58; LCMS calculated for $C_{24}H_{25}Cl_2NO$ 413.13, observed 414.2.

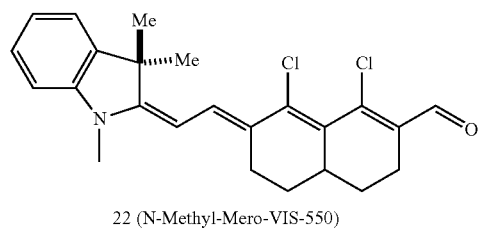

22 (N-Methyl-Mero-VIS-550)

Synthesis of 23: To a microwave vial equipped with a magnetic stir bar was added Compound 22 (95 mg, 0.22 mmol, 1 eq), 13 (227.17 mg, 0.68 mmol, 3 eq), Pd(PPh$_3$)$_4$ (26.52 mg, 0.02 mmol, 0.1 eq) and potassium phosphate tribasic (97.41 mg, 0.45 mmol, 2 eq). The vessel was sealed and flushed with argon. 1 ml of 5:1 ratio of DMF:H$_2$O was added, and the reaction was heated to 100° C. for overnight (~18 h). LCMS showed major 582 m/z. which is the mono chloro substituted product. The reaction was cooled and diluted with dichloromethane and filtered through celite. Dichloromethane layer was washed with water and dried through sodium sulphate and filtered. Evaporated the solvent and transferred the crude mono choro substituted product to the microwave reaction vial. To the vial added Pd(PPh$_3$)$_4$ (26.52 mg) and potassium phosphate tribasic (97.41 mg). The vessel was sealed and flushed with argon. 1 ml of 3:2 ratio of DMF: 250 mM pH 9.0 PBS was added, and the reaction was heated to 100° C. for overnight (~18 h). LCMS showed major product which is 420 m/z. The reaction was cooled and diluted with dichloromethane and filtered through celite. Dichloromethane layer was washed with water and dried through sodium sulphate and filtered. Purified by normal-phase chromatography (12 g silica gold column, 0→100% hexane/dichloromethane). The product-containing fractions were evaporated to afford 23 (47.59 mg, 49% yield) as a blue solid. $^1$H NMR (400 MHz, Chloroform-d) δ 10.81 (s, 1H), 7.84-7.82 (d, 1H), 7.74-7.73 (d, 1H), 7.67-7.63 (m, 2H), 7.38-7.34 (m, 2H), 7.20-7.17 (m, 2H), 6.91-6.87 (t, 1H), 6.66-6.66 (d, 1H), 3.22 (s, 3H), 2.60-2.53 (m, 2H), 2.46-2.41 (m, 1H), 2.34-2.33 (m, 1H), 2.13-2.12 (m, 3H), 1.73-1.71 (d, 6H), 1.30-1.27 (m, 2H); $^{13}$C NMR (500 MHz, chloroform-d) δ 188.98, 158.95, 148.67, 144.94, 142.91, 140.66, 140.21, 138.98, 137.92, 136.08, 135.09, 128.66, 127.85, 125.73, 125.71, 125.37, 124.39, 121.65, 121.19, 120.02, 106.21, 93.63, 45.77, 33.92, 30.34, 29.98, 29.28, 28.21, 28.18, 26.32, 23.54; LCMS calculated for $C_{30}H_{29}NO$ 419.22, observed 420.3.

Figure 41:
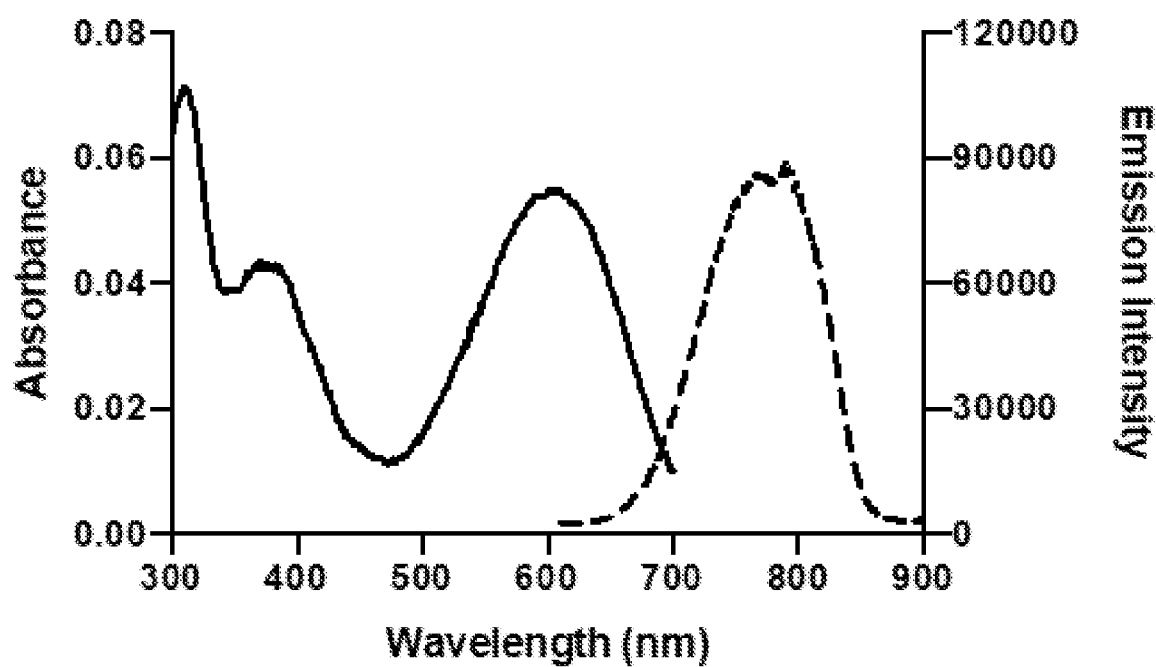
FIG. 41 is absorbance (solid) and emission (dashed, excitation at 600 nm) spectra of 5 μM concentrated Compound 23 (N-Methyl-Mero-NIR-780) in acetonitrile.

FIG. 41 shows absorbance (solid) and emission (dashed, excitation at 600 nm) spectra of 5 μM concentrated Compound N-Methyl-Mero-NIR-780 in Acetonitrile. Compound 23 (N-Methyl-Mero-NIR-780) exhibited absorbance maximum ($\lambda_{max,\ abs}$) of 600 nm, an emission maximum ($\lambda_{max,\ emiss}$) of 780 nm in Acetonitrile.

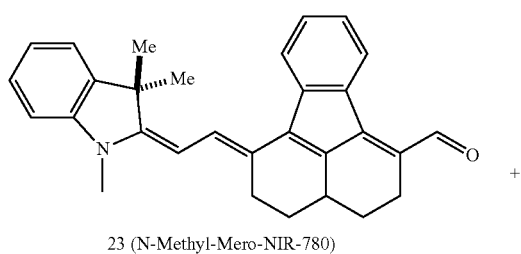

23 (N-Methyl-Mero-NIR-780)

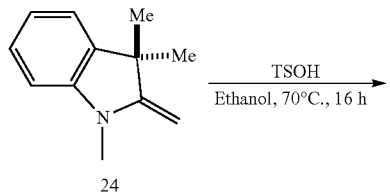

24

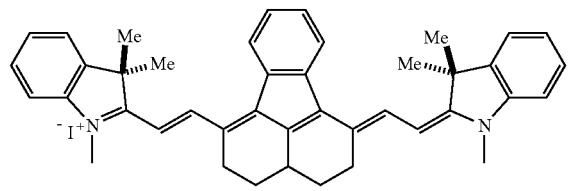

25 (N-Methyl-SWIR-1080), 33%

Synthesis of 25: To a microwave reaction vial equipped with a magnetic stir bar was added compound 23 (23 mg, 0.054 mmol, 1 eq), compound 24 (29.3 µL, 0.16 mmol, 3 eq) and p-Toluene sulfonic acid, mono hydrate (20.8 mg, 0.1 mmol, 2 eq). After flushing with argon, ethanol (0.6 ml) was added. Reaction mixture was heated to 70° C. for overnight (~18 h). Solvent was evaporated, and the reaction was diluted with dichloromethane and washed with water. Dried the dichloromethane layer through sodium sulphate and filtered through cotton. Purified by normal-phase chromatography (12 g silica gold column, 0→20% dichloromethane/methanol). The product-containing fractions were evaporated to afford 25 (13 mg, 33% yield) as a solid. $^1$H NMR (500 MHz, methanol-$d_4$) 8.46-8.44 (d, 2H), 7.85-7.82 (d, 2H), 7.56-7.54 (d, 2H), 7.47-7.43 (t, 2H), 7.41-7.39 (m, 2H), 7.34-7.28 (m, 4H), 6.47-6.44 (d, 2H), 3.71 (s, 6H), 3.21-3.17 (d, 2H), 2.63-2.60 (m, 3H), 2.30-2.27 (m, 2H), 1.84-1.80 (m, 12H), 1.47-1.43 (m, 2H); $^{13}$C NMR (500 MHz, methanol-$d_4$) δ 170.83, 146.90, 143.22, 141.09, 139.33, 138.33, 137.68, 130.57, 128.47, 127.19, 124.79, 122.59, 121.95, 110.40, 102.33, 33.34, 30.40, 29.65, 28.96, 26.62, 26.58, 25.81; LCMS calculated for $C_{42}H_{43}N_2$ 575.34, observed 575.4.

Figure 43:
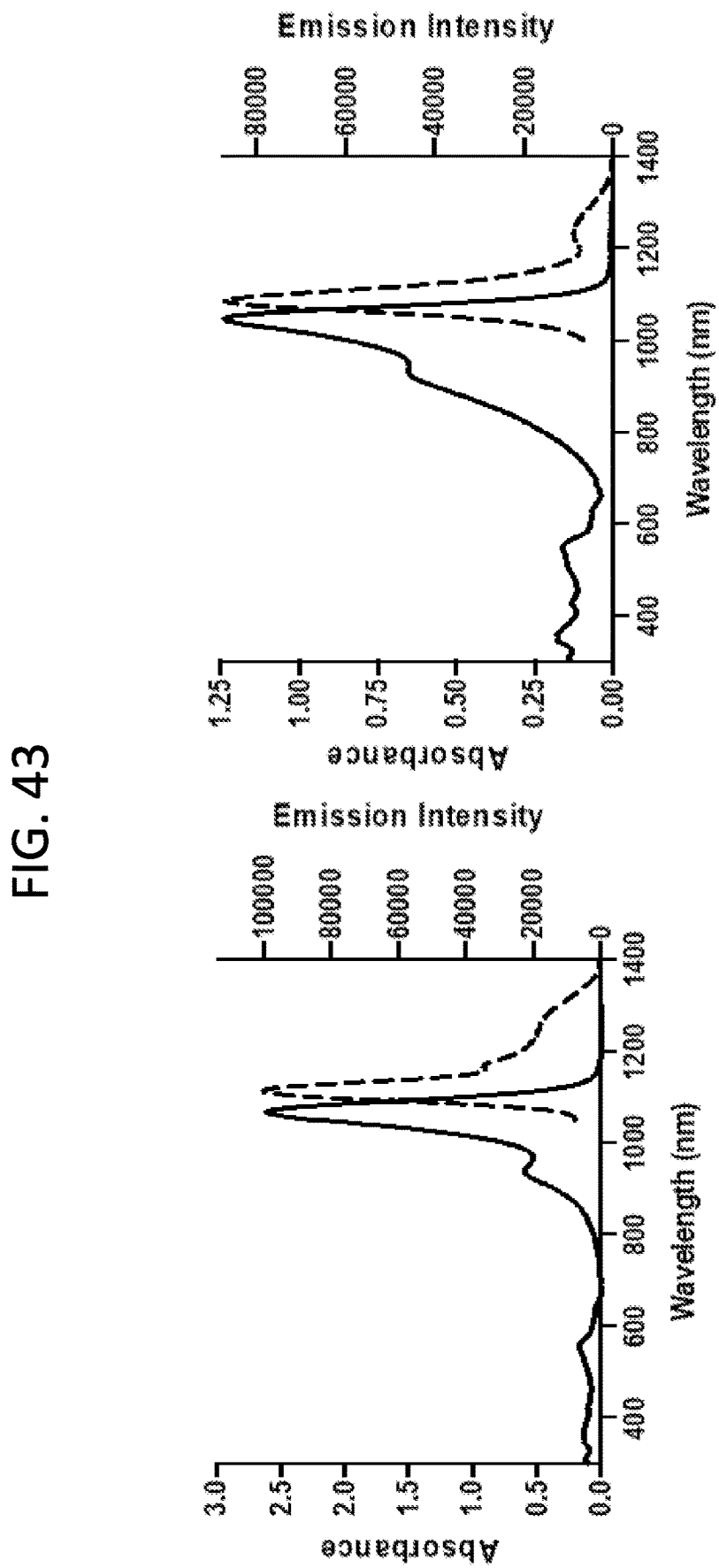
FIG. 43 is absorbance (solid) and emission (dashed, excitation at 900 nm) spectra of 5 μM concentrated Compound 25 (N-Methyl-SWIR-1080) in dichloromethane (left) and in methanol (right).

FIG. 43 shows absorbance (solid) and emission (dashed, excitation at 900 nm) spectra of 5 µM concentrated Compound N-Methyl-SWIR-1080 in dichloromethane (right) and in methanol (left). Compound 25 (N-Methyl-SWIR-1080) exhibited absorbance maximum ($\lambda_{max, abs}$) of 1066 nm, an emission maximum ($\lambda_{max, emiss}$) of 1110 nm in methanol.

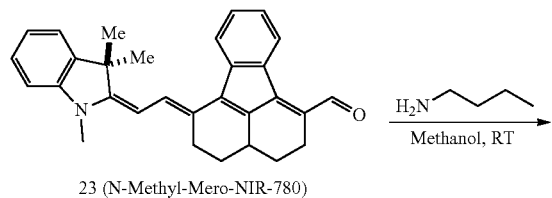

23 (N-Methyl-Mero-NIR-780)

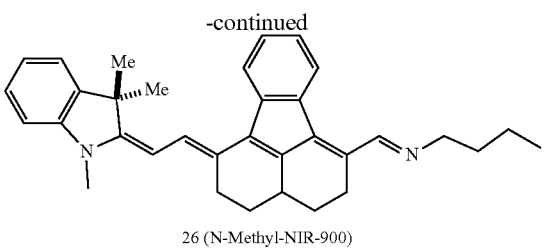

26 (N-Methyl-NIR-900)

Synthesis of 26: To a 1.5 ml Eppendorf® tube which has a compound 23 (0.4 mg, 0.95 µmol, 1 eq) was added butyl amine (1.4 µL, 14 µmol, 15 eq) and methanol (150 µL) was added. Reaction mixture was heated stirred under argon for 2 h. LCMS showed major 475 m/z which is the desired product. Evaporated the methanol and dried under vacuum for overnight. Prepared the DMSO stock solution of obtained pink colored solid compound 26 and measure the optical properties. In acetonitrile $\lambda_{abs}$=540 nm and $\lambda_{emiss}$=720 nm and in 0.1% formic acid in acetonitrile $\lambda_{abs}$=872 nm and $\lambda_{emiss}$=906 nm. LCMS calculated for $C_{34}H_{38}N_2$ 474.30, observed 475.

Figure 42:
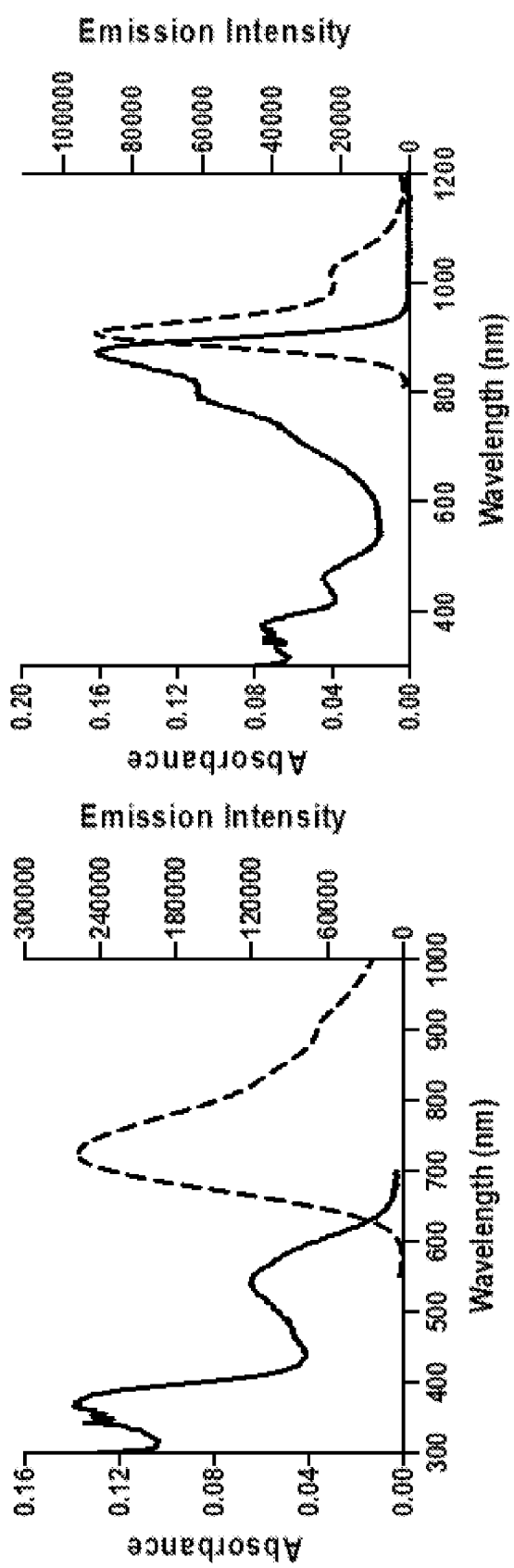
FIG. 42 is absorbance (left) absorbance (solid) and emission (dashed, excitation at 540 nm) spectra of 15 μM concentrated Compound 26 (N-Methyl-NIR-900) in acetonitrile (right). Absorbance (solid) and emission (dashed, excitation at 800 nm) spectra of 15 μM concentrated Compound N-Methyl-NIR-900 in 0.1% formic acid in acetonitrile.

FIG. 42 shows absorbance (left) absorbance (solid) and emission (dashed, excitation at 540 nm) spectra of 15 µM concentrated Compound N-Methyl-NIR-900 in acetonitrile. Absorbance (solid) and emission (dashed, excitation at 800 nm) spectra of 15 µM concentrated Compound N-Methyl-NIR-900 in 0.1% formic acid in acetonitrile (right). Compound 26 (N-Methyl-NIR-900) exhibited absorbance maximum ($\lambda_{max, abs}$) of 540 nm, an emission maximum ($\lambda_{max, emiss}$) of 720 nm in acetonitrile and absorbance maximum ($\lambda_{max, abs}$) of 872 nm, an emission maximum ($\lambda_{max, emiss}$) of 906 nm in 0.1% formic acid in acetonitrile.

Example 7

Benzoindole Cyanine Fluorophore Synthesis and Characterization

Figure 17:
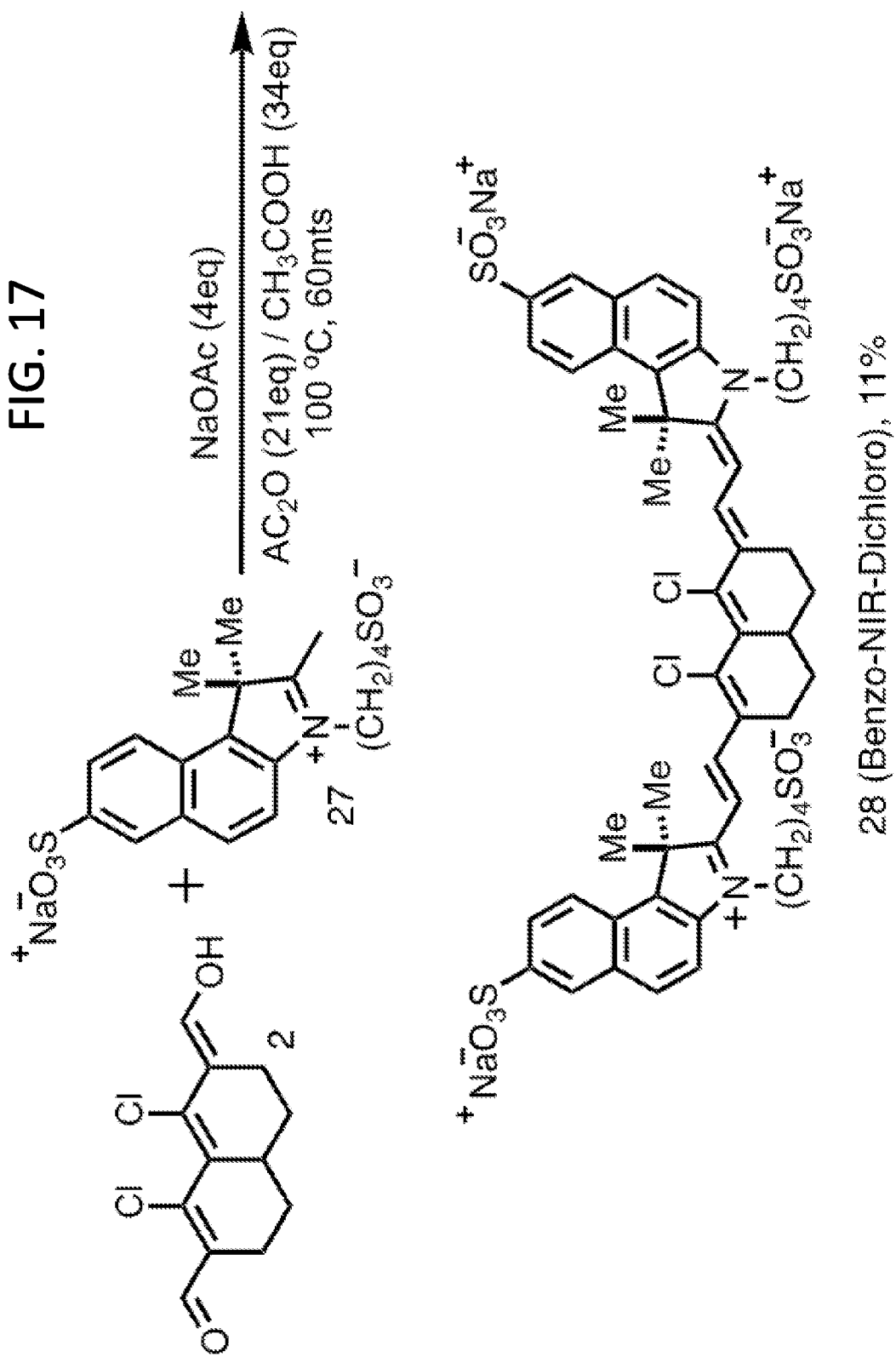
Figure 18:
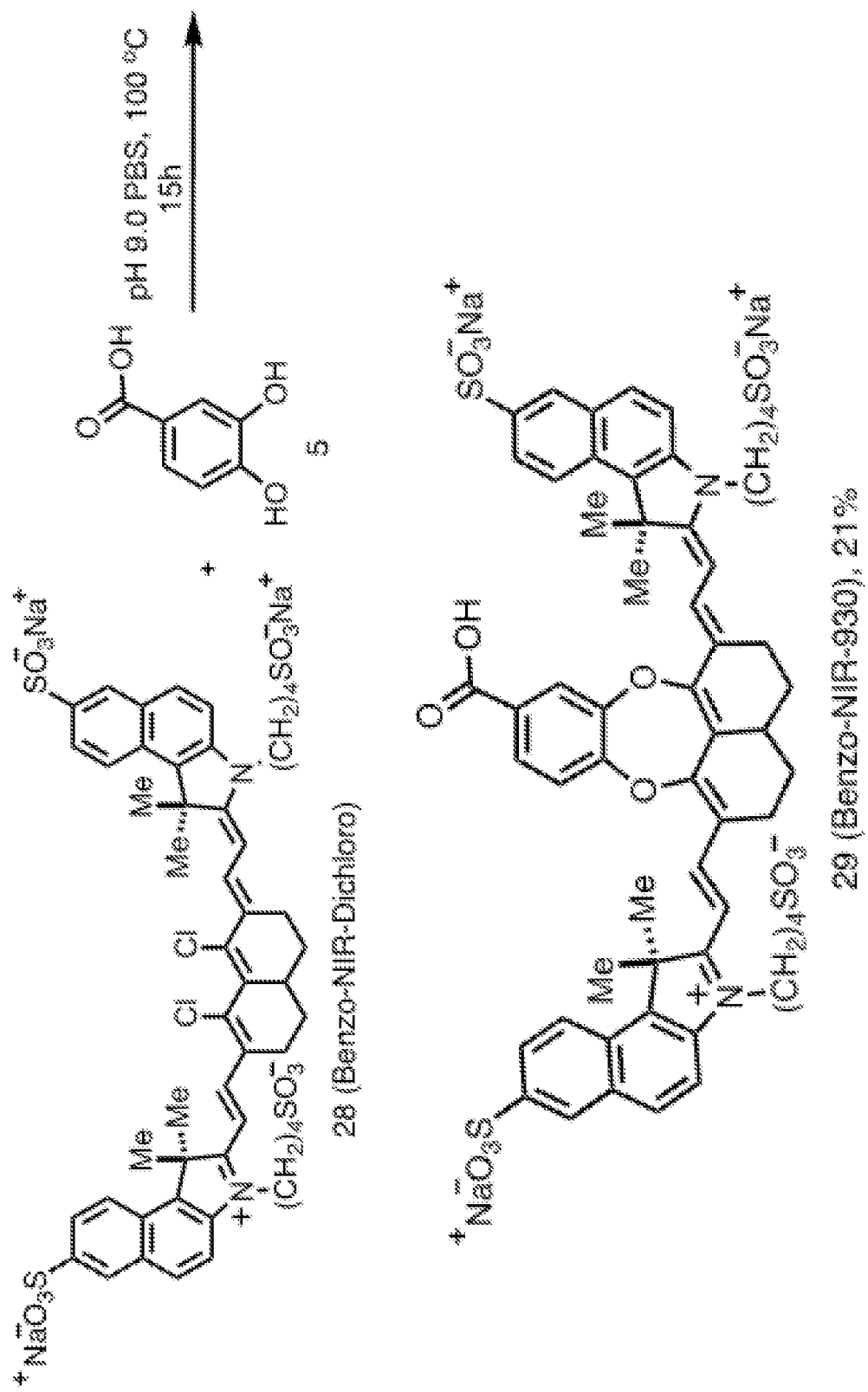

An exemplary synthesis scheme for several fluorophores is shown in FIGS. 17-18.

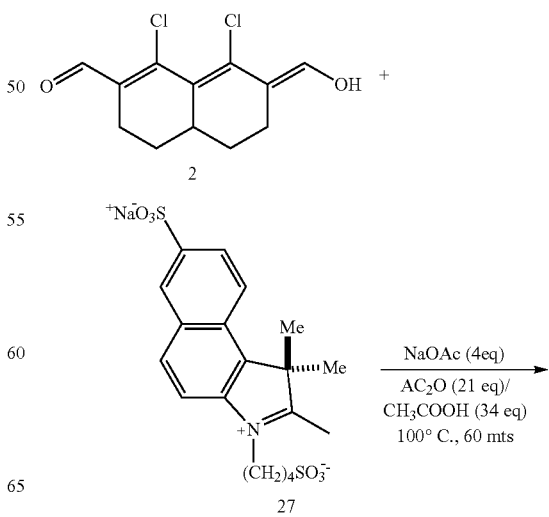

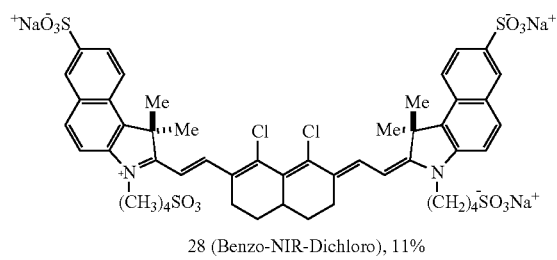

28 (Benzo-NIR-Dichloro), 11%

Synthesis of 28: To a microwave reaction vial equipped with a magnetic stir bar was added bis sulfonated benzo Indolenine 27 (333 mg, 0.74 mmol, 3 eq), compound 2 (64 mg, 0.24 mmol, 1 eq) and sodium acetate (81.7 mg, 0.99 mmol, 4 eq). After flushing with argon, acetic acid (0.48 mL, 8.43 mmol, 34 eq) and acetic anhydride (0.49 mL, 5.20 mmol, 21 eq) were added in succession. The brown solution was heated to 100° C. for 60 minutes. The reaction mixture was cooled and diluted with saturated aqueous NaHCO$_3$ (2 mL). The resulting residue was purified by reversed-phase chromatography (30 g C$_{18}$ Aq, 0→30% acetonitrile/water), and the product-containing fractions were genevaced to afford 28 (32 mg, 11% yield) as a green solid. $^1$H NMR (400 MHz, methanol-d$_4$) δ 8.39-8.33 (m, 4H), 8.24-8.22 (d, 2H), 8.02-8.00 (d, 2H), 7.93-7.90 (d, 2H), 7.63-7.61 (d, 2H), 6.34-6.31 (d, 2H), 4.25-4.21 (m, 4H), 2.83-2.79 (t, 4H), 2.61-2.56 (m, 1H), 2.47-2.40 (m, 2H), 2.15-2.12 (m, 2H), 1.97-1.87 (br, 22H), 1.40-1.36 (m, 2H); LCMS calculated for C$_{50}$H$_{51}$Cl$_2$N$_2$O$_{12}$S$_4{}^{3-}$ (M+3H) 1074.17, observed 1075 (M+1), 357 (M/2).

Synthesis of 29: To a microwave vial equipped with a magnetic stir bar was added compound 28 (19 mg, 0.16 mmol, 1 eq) and 3,4-Dihydroxy benzoic acid 5 (12.8 mg, 0.08 mmol, 5 eq). The vessel was sealed and flushed with argon, after which 1 mL of 250 mM pH 9.0 PBS was added and the reaction was heated to 100° C. for 15 hr. The reaction was cooled and diluted with saturated aqueous NaHCO$_3$ (1 mL), and the solution was directly purified by reversed-phase chromatography (15.5 g C$_{18}$ Aq, 0→40% acetonitrile/water). The product-containing fractions were genevaced to afford 29 (4 mg, 21% yield) as a blue solid. $^1$H NMR (400 MHz, methanol-d$_4$) δ 8.87-8.74 (m, 2H), 8.47-8.45 (d, 2H), 8.42-8.38 (t, 2H), 8.14-8.11 (t, 2H), 8.07-8.00 (m, 3H), 7.97-7.95. (d, 1H), 7.75-7.70 (t, 2H), 7.38-7.35. (d, 1H), 6.37-6.28 (d, 2H), 4.36-4.29 (m, 4H), 2.98-2.94 (m, 5H), 2.68-2.67 (m, 1H), 2.59-2.55 (m, 2H), 2.23-2.15 (t, 15H), 2.11-2.04 (br, 8H), 1.52-1.48 (m, 2H); LCMS calculated for C$_{57}$H$_{55}$N$_2$O$_{16}$S$_4{}^{3-}$ (M+3H) 1154.25, observed 1155.3 (M+1), 384.1 (M/2).

Figure 44:
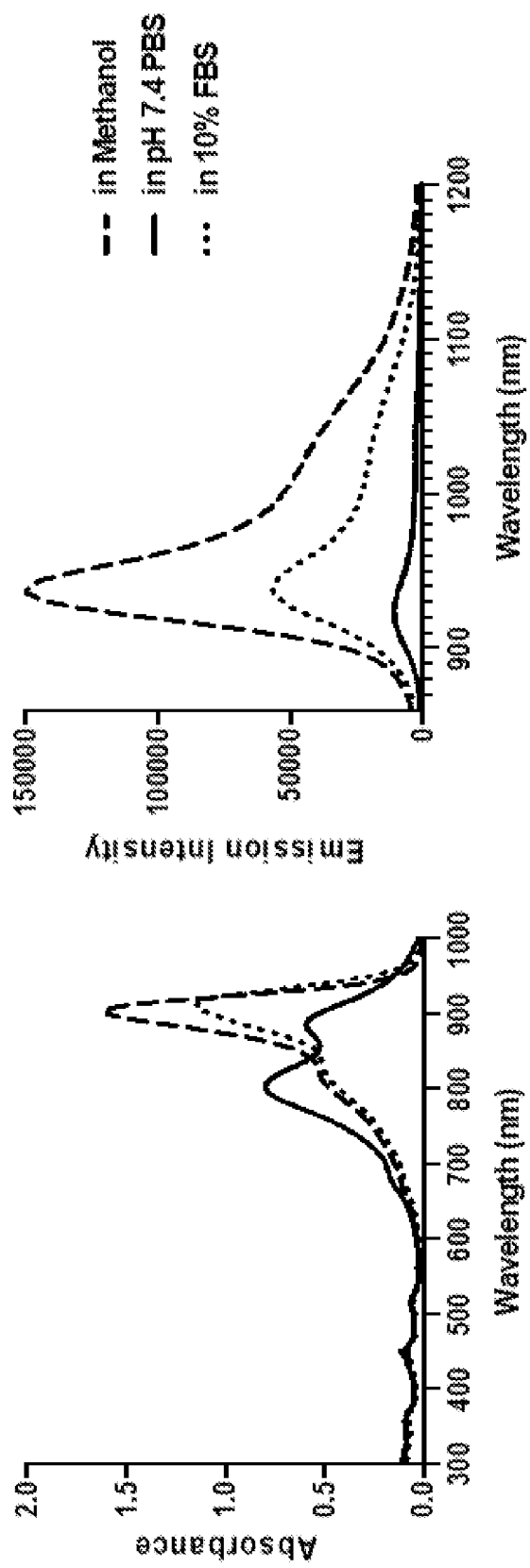
FIG. 44 is absorbance (left) and emission (right, excitation at 850 nm) spectra of 5 μM concentrated Compound 29 (Benzo-NIR-930) in different solvents as indicated.

FIG. 44 is absorbance (left) and emission (right, excitation at 850 nm) spectra of 5 μM concentrated Compound 10 (Benzo-NIR-930) in different solvents as indicated. Compound 29 (Benzo-NIR-930) exhibited absorbance maximum ($λ_{max, abs}$) of 884 nm, an emission maximum ($λ_{max, emiss}$) of 919 nm in pH 7.4 PBS, $λ_{max, abs}$=911 nm, $λ_{max, emiss}$=937 nm in 10% (v/v) FBS in pH 7.4 PBS, and $λ_{max, abs}$=900 nm, $λ_{max, emiss}$=936 nm in methanol.

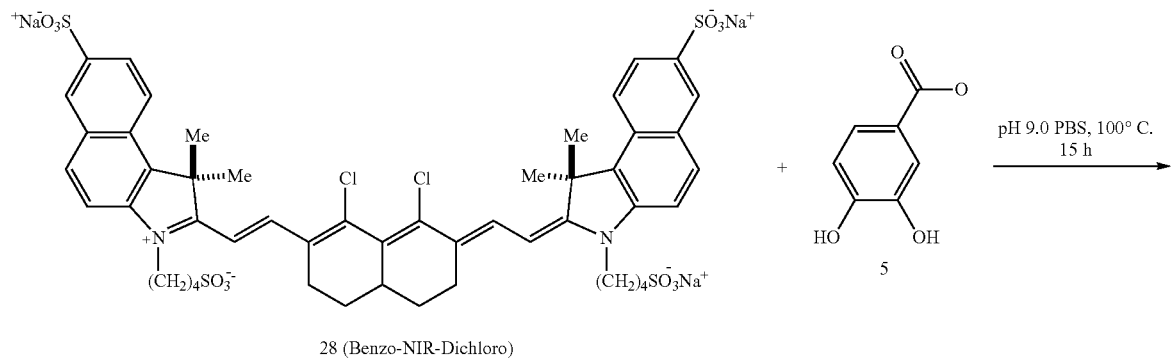

28 (Benzo-NIR-Dichloro)

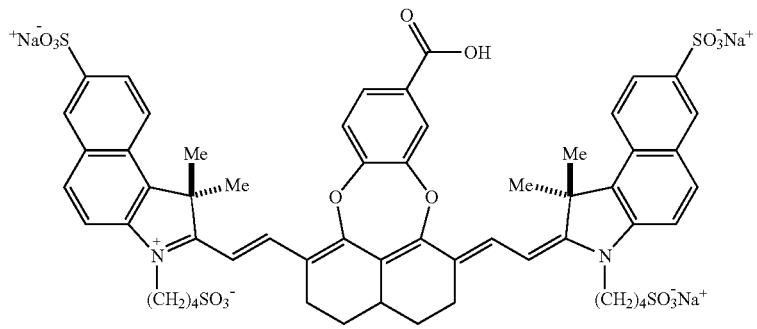

29 (Benzo-NIR-930), 21%

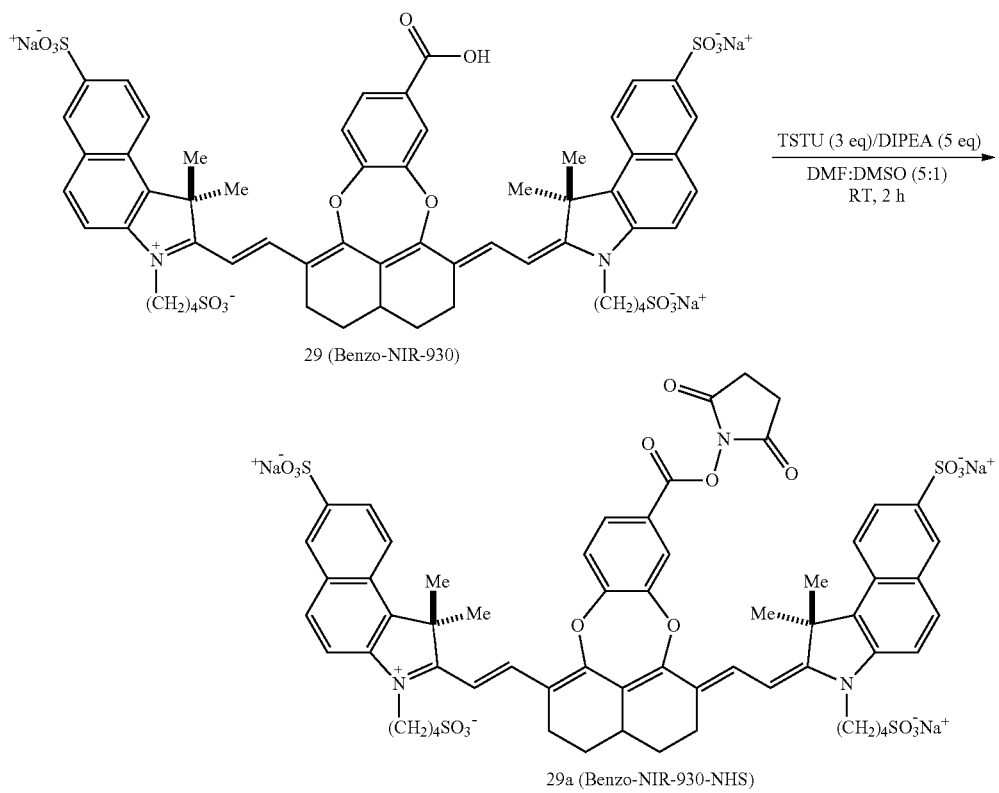

Synthesis of 29a: To a 1.5 ml Eppendorf® tube which has compound 29 (2.3 mg, 0.002 mmol, 1 eq) added TSTU (1.8 mg, 0.006 mmol, 3 eq), DPEA (1.76 µL, 0.01 mmol, 5 eq) and DMF:DMSO (200 µL, 5:1), were added and stirred at room temperature under argon. LCMS showed complete conversion to NHS product in 2 h. The reaction was added to diethyl ether (10 mL) resulting in a green precipitate. After centrifugation the solid was placed under vacuum for 2 hours, yielding 29a (2.35 mg, 90% yield) as green colored solid. LCMS calculated for $C_{61}H_{58}N_3O_{18}S_4^{3-}$ 1248.26, observed 1252 [(M+3H)+1], 416 (M/2).

Example 8

Tumor Visualization with Cyanine Fluorophores

A subject having a tumor is identified and selected for treatment. The subject may be selected based on a clinical presentation and/or by performing tests to demonstrate presence of a tumor.

The subject is treated by administering a compound according to any one of Formulas I-V, a pharmaceutically acceptable salt thereof, or a pharmaceutical composition thereof at a dose determined by a clinician to be effective. The compound is administered by any suitable means, such as intravenous or subcutaneous injection. In some instances, the compound is injected directly into the tumor. In some embodiments, the compound according to any one of Formulas I-V includes at least one targeting agent capable of binding to a target within the tumor, e.g., an antibody capable of binding to an antigen on a tumor cell.

Visualization may be performed after a period of time sufficient to allow binding of the compound to the tumor. For example, irradiation may be performed several hours to several days after administration of the compound, such as from 1-7 days after administration of the compound. The administered compound is irradiated by targeted application of an effective quantity of light having a wavelength and a selected intensity suitable for inducing fluorescence of the cyanine fluorophore to a targeted portion of the subject, thereby exciting the cyanine fluorophore. Advantageously, the portion of the subject targeted for irradiation is proximate the tumor. Fluorescence of the compound is detected by any suitable method known to a person of ordinary skill in the art of fluorescence imaging. Fluorescence-guided surgery is used to determine the location and extent of tissue excision.

In some cases, the subject is suspected of having a tumor and presence of a tumor is confirmed by administering the compound to the subject and monitoring the compound's fluorescence at a suspected tumor site. Accumulation of the compound and fluorescence at the suspected tumor site diagnoses presence of a tumor.

Figure 45:
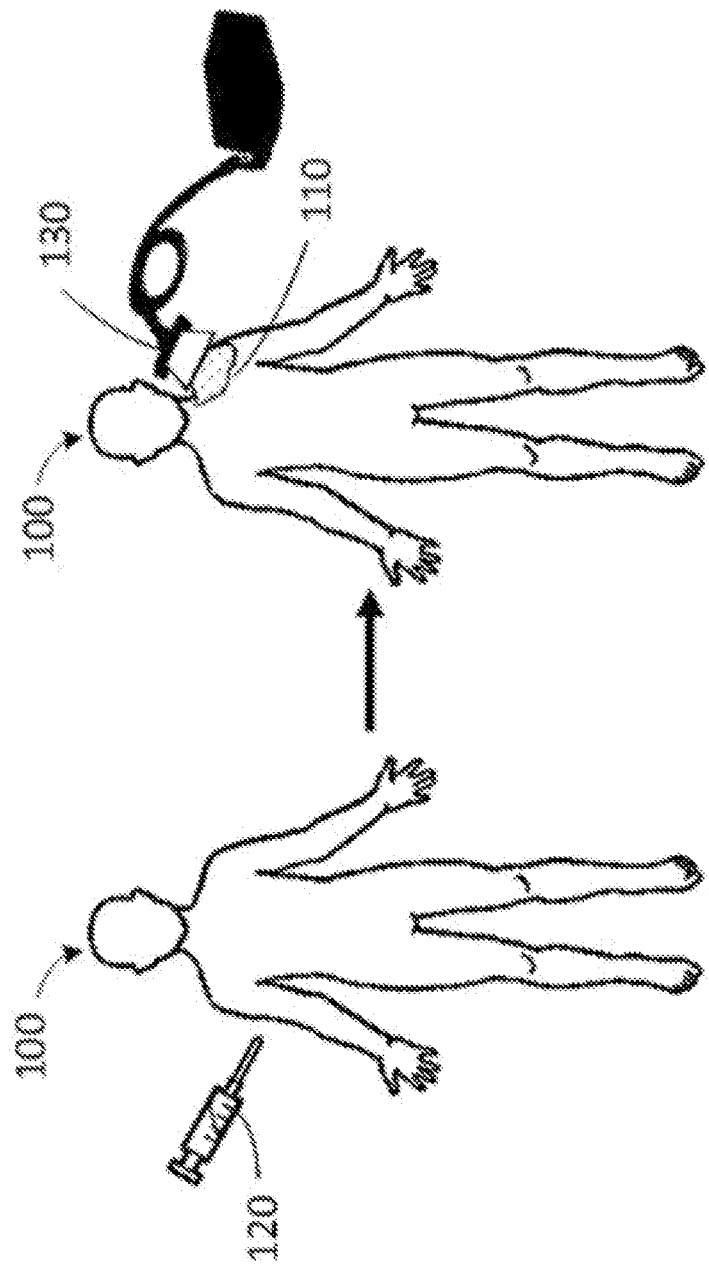
FIG. 45 is a schematic diagram illustrating one embodiment of a method for using the disclosed compounds by injection of the compound followed by targeted delivery of light of a desired wavelength to the external surface of the skin.

With reference to FIG. 45, a subject 100 with a tumor 110 may be treated with a compound according to any one of Formulas I-V that comprises an antibody or ligand capable of recognizing and binding to an antigen or receptor on a tumor cell surface. In the example shown in FIG. 45, the compound 120 is administered via intravenous injection. A period of time is allowed to elapse during which the compound preferentially accumulates at the tumor site as the antibody or ligand moiety binds to the tumor. A target portion of the subject subsequently is selectively irradiated with an effective amount of NIR or SWIR light energy of a desired wavelength using an external light applicator 130. The light applicator 130 applies the light to a target area limited to the region of the tumor 110, thereby producing fluorescence of the compound. The tumor is visualized by detecting the fluorescence.

A therapeutically effective amount of a second agent may be co-administered with the compound according to Formula I or salt thereof. The compound (or salt thereof) and the second agent may be administered either separately or together in a single composition. The second agent may be administered by the same route or a different route. If administered concurrently, the compound (or salt thereof) and the second agent may be combined in a single pharmaceutical composition or may be administered concurrently as two pharmaceutical compositions. The second agent may be, for example, an anti-tumor agent or an angiogenesis inhibitor.

In view of the many possible embodiments to which the principles of the disclosed invention may be applied, it should be recognized that the illustrated embodiments are only preferred examples of the invention and should not be taken as limiting the scope of the invention.

Rather, the scope of the invention is defined by the following claims. We therefore claim as our invention all that comes within the scope and spirit of these claims.

We claim:

1. A compound having a chemical structure according to Formula I, or a stereoisomer or pharmaceutically acceptable salt thereof:

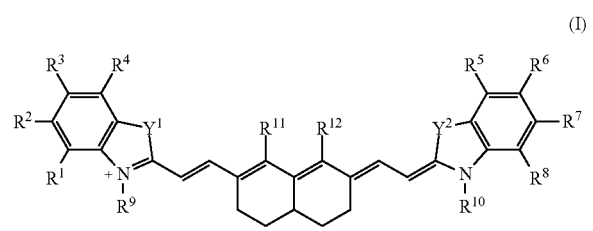

(I)

wherein $R^1$-$R^8$ independently are H, sulfonate, —N($R^a$)$_2$, aliphatic, heteroaliphatic, aliphatic sulfonate, aminoaliphatic, —C(O)O$R^a$, trityl, deuterium, or a group comprising a conjugatable moiety, a targeting agent, or a drug, where each $R^a$ independently is H, aliphatic, heteroaliphatic, or deuterium;

$R^9$ and $R^{10}$ independently are aliphatic sulfonate, —(CH$_2$CH$_2$O)$_n$$R^b$, aliphatic, aminoaliphatic, or alkoxy, where n is an integer ≥1 and $R^b$ is aliphatic, H, or deuterium;

$R^{11}$ and $R^{12}$ together with the rings to which they are attached form a fused ring system, or $R^{11}$ and $R^{12}$ independently are halo; and $Y^1$ and $Y^2$ independently are C($R^c$)$_2$, O, N($R^d$), S, or Se, wherein each $R^c$ independently is aliphatic, H, —(OCH$_2$CH$_2$)$_x$OH where x is an integer ≥2, trityl, deuterium, or a group comprising a conjugatable moiety, a targeting agent, or a drug, and each $R^d$ independently is H, aliphatic, heteroaliphatic, or deuterium.

2. The compound according to claim 1, wherein:
(i) $R^3$ and $R^6$ are sulfonate; or
(ii) $R^1$, $R^2$, $R^4$, $R^5$, $R^7$, and $R^8$ are H; or
(iii) both (i) and (ii).

3. The compound according to claim 1, wherein:
$R^9$ and $R^{10}$ independently are $C_1$-$C_{10}$ alkyl sulfonate; or
$R^9$ and $R^{10}$ are —(CH$_2$CH$_2$O)$_n$$R^b$ where each n independently is 1, 2, 3, 4, 5, 6, 7, 8, 9, or 10, and each $R^b$ independently is $C_1$-$C_3$ alkyl or H; or
$R^9$ and $R^{10}$ independently are $C_1$-$C_{20}$ alkyl.

4. The compound according to claim 1, wherein:
$Y^1$ and $Y^2$ are C($R^c$)$_2$ where each $R^c$ is $C_1$-$C_3$ alkyl; or
$Y^1$ and $Y^2$ are C($R^c$)$_2$ where at least one $R^c$ is a group comprising a conjugatable moiety, a targeting agent, or a drug; or
$Y^1$ and $Y^2$ are O.

5. The compound according to claim 1, wherein $R^{11}$ and $R^{12}$ together with the rings to which they are attached form a fused ring system.

6. The compound according to claim 5, having a chemical structure according to Formula II, Formula III, Formula IV, Formula V, or a stereoisomer or pharmaceutically acceptable salt thereof:

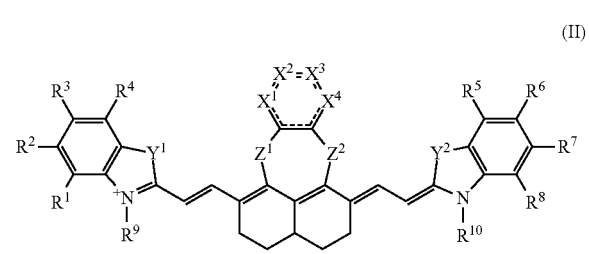

(II)

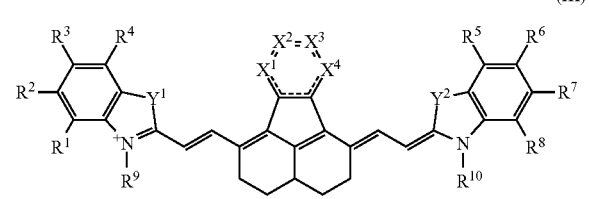

(III)

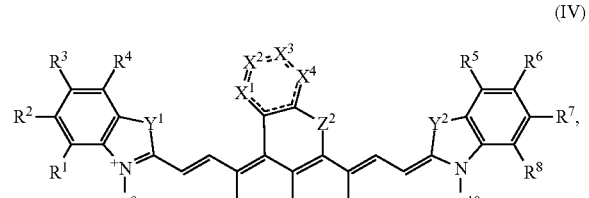

(IV)

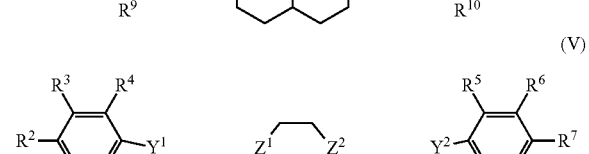

(V)

wherein each bond depicted as "┄┄┄┄" is a single or double bond as needed to satisfy valence requirements;
$Z^1$ and $Z^2$ independently are O, S, or N($R^d$) where $R^d$ is H, aliphatic, heteroaliphatic, or deuterium;
$X^1$-$X^4$ independently are C$R^{13}$, or one of $X^1$-$X^4$ is O and the others of $X^1$-$X^4$ are C$R^{13}$; and
each $R^{13}$ independently is H, sulfonate, —(CH$_2$)$_m$C(O)$R^e$, —(CH$_2$)$_m$OC(O)$R^e$, —N($R^a$)$_2$, aliphatic, heteroaliphatic, aliphatic sulfonate, aminoaliphatic, trityl, deuterium, or a group comprising a conjugatable moiety, a targeting agent, or a drug, where
m is an integer ≥0, and
$R^e$ is —O$R^a$ or —N($R^f$)$_2$, and each $R^f$ independently is H, aliphatic, aliphatic sulfonate, —(CH$_2$)$_n$C(O)O$R^a$, —(CH$_2$CH$_2$O)$_n$CH$_2$C(O)O$R^a$, aryl, heteroaliphatic, or deuterium, where n is an integer ≥1.

7. The compound according to claim 6, wherein $Z^1$ and $Z^2$ are O.

8. The compound according to claim 6, wherein:
one of $X^1$-$X^4$ is $CR^{13}$ where $R^{13}$ is a group comprising a conjugatable moiety, a targeting agent, or a drug, and the others of $X^1$-$X^4$ are CH; or
one of $X^2$ and $X^3$ is C—$(CH_2)_p$C(O)$R^e$, the other of $X^2$ and $X^3$ is CH, and $X^1$ and $X^4$ are CH; or
either $X^2$ and $X^4$ are C-sulfonate and $X^1$ and $X^3$ are CH, or $X^1$ and $X^3$ are C-sulfonate and $X^2$ and $X^4$ are CH; or $X^1$-$X^4$ are CH; or
one of $X^1$-$X^4$ is O and the others of $X^1$-$X^4$ are CH; or
one of $X^1$-$X^4$ is O, another of $X^1$-$X^4$ is $CR^{13}$ where $R^{13}$ is a group comprising a conjugatable moiety, a targeting agent, or a drug, and the others of $X^1$-$X^4$ are CH.

9. The compound according to claim 6, wherein:
$Y^1$ and $Y^2$ are $C(R^c)^2$ and each $R^c$ is methyl; or
$Y^1$ and $Y^2$ are O.

10. The compound according to claim 1, wherein:
at least one of $R^1$-$R^8$ or $R^{13}$ is a group comprising a conjugatable moiety, a targeting agent, or a drug; or
at least one of $Y^1$ and $Y^2$ is $C(R^c)_2$ where one $R^c$ is a group comprising a conjugatable moiety, a targeting agent, or a drug.

11. The compound according to claim 10, wherein:
at least one of $R^1$-$R^8$ or $R^{13}$ is a group comprising a conjugatable moiety; or
at least one of $Y^1$ and $Y^2$ is $C(R^c)_2$ where one $R^c$ is a group comprising a conjugatable moiety.

12. The compound according to claim 10, wherein at least one of $R^1$-$R^8$ or $R^{13}$ is a group comprising a targeting agent or at least one of $Y^1$ and $Y^2$ is $C(R^c)_2$ where one $R^c$ is a group comprising a targeting agent, and the targeting agent is an antibody.

13. The compound according to claim 1, wherein the compound is:

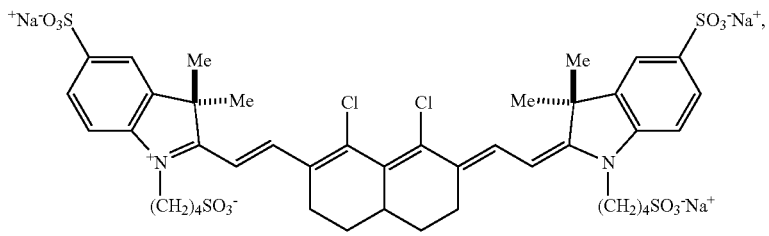

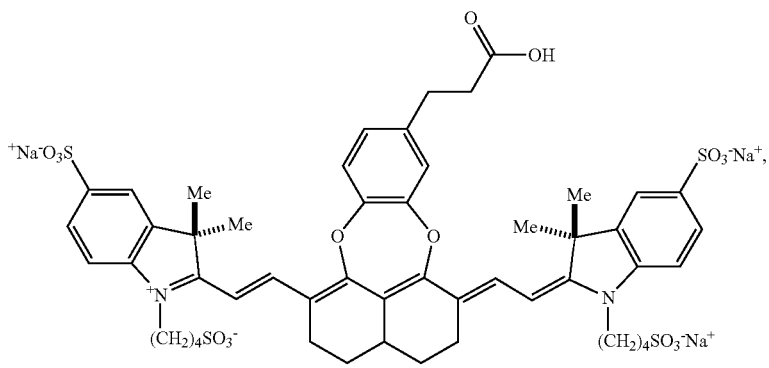

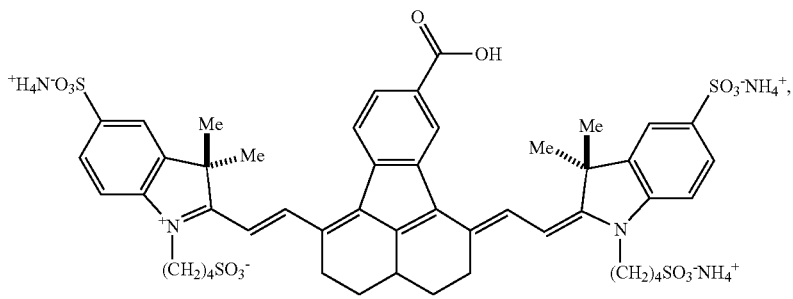

-continued
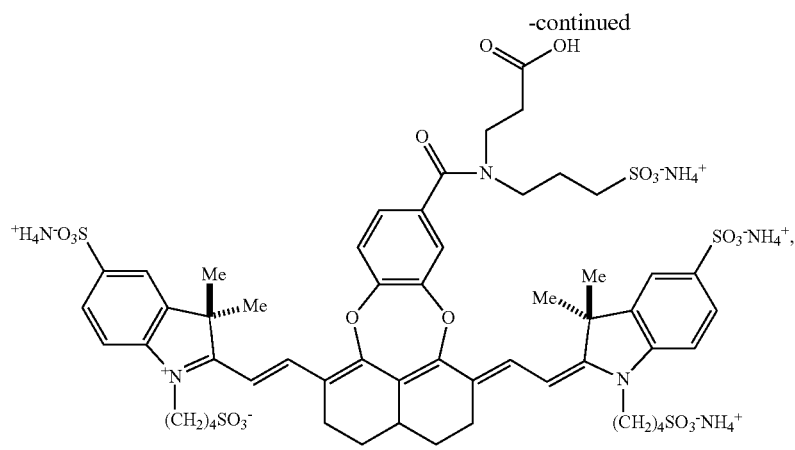
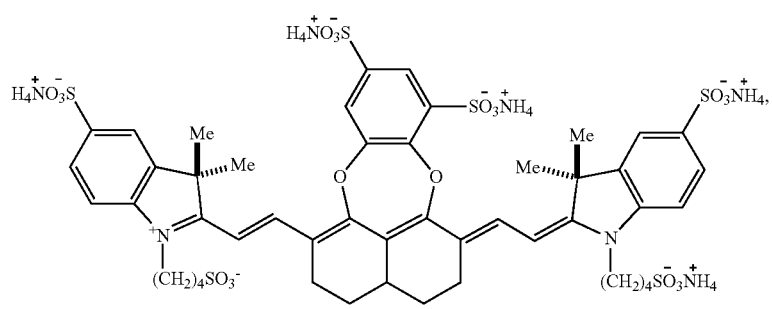
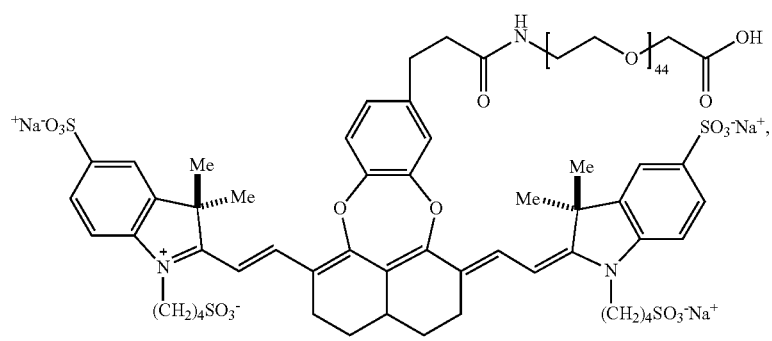
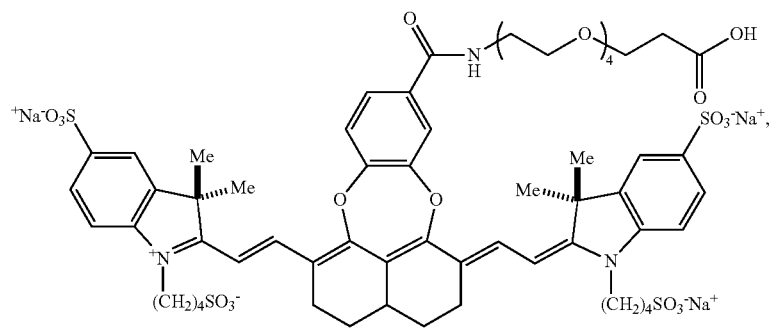
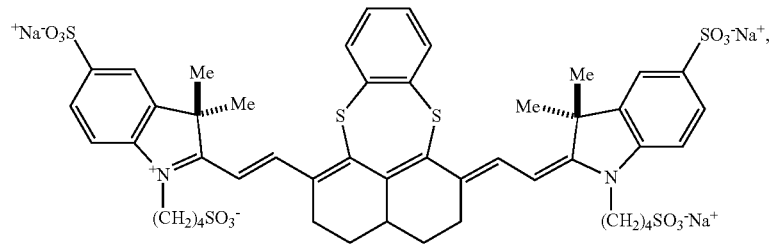

-continued
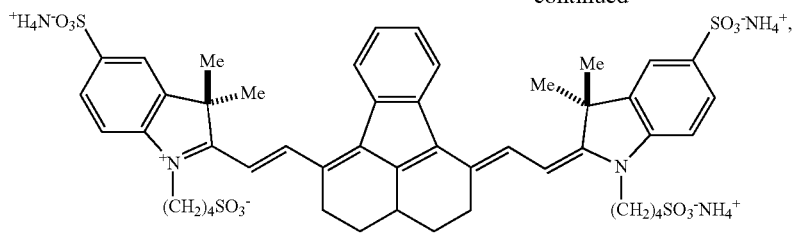
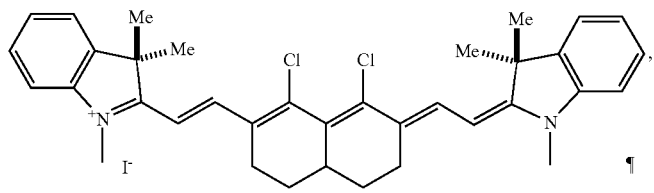
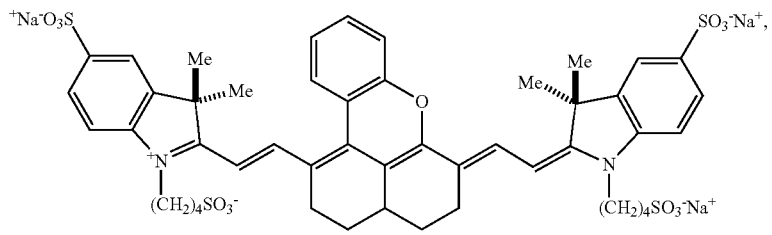
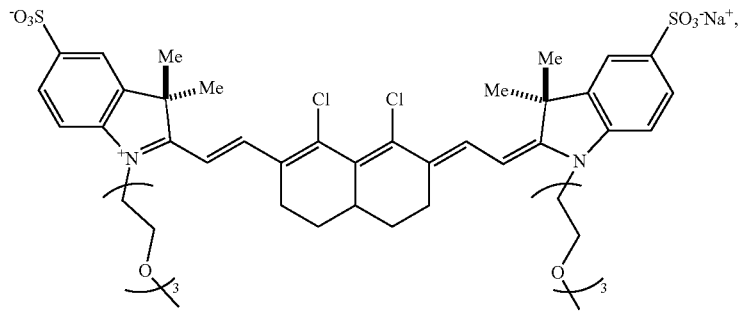
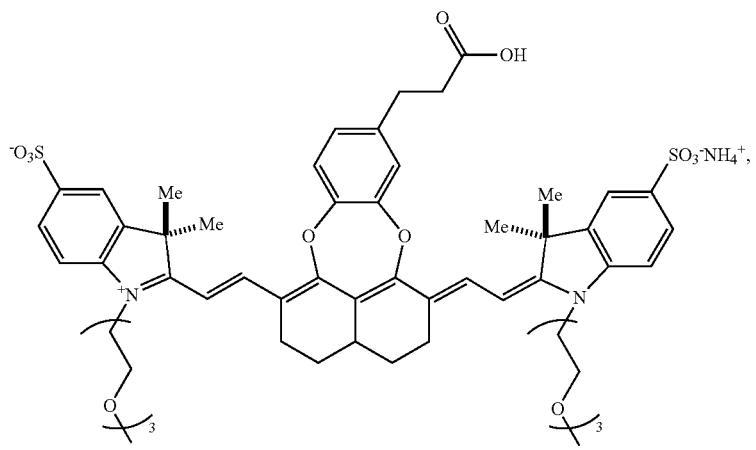

-continued
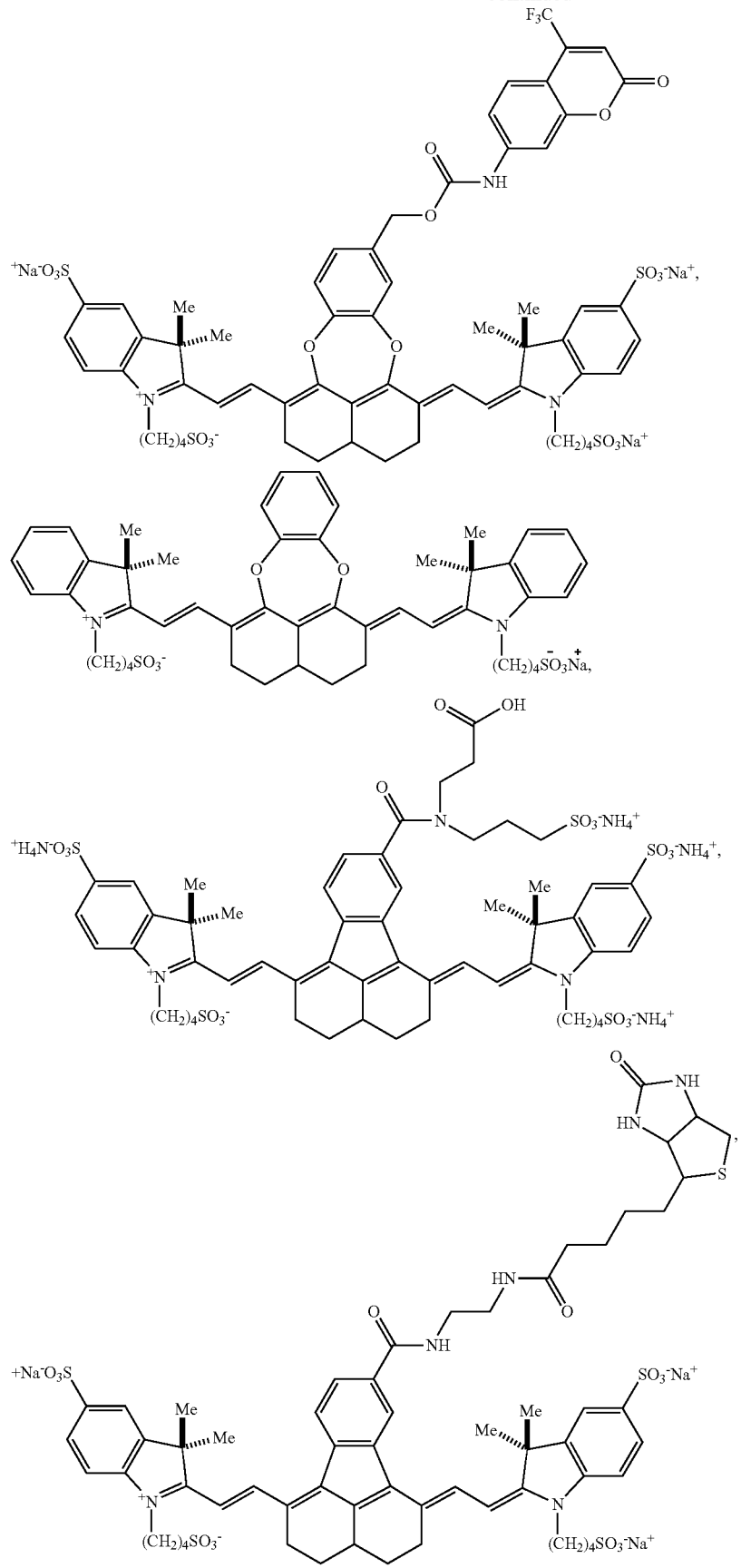

-continued
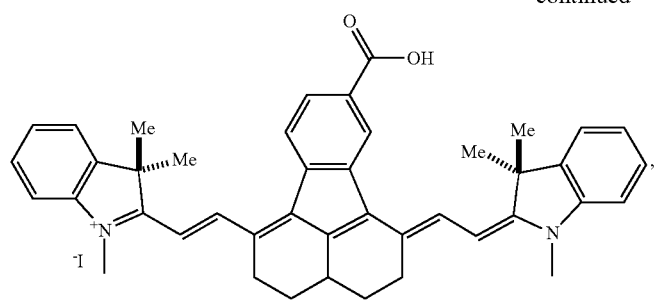
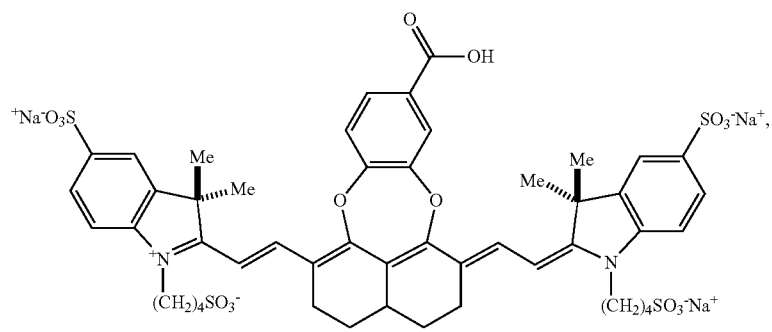
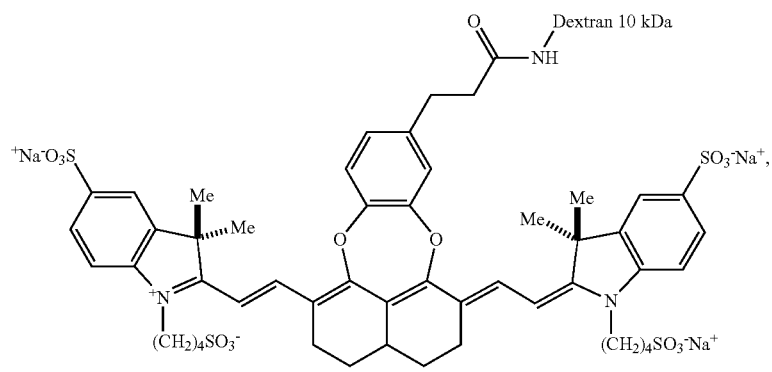
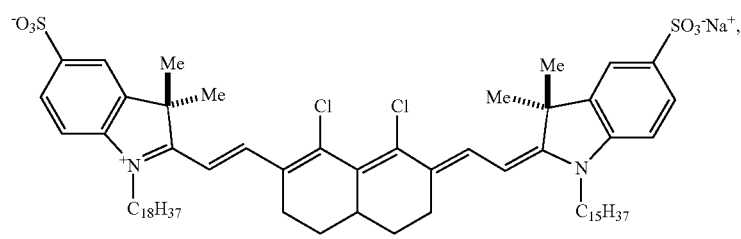
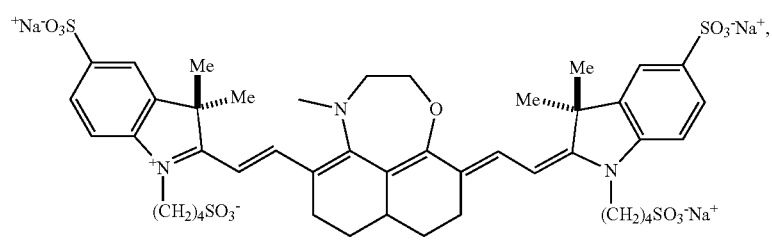

-continued
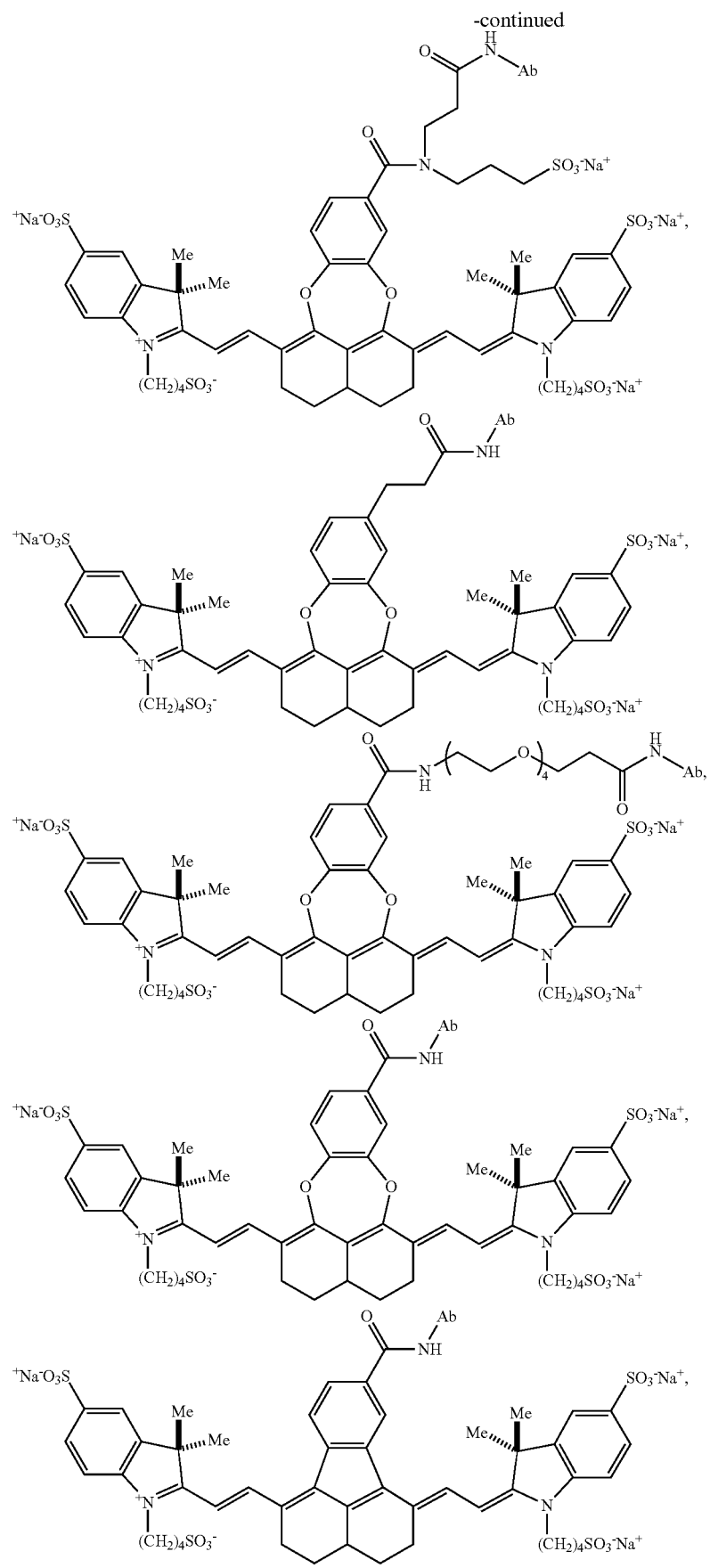

-continued
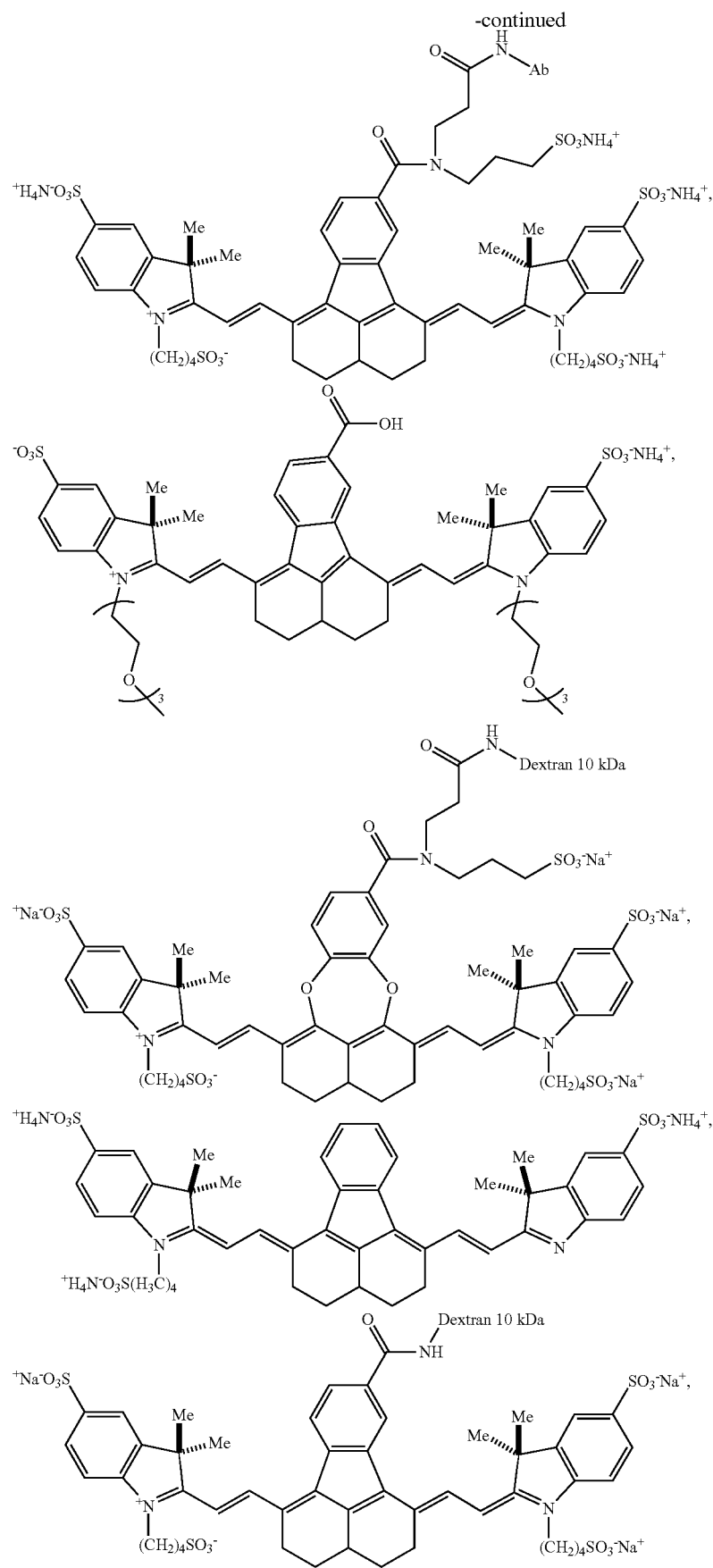

-continued
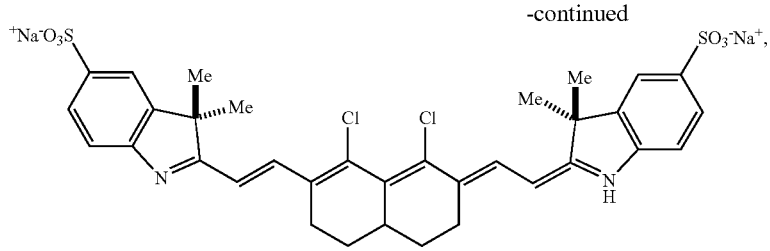
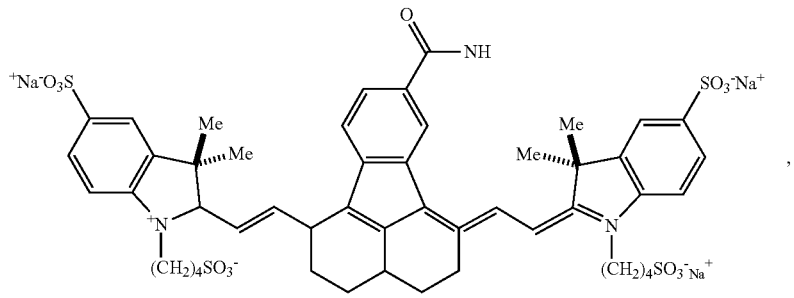
Dextran 70 kDa
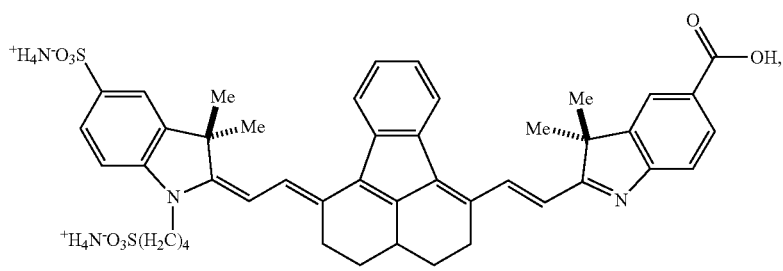
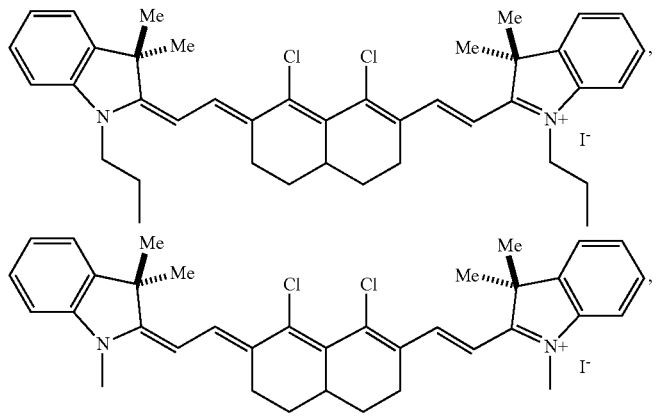
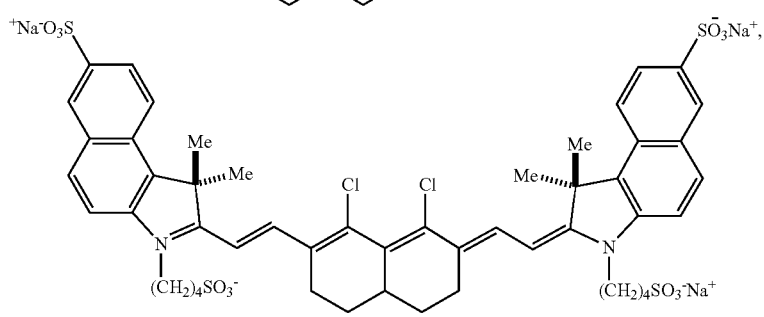

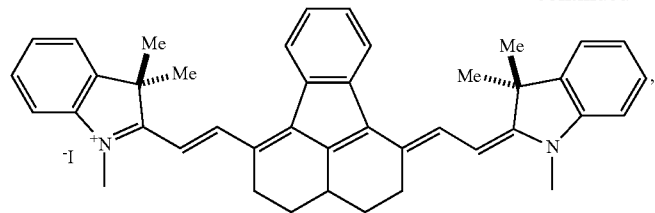
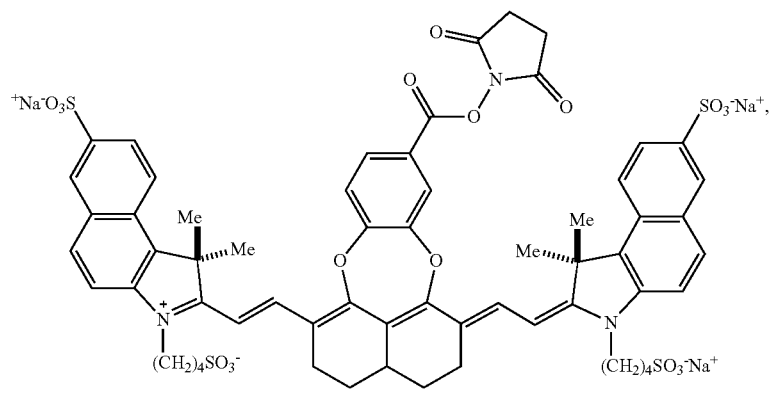
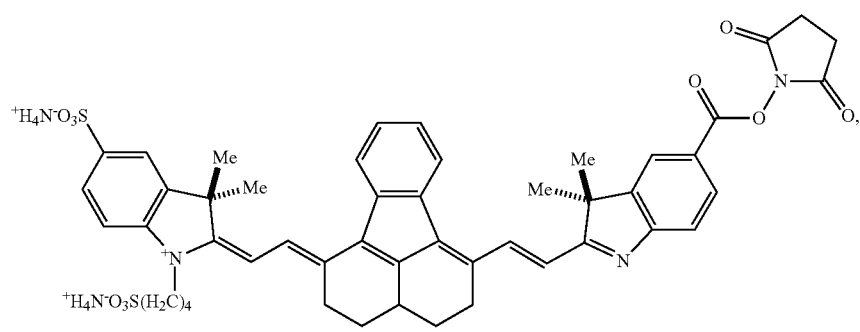
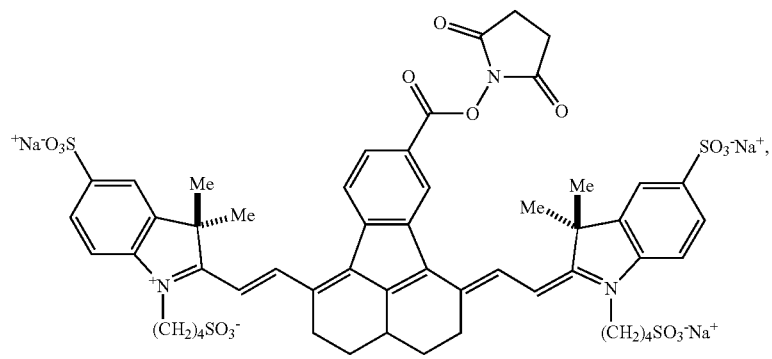

-continued

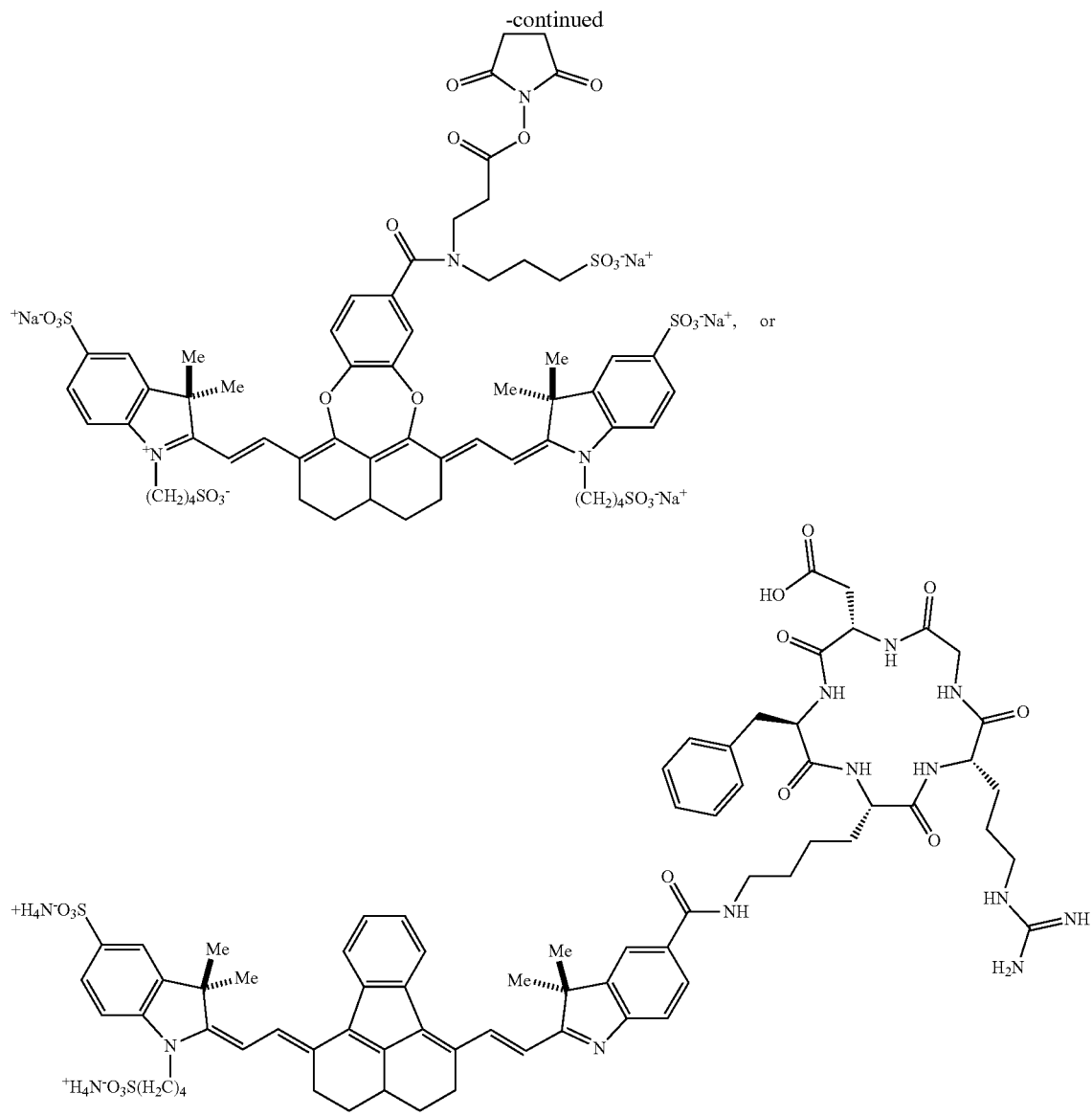

where Ab is an antibody.

14. A pharmaceutical composition comprising:
a compound according to claim 1; and
a pharmaceutically acceptable carrier.

15. A method for using a compound according to claim 1, comprising:
combining the compound with a sample; and
visualizing the compound in the sample by
irradiating the sample with targeted application of a quantity of light having a wavelength in the near-infrared or short wave infrared range and a selected intensity, wherein the quantity of light is sufficient to produce fluorescence of the compound, and
detecting any fluorescence emitted by the compound.

16. The method according to claim 14, wherein at least one of $R^1$-$R^{13}$ comprises a targeting agent and the sample comprises a target capable of binding with the targeting agent, the method further comprising:
combining the compound with the sample under conditions effective to provide binding of the targeting agent and the target; and
imaging the target by visualizing the compound bound to the target.

17. The method of claim 15, wherein the sample is a tissue sample, a biological fluid, or a target area within a subject.

18. The method of claim 17, wherein the sample is a target area within a subject, the method further comprising:
administering the compound, or a pharmaceutical composition comprising the compound, to the subject;
subsequently visualizing the compound by irradiating the compound by targeted application of the quantity of light to a targeted portion of the subject; and
detecting any fluorescence emitted by the compound in the targeted portion of the subject.

19. The method of claim 18, wherein the target area is a tumor site and the targeted portion of the subject includes the tumor site, the method further comprising excising at least a portion of the tumor from the subject after detecting the fluorescence in the targeted portion of the subject.

* * * * *